United States Patent
Liu et al.

(10) Patent No.: US 10,130,630 B2
(45) Date of Patent: Nov. 20, 2018

(54) BTK INHIBITORS

(71) Applicant: MERCK SHARP & DOHME CORP., Rahway, NJ (US)

(72) Inventors: Jian Liu, Edison, NJ (US); Joseph A. Kozlowski, Princeton, NJ (US); Abdul-Basit Alhassan, Scotch Plains, NJ (US); Rajan Anand, Fanwood, NJ (US); Sobhana Babu Boga, Scotch Plains, NJ (US); Deodial Guy Guiadeen, Chesterfield, NJ (US); Wensheng Yu, Edison, NJ (US); Younong Yu, East Brunswick, NJ (US); Shilan Liu, Shanghai (CN); Hao Wu, Shanghai (CN); Chundao Yang, Shanghai (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/538,976

(22) PCT Filed: Dec. 17, 2015

(86) PCT No.: PCT/US2015/066218
§ 371 (c)(1),
(2) Date: Jun. 22, 2017

(87) PCT Pub. No.: WO2016/109215
PCT Pub. Date: Jul. 7, 2016

(65) Prior Publication Data
US 2017/0340631 A1 Nov. 30, 2017

(30) Foreign Application Priority Data
Dec. 31, 2014 (WO) ............... PCT/CN2014/095770

(51) Int. Cl.
| | |
|---|---|
| *A61K 31/4985* | (2006.01) |
| *A61K 31/5377* | (2006.01) |
| *A61K 31/541* | (2006.01) |
| *A61K 31/55* | (2006.01) |
| *C07D 519/00* | (2006.01) |
| *A61K 45/06* | (2006.01) |
| *C07K 16/28* | (2006.01) |

(52) U.S. Cl.
CPC ...... *A61K 31/4985* (2013.01); *A61K 31/5377* (2013.01); *A61K 31/541* (2013.01); *A61K 31/55* (2013.01); *A61K 45/06* (2013.01); *C07D 519/00* (2013.01); *C07K 16/2887* (2013.01); *A61K 2300/00* (2013.01)

(58) Field of Classification Search
CPC ............ A61K 31/4985; A61K 31/5377; A61K 31/541; A61K 31/55; C07D 519/00
See application file for complete search history.

(56) References Cited

U.S. PATENT DOCUMENTS

| | | |
|---|---|---|
| 8,673,925 B1 | 3/2014 | Goldstein |
| 2014/0206681 A1 | 7/2014 | Kim et al. |

FOREIGN PATENT DOCUMENTS

| | | |
|---|---|---|
| EP | 2443929 | 4/2012 |
| WO | WO2005014599 | 2/2005 |
| WO | WO2011095556 A1 | 8/2011 |
| WO | WO2013010868 | 1/2013 |
| WO | WO2013113097 A1 | 8/2013 |
| WO | WO2014113932 | 7/2014 |
| WO | WO2014116504 | 7/2014 |
| WO | WO20141141185 | 7/2014 |
| WO | WO2016106629 A1 | 7/2016 |

*Primary Examiner* — Brenda L Coleman
(74) *Attorney, Agent, or Firm* — Matthew A. Leff; Laura M. Ginkel

(57) ABSTRACT

The present invention provides Bruton's Tyrosine Kinase (Btk) inhibitor compounds according to Formula (I), or pharmaceutically acceptable salts or stereoisomers thereof, or to pharmaceutical compositions comprising these compounds and to their use in therapy. In particular, the present invention relates to the use of Btk inhibitor compounds of Formula (I) in the treatment of Btk mediated disorders.

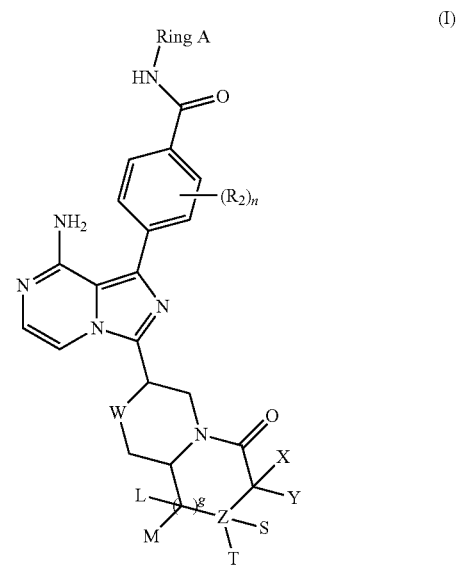

5 Claims, No Drawings
Specification includes a Sequence Listing.

BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll-like receptor signaling was suggested. Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al, Immunological Reviews 288 (2009) pp 149-169].

Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors, e.g. Imidazo[1,5-f][1,2,4]triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}Fyn^{-/-}$ and $Src^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoiseis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

Definitions

The terms used herein have their ordinary meaning.

The term "amount effective" or "effective amount" as used herein, refers to an amount of the compound of Formula I and/or an additional therapeutic agent, or a composition thereof, that is effective in producing the desired therapeutic, ameliorative, inhibitory or preventative effect when administered to a subject suffering from a BTK-mediated disease or disorder. In the combination therapies of the present invention, an effective amount can refer to each individual agent or to the combination as a whole, wherein the amounts of all agents administered are together effective, but wherein the component agent of the combination may not be present individually in an effective amount.

The term "cyclic moiety" refers to cyclopropyl, cyclobutyl and cyclopentyl and also refers to cyclic structures formed as a result of variables coming together to form a carbon bridge (for example, variables X and T forming a carbon bridge as highlighted in example compound 16).

The term "halogen", as used herein, refers to fluorine, chlorine, bromine or iodine. Fluorine, chlorine or bromine being preferred halogens; fluorine being more preferred.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

A "subject" is a human or non-human mammal. In one embodiment, a subject is a human. In another embodiment, the subject is a chimpanzee.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides Btk inhibitor compounds according to Formula I or pharmaceutically acceptable salts thereof

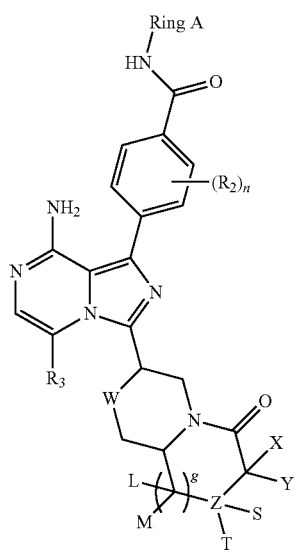

Formula I wherein:
Ring A is selected from the group consisting of

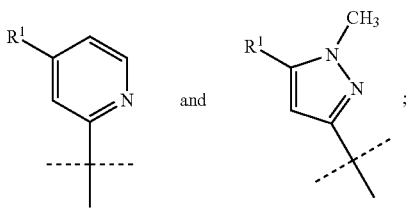

n is 0, 1 or 2; g is 0 or 1;
W is $CH_2$ or O;
Z is C or N;
X and Y are independently H or X and Y can come together to form cyclopropyl, cyclobutyl or cyclopentyl,
S and T are independently H, F, OH, $OCH_3$, methyl, ethyl or S and T can come together to form cyclopropyl, provided that when Z is C then S and T can come together to form =O,
M and L are independently H or M and L can come together to form cyclopropyl,
X and T can come together to form a one to three carbon bridge,
wherein one of X and Y, S and T, M and L, and X and T must be a cyclic moiety;
$R_1$ is selected from the group consisting of hydrogen, triflouromethyl, cyclopropyl, methyl, and cyano;
$R_2$ is independently selected from the group consisting of methoxy, ethoxy and halogen; and
$R_3$ is hydrogen, halogen, methyl, ethyl, propyl or isopropyl.

The present invention provides Btk inhibitor compounds according to Formula Ia or pharmaceutically acceptable salts thereof

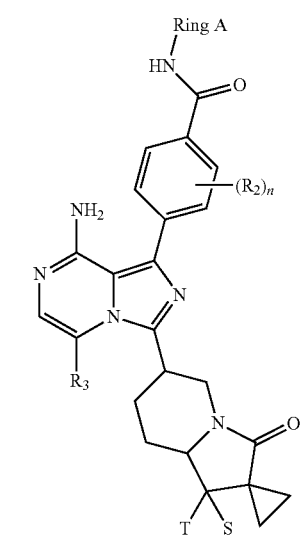

Formula Ia wherein:
Ring A is selected from the group consisting of

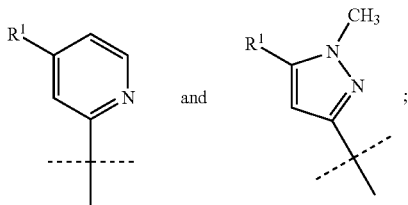

n is 0, 1 or 2;
S and T are independently H, F, OH, OCH₃, methyl, ethyl or S and T can come together to form =O;
R₁ is selected from the group consisting of hydrogen, triflouromethyl, cyclopropyl, methyl, and cyano;
R₂ is independently selected from the group consisting of methoxy, ethoxy and halogen; and
R₃ is hydrogen, halogen, methyl, ethyl, propyl or isopropyl.

The present invention provides Btk inhibitor compounds according to Formula Ib or pharmaceutically acceptable salts thereof

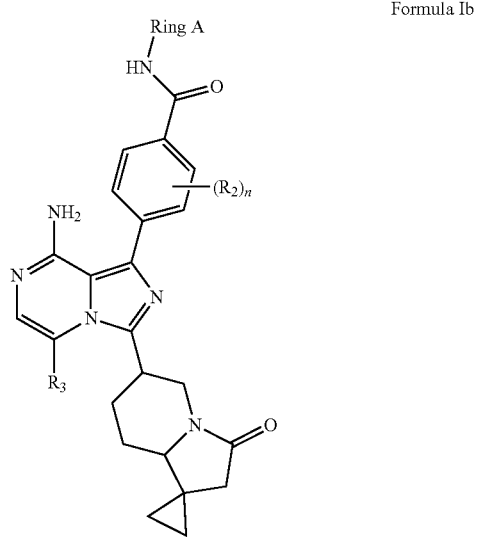

Formula Ib wherein:
Ring A is selected from the group consisting of

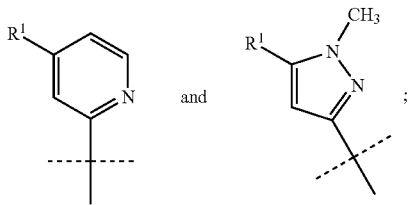

n is 0, 1 or 2;
R₁ is selected from the group consisting of hydrogen, triflouromethyl, cyclopropyl, methyl, and cyano;
R₂ is independently selected from the group consisting of methoxy, ethoxy and halogen; and
R₃ is hydrogen, halogen, methyl, ethyl, propyl or isopropyl.

Non-limiting examples of the compounds of the present invention include:

4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide;

4-(8-amino-3-((6'S,8a'R)-1',1'-difluoro-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide;

4-(8-amino-3-((6'R,8a'S)-1',1'-difluoro-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide;

4-(8-amino-3-((6'R,8a'S)-3'-oxohexahydro-1'H-spiro[cyclopropane-1,2'-indolizin]-6'-ypimidazo[1,5-a]pyrazin-1-yl)-3-ethoxy-5-fluoro-N-(4-(trifluoromethyl)pyridin-2-yl)benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-N-[4-(trifluoromethyl)pyridin-2-yl]benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-3-fluoro-N-[4-(trifluoromethyl)pyridin-2-yl]benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-N-(4-methylpyridin-2-yl)benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-N-(4-cyclopropylpyridin-2-yl)benzamide;

4-{8-amino-3-[(1'S,6'R,8a'S)-1'-hydroxy-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;

4-{8-amino-3-[(1'S,6'R,8a'S)-1'-hydroxy-3'-oxohexahydrospiro[cyclopropane-1,2'-indolizin]-6'-yl)imidazo[1,5-a]pyrazin-1-yl}-3-ethoxy-N-(4-(trifluoromethyl)pyridin-2-yl]benzamide;

4-(8-amino-((1'S,6'R,8a'S)-1'-hydroxy-3'-oxohexahydro-1'H-spiro[cyclopropane-1,2'-indolizin]-6'-yl)imidazo[1,5-a]pyrazin-1-yl)-3-fluoro-N-(4-(trifluoromethyl)pyridin-2-yl)benzamide;

4-(8-amino-3-1'S,6'R,8a'S)-1'-hydroxy-3'-oxohexahydro-1'H-spiro[cyclopropane-1,2'-indolizin]-6'-yl)imidazo[1,5-a]pyrazin-1-yl)-N-(4-cyclopropylpyridin-2-yl)benzamide;

4-(8-amino-3-1'S,6'R,8a'S)-1'-methoxy-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide;

4-{8-amino-3-[(5aS,8R,11aR)-11-oxodecahydro-1H-pyrido[1,2-a]pyrrolo[1,2-d]pyrazin-8-yl]imidazo[1,5-a]pyrazin-1-yl}-3-ethoxy-N-[4-(trifluoromethyl)pyridin-2-yl]benzamide;

4-{8-amino-3-[(5aS,8R,11aS)-11-oxodecahydro-1H-pyrido[1,2-a]pyrrolo[1,2-d]pyrazin-8-yl]imidazo[1,5-a]pyrazin-1-yl}-3-ethoxy-N-[4-(trifluoromethyl)pyridin-2-yl]benzamide;

4-{8-amino-3-[(7'R,9a'S)-4'-oxohexahydro-2'H-spiro[cyclobutane-1,3'-pyrido[1,2-a]pyrazin]-7'-yl]imidazo[1,5-a]pyrazin-1-yl}-3-ethoxy-N-[4-(trifluoromethyl)pyridin-2-yl]benzamide;

4-{8-amino-3-[(6'R,8a'S)-3'-oxohexahydro-5'H-spiro[cyclopropane-1,1'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'S,8a'R)-3'-oxohexahydro-5'H-spiro[cyclopropane-1,1'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'R, 8a'S)-3'-oxohexahydro-5'H-spiro[cyclopropane-1,1'-indolizin]-6'-yl]imidazo[1,5-a]pyrazin-1-yl}-3-ethoxy-5-fluoro-N-[4-(trifluoromethyl)pyridin-2-yl]benzamide;

4-{8-amino-3-[(6'R,8a'S)-3'-oxohexahydro-5'H-spiro[cyclopropane-1,1'-indolizin]-6'-yl]imidazo[1,5-a]pyrazin-1-yl}-N-(4-cyclopropylpyridin-2-yl)-3-ethoxy-5-fluorobenzamide;

4-[8-amino-5-fluoro-3-(3'-oxohexahydro-5'H-spiro[cyclopropane-1,1'-indolizin]-6'-yl)imidazo[1,5-a]pyrazin-1-yl]-3-ethoxy-5-fluoro-N-[1-methyl-5-(trifluoromethyl)-1H-pyrazol-3-yl]benzamide;

4-[8-amino-5-fluoro-3-(3'-oxohexahydro-5'H-spiro[cyclopropane-1,1'-indolizin]-6'-yl)imidazo[1,5-a]pyrazin-1-yl]-3-ethoxy-5-fluoro-N-[1-methyl-5-(trifluoromethyl)-1H-pyrazol-3-yl]benzamide;

4-[8-amino-3-(2-oxooctahydro-1H-cyclopropa[a]indolizin-5-yl)imidazo[1,5-a]pyrazin-1-yl]-3-ethoxy-N-[4-(trifluoromethyl)pyridin-2-yl]benzamide;

4-[8-amino-3-(2-oxooctahydro-1H-cyclopropa[a]indolizin-5-yl)imidazo[1,5-a]pyrazin-1-yl]-3-ethoxy-N-[4-(trifluoromethyl)pyridin-2-yl]benzamide;

4-[8-amino-3-(2-oxooctahydro-1H-cyclopropa[a]indolizin-5-yl)imidazo[1,5-a]pyrazin-1-yl]-3-ethoxy-N-[4-(trifluoromethyl)pyridin-2-yl]benzamide;

4-{8-amino-3-[(6'R, 8a'S)-1',1'-difluoro-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'R, 8a'S)-1',1'-difluoro-3'-oxohexahydrospiro[cyclopropane-1,2'-indolizin]-6'-yl]imidazo[1,5-a]pyrazin-1-yl}-3-ethoxy-5-fluoro-N-[4-(trifluoromethyl)pyridin-2-yl]benzamide;

4-{8-amino-3-[(6'S,8a'R)-1',1'-difluoro-3'-oxohexahydrospiro[cyclopropane-1,2'-indolizin]-6'-yl]imidazo[1,5-a]pyrazin-1-yl}-3-methoxy-N-[4-(trifluoromethyl)pyridin-2-yl]benzamide;

4-{8-amino-3-[(6'R, 8a'S)-1',1'-difluoro-3'-oxohexahydrospiro[cyclopropane-1,2'-indolizin]-6'-yl]imidazo[1,5-a]pyrazin-1-yl}-3-fluoro-5-methoxy-N-[4-(trifluoromethyl)pyridin-2-yl]benzamide;

4-{8-amino-3-[(6'S,8a'R)-1',1'-difluoro-3'-oxohexahydrospiro[cyclopropane-1,2'-indolizin]-6'-yl]imidazo[1,5-a]pyrazin-1-yl}-N-[4-(trifluoromethyl)pyridin-2-yl]benzamide;

4-{8-amino-3-[(6'R, 8a'S)-1',1'-difluoro-3'-oxohexahydrospiro[cyclopropane-1,2'-indolizin]-6'-yl]imidazo[1,5-a]pyrazin-1-yl}-3-ethoxy-N-[1-methyl-5-(trifluoromethyl)-1H-pyrazol-3-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-2-chloro-5-ethoxy-N-[1-methyl-5-(trifluoromethyl)-1H-pyrazol-3-yl]benzamide;

4-{8-amino-3-[(3R,6aR,11aR)-6-oxooctahydro-1H,6H-pyrrolo[1',2':4,5]pyrazino[2,1-c][1,4]oxazin-3-yl]imidazo[1,5-a]pyrazin-1-yl}-3-ethoxy-N-[4-(trifluoromethyl)pyridin-2-yl]benzamide;

4-{8-amino-3-[(3R,6aS,11aR)-6-oxooctahydro-1H,6H-pyrrolo[1',2':4,5]pyrazino[2,1-c][1,4]oxazin-3-yl]imidazo[1,5-a]pyrazin-1-yl}-3-ethoxy-N-[4-(trifluoromethyl)pyridin-2-yl]benzamide;

4-[8-amino-5-chloro-3-(3'-oxohexahydro-5'H-spiro[cyclopropane-1,1'-indolizin]-6'-yl)imidazo[1,5-a]pyrazin-1-yl]-N-(4-cyanopyridin-2-yl)-3-ethoxy-5-fluorobenzamide;

4-[8-amino-3-(3'-oxohexahydro-5'H-spiro[cyclopropane-1,1'-indolizin]-6'-yl)imidazo[1,5-a]pyrazin-1-yl]-N-(4-cyanopyridin-2-yl)-3-ethoxy-5-fluorobenzamide;

4-[8-amino-3-(4'-oxohexahydro-2'H,6'H-spiro[cyclopropane-1,1'-pyrido[1,2-a]pyrazin]-7'-yl)imidazo[1,5-a]pyrazin-1-yl]-3-ethoxy-N-[4-(trifluoromethyl)pyridin-2-yl]benzamide;

4-{8-amino-3-[(7'R,9a'S)-4'-oxohexahydro-2'H-spiro[cyclopropane-1,3'-pyrido[1,2-a]pyrazin]-7'-yl]imidazo[1,5-a]pyrazin-1-yl}-N-[4-(trifluoromethyl)pyridin-2-yl]benzamide;

4-{8-amino-3-[(7'R,9a'S)-4'-oxohexahydro-2'H-spiro[cyclopropane-1,3'-pyrido[1,2-a]pyrazin]-7'-yl]imidazo[1,5-a]pyrazin-1-yl}-3-methoxy-N-[4-(trifluoromethyl)pyridin-2-yl]benzamide;

4-[8-amino-3-(4'-oxohexahydro-2'H,6'H-spiro[cyclopropane-1,1'-pyrido[1,2-a]pyrazin]-7'-yl)imidazo[1,5-a]pyrazin-1-yl]-3-ethoxy-N-[4-(trifluoromethyl)pyridin-2-yl]benzamide;

4-[8-amino-3-(4'-oxohexahydro-2'H,6'H-spiro[cyclopropane-1,1'-pyrido[1,2-a]pyrazin]-7'-yl)imidazo[1,5-a]pyrazin-1-yl]-3-ethoxy-N-[4-(trifluoromethyl)pyridin-2-yl]benzamide;

4-{8-amino-3-[(7'R,9a'S)-2'-ethyl-4'-oxohexahydro-2'H-spiro[cyclopropane-1,3'-pyrido[1,2-a]pyrazin]-7'-yl]imidazo[1,5-a]pyrazin-1-yl}-3-ethoxy-N-[4-(trifluoromethyl)pyridin-2-yl]benzamide;

4-{8-amino-3-[(3'R,9a'R)-6'-oxohexahydrospiro[cyclopropane-1,7'-pyrazino[2,1-c][1,4]oxazin]-3'-yl]imidazo[1,5-a]pyrazin-1-yl}-3-ethoxy-N-[4-(trifluoromethyl)pyridin-2-yl]benzamide;

4-{8-amino-3-[(3'R,9a'R)-6'-oxohexahydrospiro[cyclopentane-1,7'-pyrazino[2,1-c][1,4]oxazin]-3'-yl]imidazo[1,5-a]pyrazin-1-yl}-3-ethoxy-N-[4-(trifluoromethyl)pyridin-2-yl]benzamide;

4-{8-amino-3-[(6'S,8a'R)-3'-oxohexahydrospiro[cyclopropane-1,2'-indolizin]-6'-yl]imidazo[1,5-a]pyrazin-1-yl}-3-methoxy-N-[4-(trifluoromethyl)pyridin-2-yl]benzamide; and 4-{8-amino-3-[(6'S,8a'R)-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;

or a pharmaceutically acceptable salt thereof.

In a preferred embodiment halogen is F or Cl.

In a preferred embodiment $R_3$ is H or F.

The compounds of this invention include the salts, solvates, hydrates or prodrugs of the compounds. The use of the terms "salt", "solvate", "hydrate", "prodrug" and the like, is intended to equally apply to the salt, solvate, hydrate and prodrug of enantiomers, stereoisomers, rotamers, tautomers, positional isomers, or racemates of the inventive compounds.

Salts

The Btk inhibitor compounds of the present invention, which can be in the form of a free base, may be isolated from the reaction mixture in the form of a pharmaceutically acceptable salt.

The compounds of Formula I can form salts which are also within the scope of this invention. Reference to a compound of Formula I herein is understood to include reference to pharmaceutically acceptable salts thereof, unless otherwise indicated. The term "pharmaceutically acceptable salt(s)" or "salt", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Crystals

The Btk inhibitor compounds of the present invention may exist as amorphous forms or crystalline forms.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Solvates

The compounds having Formula I or the pharmaceutically acceptable salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

Optical Isomers

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Such stereoisomeric forms also include enantiomers and diastereoisomers, etc.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Prodrugs

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herinbelow, by substituting an appropriate isotopically labeled reagent for a non-isotopically labeled reagent.

Utilities

The compounds having Formula I and pharmaceutical compositions thereof can be used to treat or prevent a variety of conditions, diseases or disorders mediated by Bruton's Tyrosine kinase (Btk). Such Btk-mediated conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; and (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula I and salts thereof for use in therapy, and particularly in the treatment of disorders, diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In one embodiment, the present invention provides for the use of a compound of Formula I, or a pharmaceutically acceptable salt thereof for the manufacture of a medicament for the treatment of a Btk-mediated disorder.

In another embodiment, the present invention provides methods of regulating, modulating, or inhibiting Btk for the prevention and/or treatment of disorders related to unregulated or inappropriate Btk activity.

In a further embodiment, the present invention provides a method for treating a subject suffering from a disorder mediated by Btk, which comprises administering to said subject a compound of Formula I or a pharmaceutically acceptable salt thereof in an amount effective to treat the Btk-mediated disorder.

A further aspect of the invention resides in the use of a compound of Formula I or a pharmaceutically acceptable salt thereof for the manufacture of a medicament to be used for the treatment of chronic B cell disorders in which T cells play a prominent role.

Thus, the compounds according to the invention may be used in therapies to treat or prevent Bruton's Tyrosine Kinase (Btk) mediated diseases, conditions and disorders. Btk mediated diseases, conditions and disorders as used herein, mean any disease, condition or disorder in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplastic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barr syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) singaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Combination Therapy

Included herein are methods of treatment and/or pharmaceutical compositions in which at least one compound of Formula I or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

The compound(s) of Formula I and the other pharmaceutically active agent(s) may be administered together or separately and, when administered separately this may occur simultaneously or sequentially in any order. The amounts of the compound(s) of Formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta2-adrenoreceptor agonist and/or the anti-inflammatory corticosteroid can be as described above and/or as described in WO 03/030939 A1. Representative examples of such a "triple" combination are a compound of Formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradeca-dienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-noryincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosphl and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-mannoheptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent, carrier or excipient represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Pharmaceutical Compositions

While it is possible that, for use in therapy, a compound of Formula I, as well as salts, solvates and physiological functional derivatives thereof, may be administered as the raw chemical, it is possible to present the active ingredient as a pharmaceutical composition. Accordingly, the invention further provides a pharmaceutical composition which comprises a compound of Formula I and salts, solvates and physiological functional derivatives thereof, and one or more pharmaceutically acceptable carriers, diluents, or excipients. The compounds of the Formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula I, or salts, solvates and physiological functional derivatives thereof, with one or more pharmaceutically acceptable carriers, diluents or excipients.

Routes of Administration

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula I is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula I or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula I or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device(GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

Injectable Suspension (I.M.) mg/ml

| | |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

Tablet mg/tablet

| | |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

Capsule mg/capsule

| | |
|---|---|
| Compound of Formula I | 25 |
| Lactose Powder | 573.5 |
| Magnesium Stearate | 1.5 |
| | 600 |

Aerosol Per canister

| | |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate Btk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

General Synthesis

The 8-amino-imidazo[1,5-a]pyrazine, 4-amino-imidazo[1,5-f][1,2,4]triazine, 4-amino-pyrazolo[3,4-d]pyrimidine and 4-amino-pyrrolo[1,2-f][1,2,4]triazine derivatives of the present invention can be prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3rd Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

8-amino-imidazo[1,5-a]pyrazine compounds of formula I, wherein $R_1$-$R_x$ have the previously defined meanings, can be prepared by the general synthetic route shown in scheme I.

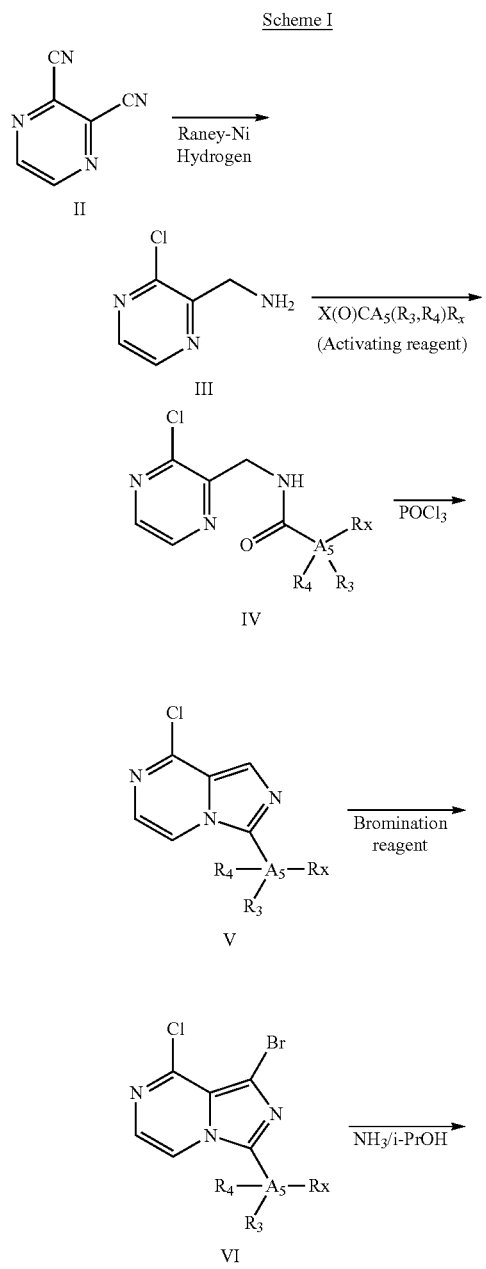

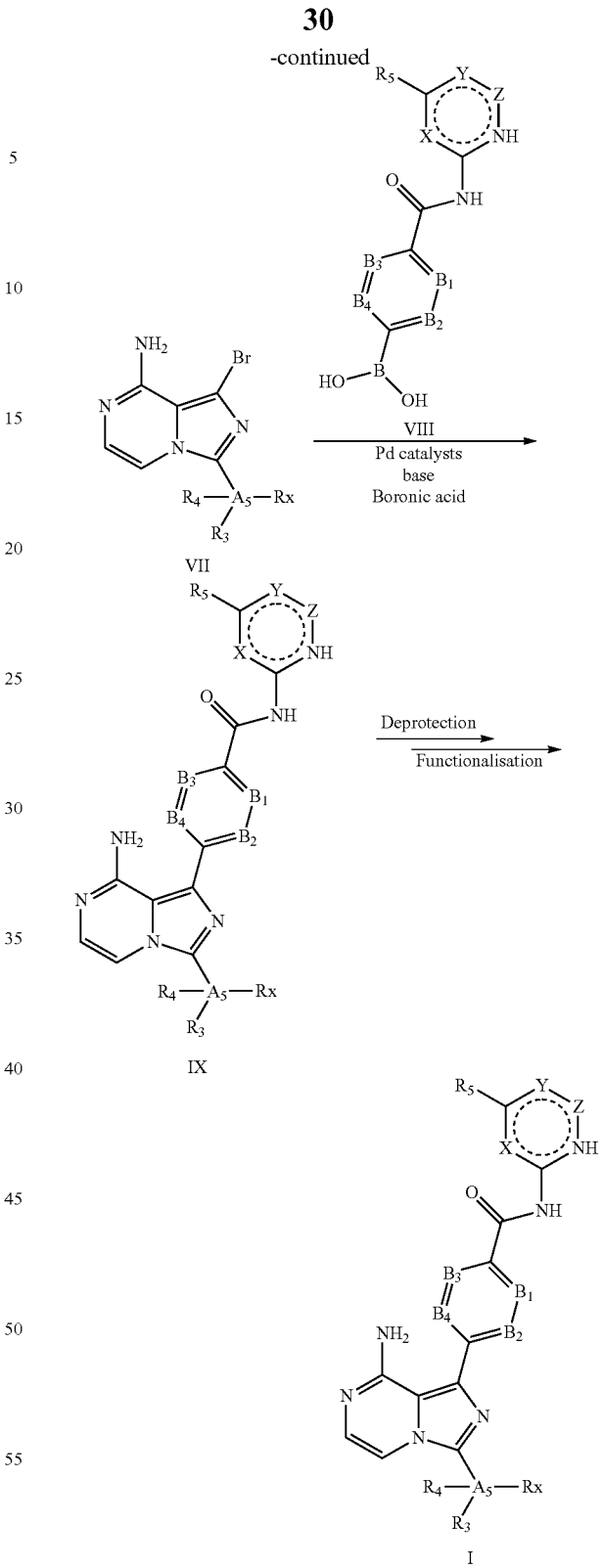

Reduction of 3-chloropyrazine-2-carbonitrile (II) can be accomplished by hydrogenation in the presence of a suitable catalyst system and solvent, for example Raney-Nickel to provide (3-chloropyrazin-2-yl)methanamine (III). This can then be reacted either with an appropriately amine protected amino acid where A5 is equivalent to CH and X is equivalent to OH. The reaction of HO(O)CC($R_3$,$R_4$)$R_x$ can be carried out in a solvent such as DMF, THF or DCM in the presence of a base such as DIPEA, N-methylmorpholine, 4-DMAP or triethylamine and in the presence of a coupling reagent such as PyBOP, TBTU, EDCI or HATU to form N-((3-chloropyrazin-2-yl)methyl)amide (IV). Alternatively, if A5 is equivalent to nitrogen, $NH(R_3,R_4)R_x$ can be activated with trichloromethyl chloroformate or phosgene to introduce COX, where X is equivalent to a leaving group. Subsequent reaction with (3-chloropyrazin-2-yl)methanamine (III) in a suitable solvent like DCM, EtOAc or DMF in the presence of a base such as DiPEA or triethylamine can give compounds of formula IV. Cyclisation chloropyrazine (IV) can be performed using condensation reagents like phosphorousoxychloride under heating conditions to provide the 8-chloroimidazo[1,5-a]pyrazine derivatives V. Subsequent bromination can be accomplished using bromine or N-bromosuccinimide in a suitable solvent like DCM or DMF at appropriate temperature to obtain compounds of formula VI. 8-Aminoimidazo[1,5-α]pyrazine derivatives (VII) can be prepared from compounds VI using ammonia(gas) in isopropanol at elevated temperature in a pressure vessel (>4 atm). Compounds of formula IX can be prepared from compounds of formula VII using an appropriate boronic acid or pinacol ester (VIII), in the presence of a suitable palladium catalyst system, for example bis(diphenylphosphino) ferrocene palladium(II)chloride complex or tetrakis(triphenylphosphine)palladium(0) in the presence of an anorganic base like potassium carbonate, cesium carbonate or potassium phosphate in a suitable solvent system like combinations of dioxane and water. Finally, cleaving the protective group of compounds with the formula IX give the unprotected amine or carboxylic acid which after functionalisation, using methods well known in the art, provided compounds of formula I.

The compounds like $COXA_5(R_3,R_4)R_x$ are either commercially available or they can be readily prepared using methods well known to the skilled organic chemist, to introduce protecting groups like benzyloxycarbonyl or tert-butyloxycarbonyl. Palladium catalysts and conditions to form either the pinacol esters or to couple the boronic acids or pinacol esters with the 1-bromoimidazo[1,5-a]pyrazin-8-amine are well known to the skilled organic chemist see, for example, Ei-ichi Negishi (Editor), Armin de Meijere (Associate Editor), Handbook of Organopalladium Chemistry for Organic Synthesis, John Wiley and Sons, 2002.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da. and scanned with a step rate of 0.2 Da. and the capillary voltage was set to 5000 V. $N_2$ gas was used for nebulisation.

LC-MS spectrometer (Waters) Detector: PDA (200-320 nm), Mass detector: ZQ and Eluent: A: acetonitrile with 0.05% trifluoroacetic acid, B: acetonitrile/water=1/9 (v/v) with 0.05% trifluoroacetic acid.

Method A: LC-MS

| Column | Ascentis Express C18, 100 × 3.0 mm, 2.7 µm |
| --- | --- |
| | A: $H_2O$ (0.1% TFA) |
| Mobile Phase | B: MeCN (0.05% TFA) |
| | Stop Time: 5.0 min |

| | Time (min) | B % |
| --- | --- | --- |
| Gradient | 0.00 | 10 |
| | 3.50 | 99 |
| | 4.99 | 99 |
| | 5.00 | 10 |
| Sample injection volume | 2 µl | |
| Flow Rate | 1.00 ml/min | |
| Wavelength | 220 nm | |
| Oven Tem. | 50° C. | |
| MS polarity | ESI POS | |

Method B: LC-MS

| Column | Ascentis Express C18, 50 × 2.1 mm, 5 µm |
| --- | --- |
| | A: $H_2O$ (0.1% TFA) |
| Mobile Phase | B: MeCN (0.05% TFA) |
| | Stop Time: 2.0 min |

| | Time (min) | B % |
| --- | --- | --- |
| Gradient | 0 | 10 |
| | 0.8 | 99 |
| | 1.99 | 99 |
| | 2.00 | 10 |
| Sample injection volume | 2 µl | |
| Flow Rate | 1.25 ml/min | |
| Wavelength | 220 nm | |
| Oven Temp. | 50° C. | |
| MS polarity | ESI POS | |

Method C:
Sample Info: Easy-Access Method: '1-Short_TFA_Fos'
Method Info: B222 Column Agilent SBC (3.0×50 mm, 1.8 µm); Flow 1.0 mL/min; solvent A: $H_2O$-0.1% TFA; solvent B: MeCN-0.1% TFA;
GRADIENT TABLE: 0 min:10% B, 0.3 min:10% B, 1.5 min:95% B, 2.70 min: 95% B, 2.76 min:10% B
stop time 3.60 min, PostTime 0.70 min.
Method D:
Sample Info: Easy-Access Method: '1_Fast'
Method Info: A330 Column Agilent Zorbax SB-C18 (2.1× 30 mm, 3.5 µm); Flow 2.0 mL/min;
solvent A: $H_2O$-0.1% TFA;
solvent B: MeCN-0.1% TFA;
GRADIENT TABLE: 0.01 min:10% B, 1.01 min:95% B, 1.37 min:95% B, 1.38 min:10% B, stop time 1.7 min, PostTime=OFF The following abbreviations are used throughout the application with respect to chemical terminology:
HATU O-(7-Azabenzotriazol-1-yl)-1,1,3,3-tetramethy luroniumhexafluoro phosphate
Cbz Benzyloxycarbonyl
D Deuterated hydrogen
DMF N,N-Dimethylformamide
DCM Dichloromethane
EA Ethyl acetate
EtOAc Ethyl acetate
DIPEA N,N-Diisopropylethylamine
THF Tetrahydrofuran
EtOH Ethanol EDCl.HCl 1-(3-Dimethylaminopropyl)-3-ethylcarbodiimide hydrochloride
4-DMAP 4-Dimethylaminopyridine
PyBOP O-Benzotriazole-1-yl-oxy-trispyrrolidinophosphoniumhexafluorophosphate
TBTU O-Benzotriazol-1-yl-N,N,N',N'-tetramethyluronium tetrafluoroborate
HBr Hydrogen bromide
HCl Hydrogen chloride
HOAc Acetic acid
POCl Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
$CO_2$ Carbondioxide
$NaHCO_3$ Sodium bicarbonate
$K_3PO_4$ Potassium phosphate
$P(Cy)_3$ Tricyclohexylphosphine
$Pd(OAc)_2$ Palladium(II) acetate
$Na_2SO_4$ Sodium sulfate
$Na_2CO_3$ Sodium carbonate
DAST Diethylaminosulfur trifluoride
$Cs_2CO_3$ Cesium carbonate
$Et_2O$ Diethylether
$Na_2S_2O_3$ Sodium thiosulfate
$Na_2S_2O_4$ Sodium hydrosulfite
$NaCNBH_3$ Sodium cyanoborohydride
$NH_4Cl$ Ammonium chloride
$MgSO_4$ Magnesium sulfate
LiOH Lithium hydroxide
IPA Isopropylamine
TFA Trifluoroacetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethylamine
CDI 1,1'-Carbonyl diimidazole
DMI 1,3-Dimethyl-2-imidazolidinone
NBS N-Bromosuccinimide
i-PrOH 2-Propanol
$K_2CO_3$ Potassium carbonate
$Pd(dppf)Cl_2$ 1,1'-Bis(diphenylphosphino)ferrocene palladium (II) chloride, complex withdichloromethane
$Et_3N$ Triethylamine
2-BuOH 2-Butanol
LCMS Liquid Chromatography/Mass Spectrometry
MeCN Acetonitrile
$NH_3$ Ammonia
$CD_3I$ Trideuteromethyl iodide
$CD_3OD$ Tetradeuteromethanol
$CH_3I$ Iodomethane
$CBr_4$ Carbon tetrabromide
Tris-HCl Tris(hydroxymethyl)aminomethane hydrochloride
$MgCl_2$ Magnesium chloride
$NaN_3$ Sodium azide
DTT Dithiothreitol
DMSO Dimethyl sulfoxide
IMAP Immobilized Metal Ion Affinity-Based Fluorescence Polarization
ATP Adenosine triphosphate
$MnCl_2$ Manganese(II) chloride
DMA Dimethylacetamide
IPA Isopropyl alcohol
TPP triphenylphosphine
DIAD Diisopropyl azodicarboxylate
DMB 2,4-dimethoxybenzyl
DCE Dichloroethane
DEAD Diethyl azodicarboxylate
ACN Acetonitrile
Ret. Time Retention Time
RT (rt) Room Temperature
Aq Aqueous
EtOH Ethanol
MPLC Medium Pressure Liquid Chromoatography
Xantphos 4,5-Bis(diphenylphosphino)-9,9-dimethylxanthene
X-phos 2-Dicyclohexylphosphino-2',4',6'-triisopropylbiphenyl Intermediate 1

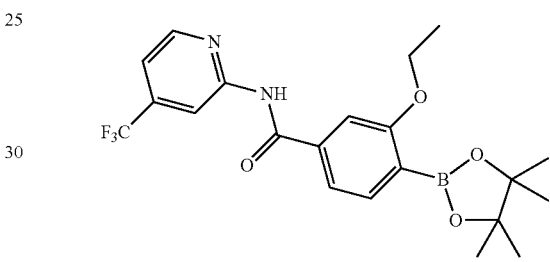

3-ethoxy-4-(4,4,5,5-tetramethyl-1,3,2-dioxaborolan-2-yl)-N-(4-(trifluoromethyl)pyridin-2-yl)benzamide Step 1: methyl 4-bromo-3-ethoxybenzoate A suspension of methyl 4-bromo-3-hydroxybenzoate (1.0 g, 4.33 mmol) and powder potassium carbonate (0.658 g, 4.76 mmol) in DMF (4.33 ml) under $N_2$ was treated with iodoethane (0.675 g, 4.33 mmol) via a syringe and the mixture stirred at rt for 2 h. The reaction was quenched with water and extracted with EtOAc (×2). The combined EtOAc layer was washed with water (×2) and brine, dried ($MgSO_4$) and concentrated to afford a white solid. Trituration with ether/hexane followed by filtration afforded the title compound as a solid. $^1$H NMR, 500 MHz, $CDCl_3$, δ7.62 (δ, J=8.2 Hz, 1H), 7.55 (d, J=1.7 Hz, 1H), 7.52 (dd, J=8.2, 1.8 Hz, 1H), 4.19 (q, J=6.9 Hz, 2H), 3.94 (s, 3H), 1.52 (t, J=7.0 Hz, 3H) ppm.

Step 2: 4-bromo-3-ethoxybenzoic acid

A solution of the title compound from step 1, methyl 4-bromo-3-ethoxybenzoate (900 mg, 3.47 mmol) in THF (9.0 ml) was treated with LiOH (166 mg, 6.95 mmol) dissolved in water (4.5 ml) followed by MeOH (4.5 ml). The resulting mixture was then stirred at 45° C. for 2 h. The solvent was evaporated and the residue diluted with water. The pH was adjusted to 6 with 2 N HCl and the resulting white suspension washed with EtOAc (×2). The organic

Step 3: 4-bromo-3-ethoxy-N-(4-(trifluoromethyl) pyridin-2-yl)benzamide

A suspension of the title compound from step 2, 4-bromo-3-ethoxybenzoic acid, (500 mg, 2.040 mmol), in DCM (5982 µl) under $N_2$ was treated with DMF (55.3µl, 0.714 mmol) followed by thionyl chloride (1489µl, 20.40 mmol) via a syringe and the mixture stirred at 35° C. for 18 h. The solvent was evaporated and the residue co-evaporated with DCM and toluene (×2). The resulting residue was then diluted with acetonitrile (5982₁11) and treated with DMAP (324 mg, 2.65 mmol) and 4-(trifluoromethyl)pyridin-2-amine (364 mg, 2.244 mmol). The mixture was then stirred at rt for 3 h. The solvent was evaporated and the residue diluted with
EtOAc and washed with water (×2). The combined organics was washed with brine, dried ($MgSO_4$) and concentrated. Purification on the CombiFlash RF MPLC, on a 40 g column, eluting with 0 to 20% EtOAc/Hexane (25 CV) affoded the title compound as a solid. Calc'd m/z=389.1, Found m/z=391.0 (M+2).

Step 4: 3-ethoxy-4-(4,4,5,5-tetramethyl-1,3,2-dioxaborolan-2-yl)-N-(4-(trifluoromethyl)pyridin-2-yl) benzamide A sealed vial containing the title compound from step 3, 4-bromo-3-ethoxy-N-(4-(trifluoromethyl)pyridin-2-yl)benzamide (500 mg, 1.285 mmol), 4,4,4',4',5,5,5',5'-octamethyl-2,2'-bi(1,3,2-dioxaborolane) (359 mg, 1.413 mmol), PdCl2 (dppf)-$CH_2Cl_2$ Adduct (210 mg, 0.257 mmol) and $K_3PO_4$ (252 mg, 2.57 mmol) was evacuated and backfilled with $N_2$. Dioxane (6424 µl) was then added via a syringe and the suspension evacuated again and backfilled with $N_2$. The mixture was then stirred at rt for 5 min and then at 75° C. for 4.0 h (dark mixture). The mixture was diluted with EtOAc and filtered. The filtrate was concentrated to afford a brown oil. Purification on the CombiFlash RF MPLC, on a 40 g column, eluting with 0 to 20% EtOAc/Hexane (40 CV) afforded the title compound, Intermediate 1. Calc'd m/z=436.2, Found m/z=437.1 (M+1).

Intermediate 2

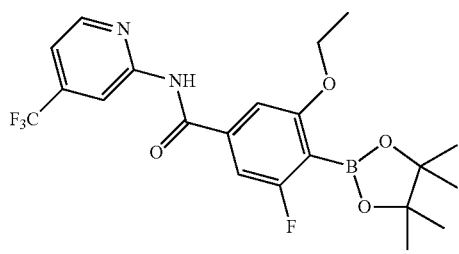 [SMILES: CCOc1cc(C(=O)Nc2cc(C(F)(F)F)ccn2)cc(F)c1B1OC(C)(C)C(C)(C)O1]

3-ethoxy-5-fluoro-4-(4,4,5,5-tetramethyl-1,3,2-dioxaborolan-2-yl)-N-(4-(trifluoromethyl)pyridin-2-yl) benzamide

Step 1: 3-Ethoxy-5-fluorobenzoic acid

SODIUM (6.54 g, 285 mmol) was dissolved in EtOH (150 ml) and concentrated to give a white solid. The solid was dissolved in DMSO (100 ml) and then added 3,5-difluorobenzoic acid (18 g, 114 mmol). The mixture was stirred at 80° C. for 12 hours. The mixture was cooled to room temperature and then the mixture was acided to ph=5 with 2M HCl, extracted with ethyl acetate (50 mL×3). The combined organic layers were washed with brine (20 mL), dried over anhydrous sodium sulfate, concentrated to afford the product 3-ethoxy-5-fluorobenzoic acid as a solid. 1H NMR (400 MHz, $CDCl_3$) δ=7.44-7.33 (m, 2H), 6.83 (d, J=10.2 Hz, 1H), 4.06 (q, J=7.0 Hz, 2H), 1.43 (t, J=7.0 Hz, 3H)

Step 2: 4-borono-3-ethoxy-5-fluorobenzoic acid

To a solution of 3-ethoxy-5-fluorobenzoic acid (4 g, 21.72 mmol) in THF (30 ml) was added LDA (32.6 ml, 65.2 mmol) dropwise at −78° C. under N2 atmosphere. The resultant solution was stirred for 15 min followed by slow addition of triisopropyl borate (4.90 g, 26.1 mmol). The mixture was stirred for 30 min and then hydrolyzed with 1M HCl. Extracted with EA (20 mL×3). The organic layer was washed with water (10 mL), brine (10 mL), dried over $Na_2SO_4$, concentrated to afford the crude product, then the crude product was pruified by column chromatography on silica gel eluted with (THF: PE=10%-100%) to give 4-borono-3-ethoxy-5-fluorobenzoic acid as a solid. The compound structure was confirmed by HMBC. $^1$H NMR (400 MHz, DMSO-$d_6$)=8.40 (s, 1H), 7.21 (s, 1H), 7.14 (d, J=7.8 Hz, 1H), 4.03 (q, J=7.0 Hz, 2H), 1.28 (t, J=6.8 Hz, 3H)

Step 3: 3-Ethoxy-5-fluoro-4-(4,4,5,5-tetramethyl-1, 3,2-dioxaborolan-2-yl)benzoic acid To a solution of 4-borono-3-ethoxy-5-fluorobenzoic acid (2.45 g, 10.75 mmol) in $PhCH_3$ (50 ml) was added 2,3-dimethylbutane-2,3-diol (1.397 g, 11.82 mmol) in one portion at room temperature under N2 atmosphere. The resultant solution was hitted to 120° C. and stirred at this temperature for 14 h. The mixture was cooled to room temperature and concentrated to afford the crude product, then the crude product was purified by column chromatography on silica gel eluted with (THF: PE=10%-50%) to give 3-ethoxy-5-fluoro-4-(4,4,5,5-tetramethyl-1,3,2-dioxaborolan-2-yl)benzoic acid as a solid. $^1$H NMR ($CDCl_3$)=7.34 (d, J=8.2 Hz, 1H), 7.29 (s, 1H), 4.07 (q, J=6.7 Hz, 2H), 1.46-1.31 (m, 15H)

Step 4: 3-Ethoxy-5-fluoro-4-(4,4,5,5-tetramethyl-1, 3,2-dioxaborolan-2-yl)-N-(4-(trifluoromethyl)pyridin-2-yl)benzamide To a solution of 3-ethoxy-5-fluoro-4-(4,4,5,5-tetramethyl-1,3,2-dioxaborolan-2-yl)benzoic acid (300 mg, 0.967 mmol) in anhydrous DCM (10 ml) was added OXALYL CHLORIDE (614 mg, 4.84 mmol) at 0° C., then DMF (one drop) was added and the mixture was stirred at 20° C. for 1.5 hrs. The mixture was concentrated in vacuo, which then diluted with THF (6 ml), to the mixture was added 4-(trifluoromethyl)pyridin-2-amine (314 mg, 1.935 mmol) at 0° C. The mixture was stirred at 80° C. for 16 hrs. After cooling to room temperature, the mixture was concentrated to give the crude product. The crude product was purified by column chromatography on silica gel eluted with (EA: PE=1%~50%) to give 3-ethoxy-5-fluoro-4-(4,4,5,5-tetramethyl-1,3,2-dioxaborolan-2-yl)-N-(4-(trifluoromethyl)pyridin-2-yl)benzamide as a solid. The compound structure was confirmed by NOE. $^1$H NMR (400 MHz, CHLOROFORMd)=8.71-8.66 (m, 2H), 8.47 (d, J=5.0 Hz, 1H), 7.31 (d, J=5.0 Hz, 1H), 7.18 (s, 1H), 7.12 (dd, J=0.9, 8.2 Hz, 1H), 4.10 (q, J=6.9 Hz, 2H), 1.46-1.38 (m, 15H)

Intermediate 3

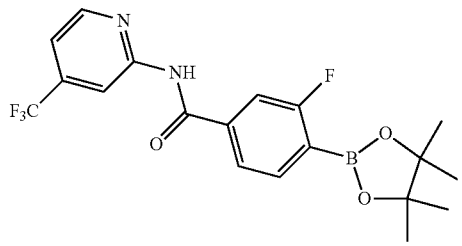 [SMILES: CC1(C)OB(c2ccc(C(=O)Nc3cc(C(F)(F)F)ccn3)cc2F)OC1(C)C]

3-fluoro-4-(4,4,5,5-tetramethyl-1,3,2-dioxaborolan-2-yl)-N-(4-(trifluoromethyl)pyridin-2-yl)benzamide 3-fluoro-4-(4,4,5,5-tetramethyl-1,3,2-dioxaborolan-2-yl)-N-(4-(trifluoromethyl)pyridin-2-yl)benzamide was prepared in a similar manner as intermediate 1

Intermediate 4

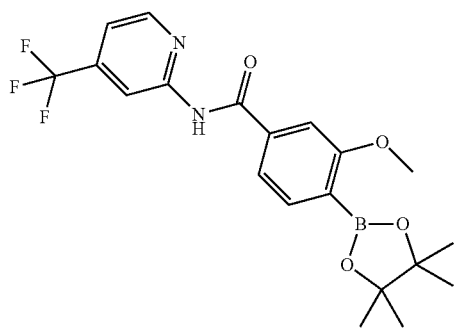 [SMILES: COc1cc(C(=O)Nc2cc(C(F)(F)F)ccn2)ccc1B1OC(C)(C)C(C)(C)O1]

3-methoxy-4-(4,4,5,5-tetramethyl-1,3,2-dioxaborolan-2-yl)-N-(4-(trifluoromethyl)pyridin-2-yl)benzamide 3-methoxy-4-(4,4,5,5-tetramethyl-1,3,2-dioxaborolan-2-yl)-N-(4-(trifluoromethyppyridin-2-yl)benzamide was prepared in a similar procedure as intermediate 1

Intermediate 5

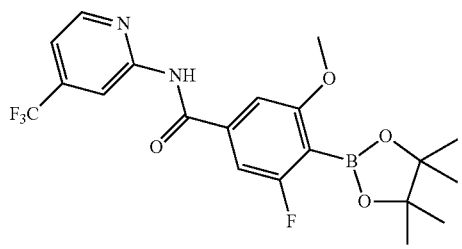 [SMILES: COc1cc(C(=O)Nc2cc(C(F)(F)F)ccn2)cc(F)c1B1OC(C)(C)C(C)(C)O1]

3-fluoro-5-methoxy-4-(4,4,5,5-tetramethyl-1,3,2-dioxaborolan-2-yl)-N-(4-(trifluoromethyl)pyridin-2-yl)benzamide 3-fluoro-5-methoxy-4-(4,4,5,5-tetramethyl-1,3,2-dioxaborolan-2-yl)-N-(4-(trifluoromethyl)pyridin-2-yl)benzamide was prepared in the similar method as intermediate 2

Intermediate 6

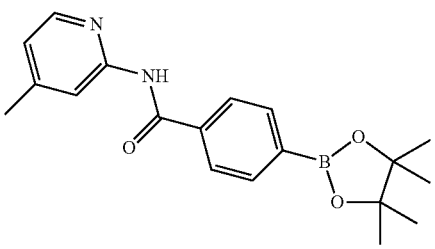

N-(4-methylpyridin-2-yl)-4-(4,4,5,5-tetramethyl-1,3,2-dioxaborolan-2-yl)benzamide N-(4-methylpyridin-2-yl)-4-(4,4,5,5-tetramethyl-1,3,2-dioxaborolan-2-yl)benzamide was prepared in a similar method as intermediate 1

Intermediate 7

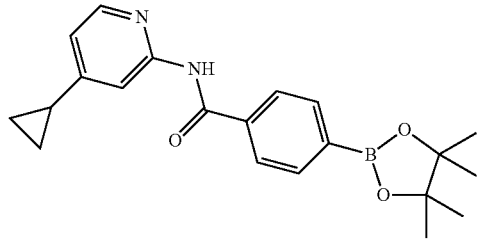 [SMILES: CC1(C)OB(c2ccc(C(=O)Nc3cc(C4CC4)ccn3)cc2)OC1(C)C]

N-(4-cyclopropylpyridin-2-yl)-4-(4,4,5,5-tetramethyl-1,3,2-dioxaborolan-2-yl)benzamide N-(4-cyclopropylpyridin-2-yl)-4-(4,4,5,5-tetramethyl-1,3,2-dioxaborolan-2-yl)benzamide was prepared in a similar method as intermediate 1

Intermediate 8

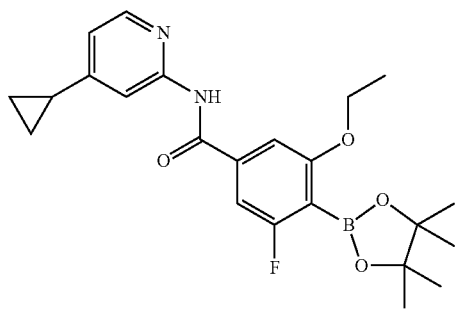 [SMILES: CCOc1cc(C(=O)Nc2cc(C3CC3)ccn2)cc(F)c1B1OC(C)(C)C(C)(C)O1]

N-(4-cyclopropylpyridin-2-yl)-3-ethoxy-5-fluoro-4-(4,4,5,5-tetramethyl-1,3,2-dioxaborolan-2-yl)benzamide N-(4-cyclopropylpyridin-2-yl)-3-ethoxy-5-fluoro-4-(4,4,5,5-tetramethyl-1,3,2-dioxaborolan-2-yl)benzamide was prepared in a similar method as intermediate 2

Intermediate 9

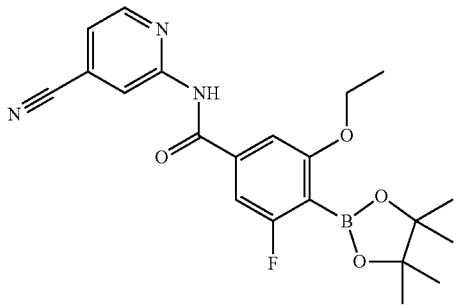 [SMILES: CCOc1cc(C(=O)Nc2cc(C#N)ccn2)cc(F)c1B1OC(C)(C)C(C)(C)O1]

N-(4-cyanopyridin-2-yl)-3-ethoxy-5-fluoro-4-(4,4,5,5-tetramethyl-1,3,2-dioxaborolan-2-yl)benzamide N-(4-cyanopyridin-2-yl)-3-ethoxy-5-fluoro-4-(4,4,5,5-tetramethyl-1,3,2-dioxaborolan-2-yl)benzamide was prepared in a similar method as intermediate 2

Intermediate 10

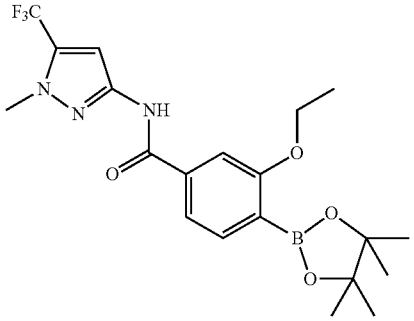

3-ethoxy-N-(1-methyl-5-(trifluoromethyl)-1H-pyrazol-3-yl)-4-(4,4,5,5-tetramethyl-1,3,2-dioxaborolan-2-yl)benzamide

Step 1: 4-bromo-3-ethoxy-N-(1-methyl-5-(trifluoromethyl)-1H-pyrazol-3-yl)benzamide A solution of 4-bromo-3-ethoxybenzoic acid (5.0 g, 20.40 mmol) in DMF (102 ml) was treated with HATU (8.53 g, 22.44 mmol) and the mixture stirred at rt for 15 min. 1-methyl-5-(trifluoromethyl)-1H-pyrazol-3-amine (3.37 g, 20.40 mmol) was then added followed by DIEA (7.13 ml, 40.8 mmol) and the mixture stirred at rt for 15 h. The mixture was diluted with EtOAc and washed with water (×2). The organic layer was then washed with brine, dried (MgSO$_4$) and concentrated to afford an oil. Purification on the CombiFlash RF MPLC on a 24 g column, eluting with 0 to 20% EtOAc/Hexane afforded the desired product as an oil which later solidified. Calc'd m/z=392.1, Found m/z=394.0 (M+2).

Step 2: 3-ethoxy-N-(1-methyl-5-(trifluoromethyl)-1H-pyrazol-3-yl)-4-(4,4,5,5-tetramethyl-1,3,2-dioxaborolan-2-yl)benzamide In a sealed round bottom flask containing the title compound from step 1, 4-bromo-3-ethoxy-N-(1-methyl-5-(trifluoromethyl)-1H-pyrazol-3-yl)benzamide, (1000 mg, 2.55 mmol), 4,4,4',4',5,5,5',5'-octamethyl-2,2'-bi(1,3,2-dioxaborolane) (971 mg, 3.82 mmol), PdCl2(dppf)-CH$_2$Cl$_2$ adduct (208 mg, 0.255 mmol) and potassium acetate (751 mg, 7.65 mmol) was added 1,4-Dioxane (1.27E+04 µl) under a N$_2$ atmosphere. The resulting suspension was then degassed (×3) and back filled with N$_2$. The mixture was then stirred at 80° C. under N$_2$ for 8 h h. The mixture was filtered and the filtrate concentrated. Purification on the CombiFlash RF, on a 80 g column, eluting with 0 to 15% EtOac/Hexane (80 CV) afforded the title compound, Intermediate 30 as an oil which later solidified. Calc'd m/z=439.2, Found m/z=440.2 (M+1).

Intermediate 11

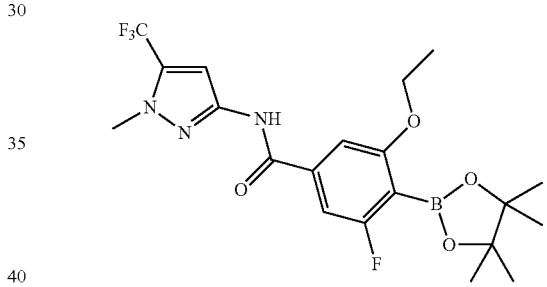

3-ethoxy-5-fluoro-N-(1-methyl-5-(trifluoromethyl)-1H-pyrazol-3-yl)-4-(4,4,5,5-tetramethyl-1,3,2-dioxaborolan-2-yl)benzamide 3-ethoxy-5-fluoro-N-(1-methyl-5-(trifluoromethyl)-1H-pyrazol-3-yl)-4-(4,4,5,5-tetramethyl-1,3,2-dioxaborolan-2-yl)benzamide was prepared in a similar method as intermediate 2 and 10

Intermediate 12

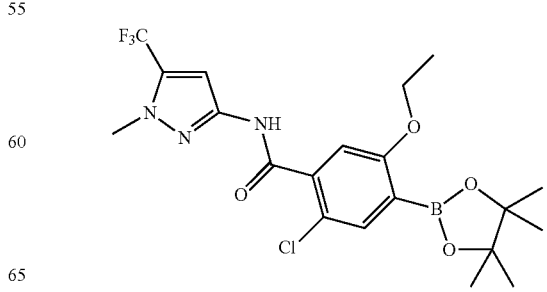

2-chloro-5-ethoxy-N-(1-methyl-5-(trifluoromethyl)-1H-pyrazol-3-yl)-4-(4,4,5,5-tetramethyl-1,3,2-dioxaborolan-2-yl)benzamide Step 1

Added a solution of Iodine (0.75 g, 2.95 mmol) and potassium iodide (0.55 g, 3.31 mmol) in water (5 ml) dropwise to a solution of 2-Chloro-5-hydroxybenzoic acid (0.5 g, 2.90 mmol) in ammonium hydroxide (conc, 4 ml, 48 mmol) then stirred 2 hours at room temperature. Reaction was diluted with water (5 ml) acidified to pH 3 with conc. HCl, then extracted with EtOAc (50 ml) and H$_2$O (20 ml). Organic layer was separated, dried over Na$_2$SO$_4$, then filtered and evaporated solvent yielding 2-Chloro-5-hydroxy-4-iodobenzoic acid as a solid LCMS: C7H4ClIO3 MH Found [M+H]+:298.84 RT=1.26 min.

Step 2

Added Thionyl Chloride (0.5 ml, 6.85 mmol) dropwise to a solution of 2-Chloro-5-Hydroxy-4-iodobenzoic acid (0.6 g, 2.01 mmol) in MeOH (10 ml) at 0° C., then stirred overnight at room temperature. The solvent was evaporated and residue extracted with EtOAc (100 ml), washed with saturated NaHCO$_3$ (40 ml), dried over Na$_2$SO$_4$ then filtered and solvent evaporated yielding the title compound Methyl-2-Chloro-5-hydroxy-4-iodobenzoate as a solid.

Step 3

Added Iodoethane (0.3 ml, 3.75 mmol) to a suspension of Methyl-2-Chloro-5-hydroxy-4-iodobenzoate (0.9 g, 2.87 mmol) and potassium carbonate (0.4 g, 2.89 mmol) in DMF (4 ml) then stirrede 2 hours at room temperature. Extracted with EtOAc (100 ml) and H$_2$O (40 ml), separated organic layer, dried over Na$_2$SO$_4$, then filtered and evaporated solvent. Purified by chromatography (40 g silica gel, 20% ethylacetate in Hexanes) yielding title compound Methyl-2-Chloro-5-Ethoxy-4-Iodobenzoate as a solid.

LCMS: C10H10ClIO3, Found [M+H]+340.89, RT=1.56 min.

Step 4

Added Lithium Hydroxide monohydrate (0.2 g, 4.77 mmol) to a solution of Methyl-2-Chloro-5-Ethoxy-4-Iodobenzoate (0.3 g, 0.846 mmol) in Methanol:THF:H$_2$O (7 ml, 3:3:1) then stirred at 40° C. overnight. Reaction was cooled to room temperature, the solvent was evaporated, and residue was diluted with H$_2$O (20 ml), acidified with conc HCl to pH 3, precipitated white solid was filtered and washed with H$_2$O (10 ml). Solid was dissolved in THF (20 ml) and solvent evaporated yielding title compound 2-Chloro-5-Ethoxy-4-Iodobenzoic acid.

Step 5

Added oxalyl chloride (0.3 ml, 3.16 mmol) to solution of 2-Chloro-5-Ethoxy-4-Iodobenzoic acid (0.3 g, 1.101 mmol) and DMF (0.05 ml, 3.16 mmol) in MeCl$_2$ (10 ml) then stirred at room temperature for 1 hour.

Solvent was evaporated, yielding the title compound 2-Chloro-5-Ethoxy-4-Iodobenzoyl chloride as a solid.

Step 6

Added DMAP (3 mg, 0.025 mmol) and N-Ethyl-N-isopropylpropan-2-amine (0.2 ml, 1.148 mmol) to mixture of 2-Chloro-5-Ethoxy-4-Iodobenzoyl chloride (0.27 g, 0.783 mmol) and 1-Methyl-5-trifluoromethyl-1H-Pyrazol-3-amine (150 mg, 0.908 mmol) in THF (3 ml) then stirred at room temperature for 2 hours. Extracted with EtOAc (50 ml) and H$_2$O (20 ml), then separated organic layer, dried over Na$_2$SO$_4$, then filtered and evaporated solvent. Purified residue by chromatography (24 g silica gel, 15% ethylacetate in Hexanes) yielding title compound 2-Chloro-5-Ethoxy-4-Iodo-N-(1-Methyl-5-(trifluoromethyl)-1H-pyrazol-3-yl) benzamide as a solid.

LCMS: C14H12ClF3IN3O2, Found [M+H]+473.96, RT=1.53 min.

Step 7

Added DMSO (1 ml) to a mixture of Bis(Pinacolato)Diboron (160 mg, 0.630 mmol), potassium acetate (80 mg, 0.815 mmol); [1,1'-Bis(Diphenylphosphino)ferrocene]Dichloropalladium (11) (20 mg,0.027 mmol) and 2-Chloro-5-Ethoxy-4-Iodo-N-(1-Methyl-5-(trifluoromethyl)-1H-pyrazol-3-yl) benzamide (200 mg,0.422 mmol), degassed resultant solution, then stirred at 80° C. for 4 hours. Cooled to room temperature, then extracted with EtOAc (50 ml) and H$_2$O (20 ml). Separated organic layer dried over Na$_2$SO$_4$, then filtered and evaporated solvent. Purified residue by chromatography (24 g silica gel, 45% ethylacetate in Hexanes) yielding title compound 2-chloro-5-ethoxy-N-(1-methyl-5-(trifluoromethyl)-1H-pyrazol-3-yl)-4-(4,4,5-trimethyl-1,3,2-dioxaborolan-2-yl)benzamide) as a solid.

LCMS: C14H12ClF3N3O2, Found [M+H]+474.12, RT=1.55 min.

Intermediate 13

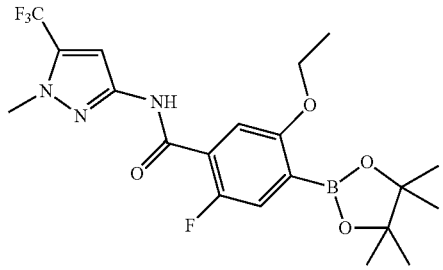

5-ethoxy-2-fluoro-N-(1-methyl-5-(trifluoromethyl)-1H-pyrazol-3-yl)-4-(4,4,5,5-tetramethyl-1,3,2-dioxaborolan-2-yl)benzamide The title compound was prepared in a similar method as Intermediate 12

Intermediate 14

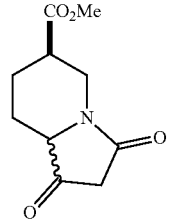 [SMILES: COC(=O)[C@@H]1CCC2C(=O)CC(=O)N2C1]

Methyl 1,3-dioxooctahydroindolizine-6-carboxylate

Step 1, Preparation of (cis)-dimethyl piperidine-2,5-dicarboxylate

To dimethyl pyridine-2,5-dicarboxylate (50 g) was added AcOH (500 mL) and catalyst 5% Rh/Al$_2$O$_3$ (5 g). The reaction mixture was shaked under H2 (100 psi) at 25° C. for 16 h. The catalyst was removed by filtration. The AcOH was removed under vacuum and the residue was used without further purification.

Step 2, Preparation of (cis)-dimethyl 1-(4-methoxy-3,4-dioxobutanoyl)piperidine-2,5-dicarboxylate (cis)-Dimethyl piperidine-2,5-dicarboxylate acetate (147 g, 563 mmol) was dissolved in $CH_2Cl_2$ (1407 ml) in a 3 L three-neck round bottom flask with a machine stir, an temperature probe and an additional funnel. The flask was cooled by a ice-water bath. Methyl malonyl chloride (91 ml, 844 mmol) was added slowly via an additional funnel in a speed that the internal temperature was maintained at below 10° C. After the additional was completed, the reaction mixture was stirred in the ice-water bath for 3 hours. Sat $NaHCO_3$ was added slowly with efficient stirring. The pH value of the reaction mixture was checked by pH paper. After 500 mL sat NaHCO3 was added, solid NaHCO3 was added into the solution mixture with efficient stirring, until the pH value of the reaction mixture reaches 8 to 9. The DCM layer was separated and the aquous layer was extracted with DCM (300 ml) twice. The organic laayers were combined and concentrated. It was dried under vacuum with stirring to give the title compound as a oil. It was used without further purification.

Step 3, Preparation of sodium 2,6-bis(methoxycarbonyl)-3-oxo-3,5,6,7,8,8a-hexahydroindolizin-1-olate To (cis)-dimethyl 1-(3-methoxy-3-oxopropanoyl)piperidine-2,5-dicarboxylate (136.75 g, 454 mmol) in a 2 L round bottom flask was added MeOH (648 ml). It was cooled by a ice-water bath. NaOMe (85 ml, 454 mmol) was added dropwise via an additional funnel over 30 minutes. The internal temperature was kept between 6 to 8° C. White solid appeared during this time period. MTBE (800 mL) was added over 45 min via an additional funnel. The slurry was stirred at 0° C. for 2 h and filtered, washed with MTBE twice, and dried under vacuum for 3 days to give the title compound as a solid.

Step 4, Preparation of Dimethyl 1,3-dioxooctahydroindolizine-2,6-dicarboxylate

Sodium 2,6-bis(methoxycarbonyl)-3-oxo-3,5,6,7,8,8a-hexahydroindolizin-1-olate (32.8 g, 113 mmol) was suspended in DCM (282 ml). HCl (282 ml, 563 mmol) was added. The suspension was stirred at 25° C. for 20 min until all solid dissolved. The mixture was transfered into a separate funnel and the organic layer was separated. The aquous layer was extracted with DCM (150 mL) twice. The organic layers were combined, concentrated, and dried under vacuum for 3 hours to give the title compound as a solid.

Step 5, Preparation of Methyl 1,3-dioxooctahydroindolizine-6-carboxylate

To a 500 mL round bottom flask was added dimethyl 1-hydroxy-3-oxo-3,5,6,7,8,8a-hexahydroindolizine-2,6-dicarboxylate (5.26 g, 19.54 mmol), acetic acid (98 ml) and water (0.704 ml, 39.1 mmol). The reaction was stirred at 70° C. for 2.5 hours. The acetic acid was removed at 25° C. under vacuum. It was azotropied with Toluene (100 mL) twice to give the title compound as a oil which was stored at −20° C. MS: 212.13 [M+H]+

Intermediate 15

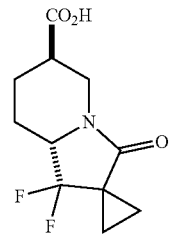 [SMILES: O=C(O)[C@@H]1CC[C@@H]2N(C1)C(=O)C1(CC1)C2(F)F]

(trans)-1',1'-difluoro-3'-oxohexahydro-1'H-1-spiro[cyclopropane-1,2'-indolizine]-6'-carboxylic acid Step 1. Preparation of Methyl 1',3'-dioxohexahydro-1'H-spiro[cyclopropane-1,2'-indolizine]-6'-carboxylate To a 500 mL round bottom flask was added tert-Butanol (191 ml), $K_2CO_3$ (22.31 g, 161 mmol) and 1,2-dibromomethane (11.13 ml, 129 mmol). The temperature of the reaction mixture was raised to 70° C. (a temperature probe was placed in the reaction mixture, heating mantle temperature is 74° C.). Methyl 1,3-dioxooctahydroindolizine-6-carboxylate (6.82 g, 32.3 mmol) was dissolved in DMF (23.92 ml) and it was added into the reaction solution over a period of 24 h via a syringe pump at 70° C. The reaction mixture was concentrated to almost dry. The DMF was removed as much as possible. Then 200 mL water and 200 mL DCM was added. The aqueous layer was separated and extracted with DCM (100 ml) once. The organic layers were combined and then washed with water (100 mL) three times, dried over anhydrous $Na_2SO_4$, concentared and purified by $SiO_2$ chromatography (Hexane/EtOAc, 20% to 100%) to give the title compounds as oil. MS: 238.07 [M+H]+

Step 2. Preparation of Methyl 1',1'-difluoro-3'-oxohexahydro-1'H-spiro[cyclopropane-1,2'-indolizine]-6'-carboxylate To a 40 mL pressure vial with pressure release cap was added Methyl 1',3'-dioxohexahydro-1'H-spiro[cyclopropane-1,2'-indolizine]-6'-carboxylate (350 mg, 1.475 mmol) and bis(2-methoxylaminosulfurtrifluoride (6337 μl, 14.75 mmol). The reaction was stirred at 90° C. for 8 h. More DeoxoFluor (2 ml) was added and the reaction was stirred at 90° C. for another 16 hours. The reaction was cooled down and sat $NaHCO_3$ was added carefully until no bubble cames out. The product was extracted with EtOAc three times. The organic layers were combined, washed with brine once, dried over anhydrous $Na_2SO_4$, filtered, and concentrated. The product was purified by $SiO_2$ chromatography (Hexane/EtOAc, 0% to 100%) to give the title compound. MS: 260.14 [M+H]+

Step 3. Preparation of (trans)-1',1'-difluoro-3'-oxohexahydro-1'H-spiro[cyclopropane-1,2'-indolizine]-6'-carboxylic acid To a 40 mL round bottom flask was added methyl 1',1'-difluoro-3'-oxohexahydro-1'H-spiro[cyclopropane-1,2'-indolizine]-6'-carboxylate (235 mg, 0.906 mmol), MeOH (4532 µl), and NaOMe (196 mg, 3.63 mmol). Then water (32.7 µl, 1.813 mmol) was added. The solution was stirred at 70° C. for 24 hours. More NaOMe (196 mg, 3.63 mmol) and water (32.7 µl, 1.813 mmol) were added at 70° C. The reaction was stirred at 70° C. for another 24 h. After the reaction was cooled down, AcOH (about 5 equive) was added until the solution is slightly acidic. The solid was collected by filtration and washed with small amount of water twice. This is the first batch of the title compound. The filtrate was concentrate to about 15 mL and applied to the C18 column. The product was purified by C18 column (CH₃CN in water with 0.1% TFA: 0% to 30%) to give the batch of the title compound. MS: 246.11 [M+H]+

Intermediate 16

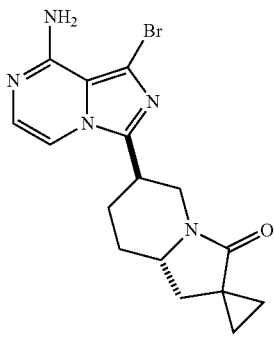

(trans)-6'-(1-bromo-8-((2,4-dimethoxybenzyl)amino) imidazo[1,5-a]pyrazin-3-yl)tetrahydro-1'H-spiro [cyclopropane-1,2'-indolizin]-3'(5'H)-one Step 1. Preparation of (trans)-6'-(1-bromo-8-((2,4-dimethoxybenzyl)amino)imidazo[1,5-a]pyrazin-3-yl)-1'-hydroxytetrahydro-1'H-spiro[cyclopropane-1, 2'-indolizin]-3'(5'H)-one To a 100 mL pressure vial with pressure release cap was added 6'-(1-bromo-8-((2,4-dimethoxybenzyl)amino)imidazo[1,5-a]pyrazin-3-yl)tetrahydro-1'H-spiro[cyclopropane-1,2'-indolizine]-1',3'(5'H)-dione (550 mg, 1.018 mmol), EtOH (1.02E+04 µl), and sodium borohydride (77 mg, 2.035 mmol). The reaction was stirred at 25° C. for 2 hours. Sat NaHCO₃ was added until no bubble comes out. Then the reaction was extracted with DCM (50 mL×3). The organic layers were combined and concentrated. The product was purified by SiO₂ chromatography (EtOAc/EtOH (3:1) in hexane with 1% NH₃.H₂O, 0% to 100%) to give the title compound. MS: 541.84, 543.84 [M+H]+

Step 2. Preparation of O-(trans)-6'-(1-bromo-8-((2, 4-dimethoxybenzyl)amino)imidazo[1,5-a]pyrazin-3-yl)-3'-oxohexahydro-1'H-spiro[cyclopropane-1,2'-indolizin]-1'-yl) 1H-imidazole-1-carbothioate To a 8 mL pressure vial with pressure release cap was added (trans)-6'-(1-bromo-8-((2,4-dimethoxybenzyl)amino) imidazo[1,5-a]pyrazin-3-yl)-1'-hydroxytetrahydro-1'H-spiro[cyclopropane-1,2'-indolizin]-3'(5'H)-one (300 mg, 0.553 mmol), 1,1'-thiocarbonyldiimidazole (246 mg, 1.383 mmol) and THF (5531 µl). The reaction was stirred at reflux for 3 hours. LCMS indicated about 40% SM remain. More thiocarbonyldiimidazole (100 mg) was added and the reaction was stirred at reflux for another 2 hours. Saturated NaHCO₃ (50 mL) and DCM (50 mL) were added. The organic layer was separated and concentrated. The product was purified by SiO₂ chromatography (EtOAc/EtOH (3:1) in hexane with 1% NH₃.H₂O, 0% to 100%) to give the title compound. MS: 652.12, 654.12 [M+H]+

Step 3. Preparation of (trans)-6'-(1-bromo-8-((2,4-dimethoxybenzyl)amino)imidazo[1,5-a]pyrazin-3-yl) tetrahydro-1'H-spiro[cyclopropane-1,2'-indolizin]-3' (5'H)-one To a 40 mL pressure vial with pressure release cap was added tri-n-butyltinhydride (246 µl, 0.919 mmol) and toluene (2043 µl). The solution was heated to 115° C. O-((trans)-6'-(1-bromo-8-((2,4-dimethoxybenzypamino)imidazo[1,5-a]pyrazin-3-yl)-3'-oxohexahydro-1'H-spiro[cyclopropane-1, 2'-indolizin]-1'-yl) 1H-imidazole-1-carbothioate (300 mg, 0.460 mmol) was dissolved in toluene (4086 µl) and added into the solution dropwise and slowly. The reaction was stirred at 115° C. for 4 hours. The solvent was concentrated and the residue was purified by C18 column (Gilson, CH₃CN in water with 0.1% TFA: 0% to 90%) to give the title compound. MS: 526.07, 528.07 [M+H]+

Intermediate 17

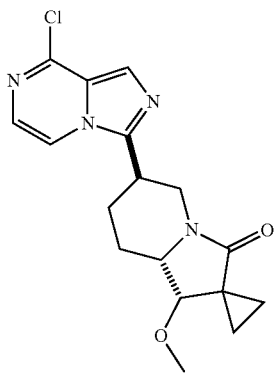

trans-6'-(8-chloroimidazo[1,5-a]pyrazin-3-yl)-1'-methoxytetrahydro-1'H-spiro[cyclopropane-1,2'-indolizin]-3'(5'H)-one Step 1, trans-N-((3-chloropyrazin-2-yl)methyl)-1',3'-dioxohexahydro-1'H-spiro[cyclopropane-1,2'-indolizine]-6'-carboxamide To the heterogeneous potassium superoxide (468 mg, 6.58 mmol) and trans-N-((3-chloropyrazin-2-yl)methyl)-3'-oxo-1'-(2-tosylhydrazono)hexahydro-1'H-spiro[cyclopropane-1, 2'-indolizine]-6'-carboxamide (340 mg, 0.658 mmol) solution in acetonitrile was added a solution of 2-nitrobenzene-1-sulfonyl chloride (437 mg, 1.973 mmol) in acetonitrile (6 mL) at −42° C. under nitrogen atmosphere with good stirring for 20 hours. The reaction mixture was then filtered, washed with acetonitrile and DCM and concentrated under vacuum to give a crude residue, which was column purified on silica gel eluting with (30-70% EtOAc/Hexanes) solvent system to afford trans-N-((3-chloropyrazin-2-yl)methyl)-1',3'-dioxohexahydro-1'H-spiro[cyclopropane-1,2'-indolizine]-6'-carboxamide. [M+H]+=349.07, Rt=1.02 mins method B.

Step 2, trans-6'-(8-chloroimidazo[1,5-a]pyrazin-3-yl)tetrahydro-1'H-spiro[cyclopropane-1,2'-indolizine]-1',3'(5'H)-dione trans-N-((3-chloropyrazin-2-yl)methyl)-1',3'-dioxohexahydro-1'H-spiro[cyclopropane-1,2'-indolizine]-6'-carboxamide (140 mg, 0.401 mmol) was dissolved in acetonitrile (6 mL) and DMF (0.2 mL) and cooled to 0° C. Phosphoryl trichloride (0.128 ml, 1.405 mmol) was added slowly at 0° C. The ice bath was removed and reaction mixture was stirred at 40° C. for 30 mins under a stream of nitrogen. Upon completion, the reaction mixture was cooled to 0° C. and quenched with saturated NaHCO$_3$, and extracted with DCM (3× 15 ml). The combined organic phases were concentrated to dryness and the residue was column purified (3% MeOH/DCM) to afford trans-6'-(8-chloroimidazo[1,5-a]pyrazin-3-yl)tetrahydro-1'H-spiro[cyclopropane-1,2'-indolizine]-1',3'(5'H)-dione. [M+H]$^+$=331.04, Rt=1.16 mins, method B.

Step 3, trans-6'-(8-chloroimidazo[1,5-a]pyrazin-3-yl)-1'-hydroxytetrahydro-1'H-spiro[cyclopropane-1,2'-indolizin]-3'(5'H)-one To a 25 mL round bottom flask was added trans-6'-(8-chloroimidazo[1,5-a]pyrazin-3-yl)tetrahydro-1'H-spiro[cyclopropane-1,2'-indolizine]-1',3'(5'H)-dione (100 mg, 0.302 mmol), Ethanol (6 ml), and sodium tetrahydroborate (28.6 mg, 0.756 mmol). The reaction was stirred at RT for 1 hour. The mixture was concentrated under vacuum to give a crude residue, which was column purified on silica gel eluting with (30-60% EtOAc/Hexane) to afford trans-6'-(8-chloroimidazo[1,5-a]pyrazin-3-yl)-1'-hydroxytetrahydro-1'H-spiro[cyclopropane-1,2'-indolizin]-3'(5'H)-one. [M+H]+=333.08, Rt=1.05 mins, method B.

Step 4, trans-6'-(8-chloroimidazo[1,5-a]pyrazin-3-yl)-1'-methoxytetrahydro-1'H-spiro[cyclopropane-1,2'-indolizin]-3'(5'H)-one To trans-6'-(8-chloroimidazo[1,5-a]pyrazin-3-yl)-1'-hydroxytetrahydro-1'H-spiro[cyclopropane-1,2'-indolizin]-3'(5'H)-one (50 mg, 0.150 mmol) dissolved in DMF (2 mL) at 0° C. was added sodium hydride (10.82 mg, 0.451 mmol) and stirred for 30 minutes under constant flow of nitrogen. Iodomethane (25.6 mg, 0.180 mmol) was added and continued to stir for overnight. The reaction was quenched with saturated NH4Cl and extracted with EtOAc (3×5 mL). The combined organic phase was washed with saturated NaCl (1×5 mL) and concentrated under vacuum to give a crude product trans-6'-(8-chloroimidazo[1,5-a]pyrazin-3-yl)-1'-methoxytetrahydro-1'H-spiro[cyclopropane-1,2'-indolizin]-3'(5'H)-one. [M+H]+=347.02, Rt=1.22 mins, method B.

Intermediate 18

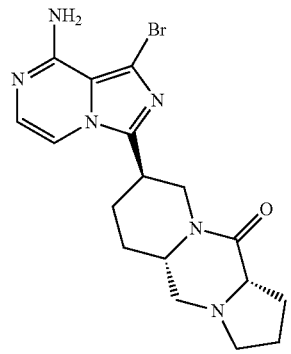

(5aS,8R,11aS)-8-(8-amino-1-bromoimidazo[1,5-a]pyrazin-3-yl)octahydro-1H-pyrido[1,2-a]pyrrolo[1,2-d]pyrazin-11(11aH)-one Step 1. Dimethyl pyridine-2,5-dicarboxylate SOCl$_2$ (855 g, 7.2 mol) was added dropwise into the solution of pyridine-2,5-dicarboxylate (500 g, 3.0 mol) in MeOH (5 L) at room temperature. The mixture was stirred at 70° C. overnight. After cooling, the mixture was evaporated, and the residue was added EA (5 L), followed by Na$_2$CO$_3$ (sat.) until PH>7. The mixture was separated and the aqueous layer was extracted with EA (1 L*3). The combined organic layer was washed with brine, dried over Na$_2$SO$_4$, filtered and concentrated to give dimethyl pyridine-2,5-dicarboxylate. The product was used for next step without further purification.

Step 2. Methyl 6-(hydroxymethyl)nicotinate

The mixture of dimethyl pyridine-2,5-dicarboxylate (200 g, 1.03 mol) in MeOH (2400 ml) and THF (2200 ml) was added CaCl$_2$ (455 g, 4.10 mol) and NaBH$_4$ (97 g, 2.56 mol) below −10° C. The mixture was stirred below 0° C. for 3 hours. The mixture was added NH$_4$Cl (15%, 2000 ml), and the temperature maintain below 5° C. Then, the solution was extracted with EA (500 ml×3). The combined organic layers were dried over Na$_2$SO$_4$, filtered and concentrated to give the crude product. The crude product was washed with PE:DCM=5:1 to give methyl 6-(hydroxymethyl) nicotinate as a solid. $^1$H NMR: 400 MHz CDCl$_3$: δ8.052 (s, 1H), 8.315~8.290 (m, 1H), 7.381~7.359 (m, 1H), 4.845 (s, 2H), 3.969 (s, 3H) ppm.

Step 3. Methyl 6-(acetoxymethyl)nicotinate

The mixture of methyl 6-(hydroxymethyl) nicotinate (620 g, 3.7 mol) in DCM (6000 ml) was added Et$_3$N (937 g, 9.3 mol), DMAP (31 g, 5%) and Ac$_2$O (571 g, 5.5 mol). The mixture was stirred at room temperature for 3 hours. The mixture was added H$_2$O (5000 ml), separated and the aqueous layer was extracted with DCM (1500 ml*3). The combined organic layers were dried over Na$_2$SO$_4$ and concentrated to give the crude product. The crude product was washed with PE:EA=5:1 to give methyl 6-(acetoxymethyl) piperidine-3-carboxylate as a solid. $^1$H NMR: 400 MHz CDCl$_3$ δ: 9.209~9.205 (s, 1H), 8.347~8.322 (m, 1H), 7.469~7.449 (d, J=8 Hz, 1H), 5.305 (s, 2H), 3.984 (s, 3H), 2.218 (s, 3H), 3.565~3.465 (m, 2H), 2.135~1.878 (m, 2H) ppm.

Step 4. Methyl 6-(acetoxymethyl)piperidine-3-carboxylate $NaBH_3CN$ (136 g, 2.15 mol) was added in portions to the solution of methyl 6-(acetoxymethyl)piperidine-3-carboxylate (100 g, 0.48 mol) in $CH_3COOH$ (500 ml) at 0° C. for 2 hours and the mixture was stirred at 30° C. for 2 hours, quenched with $H_2O$ (120 ml), evaporated in vacuum to give methyl 6-(acetoxymethyl)piperidine-3-carboxylate as an oil, which was directly used for next step without further purification. LCMS: (M+1=216.2).

Step 5. trans-1-benzyl 3-methyl 6-(acetoxymethyl)piperidine-1,3-dicarboxylate $NaHCO_3$ (67.2 g, 0.8 mol) was added very slowly to the mixture of methyl 6-(acetoxymethyl)piperidine-3-carboxylate (133 g, 0.16 mol) in THF (300 ml) and $H_2O$ (300 ml), followed by Cbz-Cl (270 g, 0.16 mol). The mixture was stirred at room temperature for 18 hours. The mixture was filtered, extracted with EA (600 ml*3). The combined organic layers were dried over $Na_2SO_4$, filtered and concentrated to give the crude product. Chromatograph column (EA in PE from 0% to 33%) gave colorless oil. Prep-HPLC gave trans-1-benzyl 3-methyl 6-(acetoxymethyl)piperidine-1,3-dicarboxylate. $^1H$ NMR: 400 MHz $CDCl_3$ δ: 7.377~7.323 (m, 5H), 5.188~5.080 (m, 2H), 4.627~4.570 (m, 1H), 4.325~4.284 (m, 2H), 4.235~4.137 (s, 1H), 3.700 (s, 3H), 3.066~2.965 (m, 1H), 2.557~2.400 (m, 1H), 2.018~1.917 (m, 4H), 1.772~1.648 (m, 4H) ppm.

Step 6. (3S,6R)-1-benzyl 3-methyl 6-(hydroxymethyl)piperidine-1,3-dicarboxylate and (3R,6S)-1-benzyl 3-methyl 6-(hydroxymethyl)piperidine-1,3-dicarboxylate The mixture of trans-1-benzyl 3-methyl 6-(acetoxymethyl)piperidine-1,3-dicarboxylate (25 g, 0.072 mmol), $NaHCO_3$ (54 g, 0.64 mol) and $K_2CO_3$ (4.94 g, 35.8 mmol) in MeOH (100 ml) was stirred at room temperature for 1 hour, filtered, diluted with $H_2O$ (100 ml), extracted with DCM (100 ml×3). The combined organic layers were washed with $H_2O$ (100 ml), brine (100 ml), evaporated in vacuo to get crude product. Chromatograph column (EA in PE from 0% to 33%) gave colorless oil trans-1-benzyl 3-methyl 6-(hydroxymethyl)piperidine-1,3-dicarboxylate. The racemic mixture was further separated by SFC to obtain (3S,6R)-1-benzyl 3-methyl 6-(hydroxymethyl)piperidine-1,3-dicarboxylate (retention time=4.254 min) and (3R,6S)-1-benzyl 3-methyl 6-(hydroxymethyl)piperidine-1,3-dicarboxylate (retention time=4.607 min). SFC separation condition: Instrument: SFC Thar 200. Column: Chiralpak AD-H 250×50 mmI.D., 10 um. Mobile phase: A for $CO_2$ and B for ETOH (0.1% $NH_3H_2O$). Gradient: B 40% Flow rate: 200 mL/min. Back pressure: 100 bar. Column temperature: 35° C. Wavelength: 220 nm. $^1H$ NMR: 400 MHz $CDCl_3$ δ: 7.379~7.311 (m, 5H), 5.227~5.195 (d, J=12.8 Hz, 1H), 5.121~5.089 (d, J=12.8 Hz, 1H), 4.248~4.169 (m, 2H), 3.846~3.818 (m, 1H), 3.721~3.679 (m, 1H), 3.625 (s, 3H), 3.450~3.322 (m, 1H), 2.617~2.594 (m, 1H), 1.999~1.899 (m, 1H), 1.855~1.831 (m, 2H), 1.616~1.582 (m, 1H) ppm ppm.

Step 7: (3R,6S)-1-benzyl 3-methyl 6-(((tert-butyldiphenylsilyl)oxy)methyl)piperidine-1,3-dicarboxylate To a solution of (3R,6S)-1-benzyl 3-methyl 6-(hydroxymethyl)piperidine-1,3-dicarboxylate (2.00 g, 6.51 mmol), imidazole (0.532 g, 7.81 mmol) in DMF (10 ml) was added TBDPS-Cl (2.0 ml, 7.81 mmol). It was stirred at rt for 2 h. Precipitates were found. The reaction mixture was diluted with ethyl acetate, washed with water three times, then brine once. The organic layer was dried over sodium sulfate, filtered and concentrated. The residue was purified by ISCO (Gold 120 g, 0-50% ethyl acetate in hexane) to give the title compound as a solid. LC-MS: $C_{32}H_{39}NO_5Si$, calc.=546.27; found=546.29 $(M+H)^+$.

Step 8: (3R,6S)-1-((benzyloxy)carbonyl)-6-(((tert-butyldiphenylsilyfloxy)methyl)piperidine-3-carboxylic acid To a solution of (3R,6S)-1-benzyl 3-methyl 6-(((tert-butyldiphenylsilyl)oxy)methyl)piperidine-1,3-dicarboxylate (3.40 g, 6.23 mmol) in THF (40 ml), MeOH (40.0 ml) and water (40.0 ml) was added LiOH (5 M, 8 ml, 40.0 mmol) slowly. It was stirred at rt for 3 h and acidified by 1 M HCl (about 40 mL) to adjust pH to 5. The mixture was extracted with ethyl acetate (3×100 mL). The combined organic layers were washed with brine (100 mL), dried over sodium sulfate, filtered and concentrated under reduced pressure. The residue was used without purification. LC-MS: $C_{31}H_{37}NO_5Si$, calc.=532.25; found=532.34 $(M+H)^+$.

Step 9: (2S,5R)-benzyl 2-4(tert-butyldiphenylsilyfloxy)methyl)-5-4(3-chloropyrazin-2-yl)methyl)carbamoyl)piperidine-1-carboxylate To a mixture of (3R,6S)-1-((benzyloxy)carbonyl)-6-(((tert-butyldiphenylsilyl)oxy)methyl)piperidine-3-carboxylic acid (3.3 g, 6.21 mmol), (3-chloropyrazin-2-yl)methanamine bis-hydrocloride salt (1.478 g, 6.83 mmol) and HATU (2.83 g, 7.45 mmol) in DMF (20 ml) was added DIEA (3.25 ml, 18.62 mmol). The mixture was stirred at rt for 1 h. Most solvent was removed under reduced pressure and the residue was diluted with ethyl acetate (100 mL), washed with water (3×50 mL), then brine (100 mL). The organic layer was seperated and dried over sodium sulfate, filtered and concentrated under redueced pressure. The residue was purified by ISCO (Gold 80 g, 0-100% EtOAc/EtOH (3:1) in hexane) to give the title compound as a solid. LC-MS: $C_{36}H_{41}ClN_4O_4Si$, calc.=656.27; found=656.41 $(M+H)^+$.

Step 10: (2S,5R)-benzyl 2-(((tert-butyldiphenylsilyl)oxy)methyl)-5-(8-chloroimidazo[1,5-a]pyrazin-3-yl)piperidine-1-carboxylate To a mixture of (2S,5R)-benzyl 2-(((tert-butyldiphenylsilyl)oxy)methyl)-5-(((3-chloropyrazin-2-yl)methyl)carbamoyl)piperidine-1-carboxylate (2.2 g, 3.35 mmol) and sodium carbonate (2.84 g, 26.8 mmol) in acetonitrile (12 mL) and DMF (12.00 mL) at 0° C. was added $POCl_3$ (1 mL, 10.73 mmol) dropwise. It was warmed to 45° C. and stirred for 1 h. The mixture was diluted with 100 mL of ethyl acetate and washed with water (3×50 mL). The combined aqueous layers were extracted with ethyl acetate (100 mL). The combined organic layers were washed with brine, dried over sodium sulfate, filtered and concentrated. The residue was purified by ISCO (Gold 40 g, 0-100% EtOAc/EtOH (3:1) in hexane) to give the title compound. LC-MS: $C_{36}H_{39}ClN_4O_3Si$, calc.=639.26; found=656.41 (M+H)$^+$.

Step 11: (2S,5R)-benzyl 5-(1-bromo-8-chloroimidazo[1,5-a]pyrazin-3-yl)-2-(((tert-butyldiphenylsilyl)oxy)methyl)piperidine-1-carboxylate To a solution of (2S,5R)-benzyl 2-(((tert-butyldiphenylsilyl)oxy)methyl)-5-(8-chloroimidazo[1,5-a]pyrazin-3-yl)piperidine-1-carboxylate (1.33 g, 2.081 mmol) in acetonitrile (15 ml) was added NBS (0.444 g, 2.497 mmol). The mixture was stirred at rt for 15 min. It was concentrated and purified by ISCO (gold 40 g, 0-50% ethyl acetate in hexane) to give the title compound. LC-MS: $C_{36}H_{38}BrClN_4O_3Si$, calc.=717.17, 719.17; found=717.35, 719.30 (M+H)$^+$.

Step 12: (2S,5R)-benzyl 5-(1-bromo-8-((2,4-dimethoxybenzyl)amino)imidazo[1,5-a]pyrazin-3-yl)-2-(((tert-butyldiphenylsilyl)oxy)methyl)piperidine-1-carboxylate To a solution of (2S,5R)-benzyl 5-(1-bromo-8-chloroimidazo[1,5-a]pyrazin-3-yl)-2-(((tert-butyldiphenylsilyl)oxy)methyl)piperidine-1-carboxylate (1.35 g, 1.880 mmol) in DMF (6 ml) was added 2,4-dimethoxybenzylamine (0.40 g, 2.392 mmol) and triethylamine (0.42 ml, 3.01 mmol). The mixture was stirred at 60° C. for 4 h. It was diluted with ethyl acetate, washed with water three times and brine once. The organic layer was dried over sodium sulfate, filtered and concentrated under reduced pressure. The residue was purified by ISCO (Gold 40 g, 0-50% ethyl acetate in hexane) to give the title compound as a solid. LC-MS: $C_{45}H_{50}BrN_5O_5Si$, calc.=848.36, 850.31; found=848.28, 850.29 (M+H)$^+$.

Step 13: (2S,5R)-benzyl 5-(1-bromo-8-((2,4-dimethoxybenzyl)amino)imidazo[1,5-a]pyrazin-3-yl)-2-(hydroxymethyl)piperidine-1-carboxylate A solution of (2S,5R)-benzyl 5-(1-bromo-8-((2,4-dimethoxybenzyl)amino)imidazo[1,5-a]pyrazin-3-yl)-2-(((tert-butyldiphenylsilyl)oxy)methyl)piperidine-1-carboxylate (880 mg, 1.037 mmol) in THF (5 ml) in a plastic vial was treated with HF (70 wt % in pyridine, 0.8 ml, 1.037 mmol) at rt for 3 h. It was diluted with ethyl acetate, washed with sodium bicarbonate, brine. The organic layer was dried over sodium sulfate, filtered and concentrated. The residue was purified by ISCO (Gold 40 g, 0-100% EtOAc/EtOH in hexane) to give the title compound. LC-MS: $C_{29}H_{32}BrN_5O_5$, calc.=610.17, 612.17; found=610.21, 612.16 (M+H)$^+$.

Step 14: (2S,5R)-benzyl 5-(1-bromo-8-((2,4-dimethoxybenzyl)amino)imidazo[1,5-a]pyrazin-3-yl)-2-formylpiperidine-1-carboxylate To a solution of (2S,5R)-benzyl 5-(1-bromo-8-((2,4-dimethoxybenzyl)amino)imidazo[1,5-a]pyrazin-3-yl)-2-(hydroxymethyl)piperidine-1-carboxylate (550 mg, 0.901 mmol) in DCM (9 mL) was added Dess-Martin periodinane (535 mg, 1.261 mmol). It was stirred at rt for 30 min. The reaction was quenched with aqueous sodium bicarbonate and sodium thiosulfate. The mixture was extracted with ethyl acetate. The organic layer was dried over sodium sulfate, filtered and concentrated under reduced pressure to give the title compound as a solid. It was used without further purification. LC-MS: (M+H)$^+$574.1, 576.1. Retention time=1.33 min, method B.

Step 15: (2S,5R)-tert-butyl 5-(1-bromo-8-((2,4-dimethoxybenzyl)amino)imidazo[1,5-a]pyrazin-3-yl)-2-(4S)-2-(methoxycarbonyl)pyrrolidin-1-yl)methyl)piperidine-1-carboxylate To a 20 ml sample vial was charged with (2S,5R)-tert-butyl 5-(1-bromo-8-((2,4-dimethoxybenzyl)amino)imidazo[1,5-a]pyrazin-3-yl)-2-formylpiperidine-1-carboxylate (81 mg, 0.141 mmol), (S)-methyl pyrrolidine-2-carboxylate hydrochloride (28.0 mg, 0.169 mmol), along with MS 4A (100 mg) and ClCH$_2$CH$_2$Cl (2 ml). The mixture was stirred and sodium triacetoxyhydroborate (32.9 mg, 0.155 mmol) was added. The resulting reaction mixture was stirred at room temperature for 30 min. The reaction was then quenched by diluting with methylene chloride (10 mL) and NaHCO$_3$ (sat, 3 mL). The organic layer was separated and the aqueous layer was extracted by methylene chloride (2×). The combined organic phases were dried by MgSO$_4$, filtered and concentrated to afford (2S,5R)-tert-butyl 5-(1-bromo-8-((2,4-dimethoxybenzyl)amino)imidazo[1,5-a]pyrazin-3-yl)-2-(((S)-2-(methoxycarbonyl)pyrrolidin-1-yl)methyl)piperidine-1-carboxylate which is used to next step without further purification. LC-MS: (M+H)$^+$687.1, 689.1, retention time=1.22 min.

Step 16: (8R,11aS)-8-(8-amino-1-bromoimidazo[1,5-a]pyrazin-3-yl)octahydro-1H-pyrido[1,2-a]pyrrolo[1,2-d]pyrazin-11(11aH)-one To a 20 ml sample vial was charged with (2S,5R)-tert-butyl 5-(1-bromo-8-((2,4-dimethoxybenzyl)amino)imidazo[1,5-a]pyrazin-3-yl)-2-(((S)-2-(methoxycarbonyl)pyrrolidin-1-yl)methyl)piperidine-1-carboxylate, 359570-010 (75 mg, 0.109 mmol) along with 2,2,2-trifluoroacetic acid (2 mL, 26.1 mmol). The mixture was then stirred and heated in an oil bath of 100° C. for 7 hrs. The deprotection happened very fast in a few minutes, however the cyclication for the formation of lactam was very slow. After cooled to room temperature, the mixture was concentrated by rotary evaporation. The residue was then partitioned between methylene chloride (5 mL) and NaHCO$_3$ (sat, 2 mL). The organic layer was separated and the aquouse layer was extracted (2×). The combined organic phases were dried over MgSO$_4$, filtered and concentrated. The crude was purified by MPLC (4 g silica gel, 0 to 10% methanol in methylene chloride) to afford solid product (8R,11aS)-8-(8-amino-1-bromoimidazo[1,5-a]pyrazin-3-yl)octahydro-1H-pyrido[1,2-a]pyrrolo[1,2-d]pyrazin-11(11aH)-one. LC-MS: (M+H)+404.9, 406.9, retention time=0.46 min. $^1$H NMR (CDCl$_3$, 500 MHz): δ=7.31 (1H, d, J=5.0 Hz), 7.00 (1H, d, J=5.0 Hz), 5.93 (2H, br), 4.84 (1H, dd, J=13.0, 3.0 hz), 3.48 (1H, dd, J=5.0, 2.0 Hz), 3.06 (1H, m), 3.96 (1H, m), 2.86 (1H, dd, J=11.5, 2.5 Hz), 2.77 (1H, m), 2.69 (2H, m), 2.34 (1H, m), 2.15 (2H, m), 1.92 (3H, m), 1.75 (2H, m) ppm.

Intermediate 19

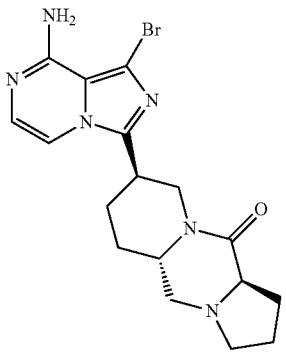 [SMILES: Nc1nccn2c([C@@H]3CC[C@H]4CN5CCC[C@@H]5C(=O)N4C3)nc(Br)c12]

(5aS,8R,11aR)-8-(8-amino-1-bromoimidazo[1,5-a]pyrazin-3-yl)octahydro-1H-pyrido[1,2-a]pyrrolo[1,2-d]pyrazin-11(11aH)-one In the same procedure for the preparation of Intermediate 18, at step 15, (R)-methyl pyrrolidine-2-carboxylate hydrochloride was applied for the reduction amination, the title compound (5aS,8R,11aR)-8-(8-amino-1-bromoimidazo[1,5-a]pyrazin-3-yl)octahydro-1H-pyrido[1,2-a]pyrrolo[1,2-d]pyrazin-11(11aH)-one was prepared. LC-MS: (M+H)$^+$ 405.0, 406.9, retention time=0.30 min, method B.

Intermediate 20

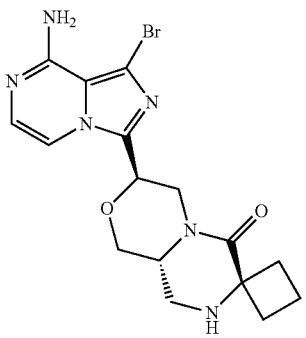

(7'R,9a'S)-7'-(8-amino-1-bromoimidazo[1,5-a]pyrazin-3-yl)hexahydrospiro[cyclobutane-1,3'-pyrido[1,2-a]pyrazin]-4'(2'H)-one In the same procedure for the preparation of Intermediate 18, at step 15, methyl 1-aminocyclopentanecarboxylate oxalate was applied for the reduction amination, the title compound (7'R,9a'S)-7'-(8-amino-1-bromoimidazo[1,5-a]pyrazin-3-yl)hexahydrospiro [cyclobutane-1,3'-pyrido[1,2-a]pyrazin]-4'(2'H)-one was prepared. LC-MS: (M+H)$^+$ 404.9, 406.9, retention time=0.31 min, method B.

Intermediate 21

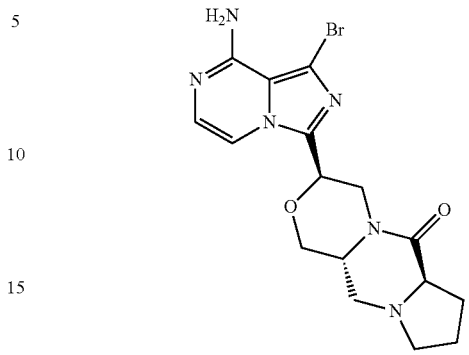

4-(8-amino-3-((3R,6aR,11aR)-6-oxodecahydropyrrolo[1',2':4,5]pyrazino[2,1-c][1,4]oxazin-3-yl)imidazo[1,5-a]pyrazin-1-yl)-3-ethoxy-N-(4-(trifluoromethyl)pyridin-2-yl)benzamide Step 1: (2R,5S)-tert-butyl 2-(1-bromo-8-chloroimidazo[1,5-a]pyrazin-3-yl)-5-(((tert-butyldiphenylsilyl)oxy)methyl)morpholine-4-carboxylate To a solution of (2R,5S)-tert-butyl 5-(((tert-butyldiphenylsilyl)oxy)methyl)-2-(8-chloroimidazo[1,5-a]pyrazin-3-yl)morpholine-4-carboxylate (6.2 g, 10.21 mmol) in acetonitrile (80 mL) was added 1-bromopyrrolidine-2,5-dione (1.999 g, 11.23 mmol) under N$_2$, and the mixture stirred at 20° C. for 1.5 hours. The mixture was poured into an ice-water (200 mL), and 10 mL of sat. aq. NaHCO$_3$ was added. The mixture was filtered, and the filter cake was dissolved with 200 mL of EtOAc, the organic layer was washed with H$_2$O (10 mL×5), brine (20 mL×2), dried over Na$_2$SO$_4$, filtered, and evaporated to afford the title compound, which was used in the next step directly. $^1$H NMR (400 MHz, CDCl$_3$) δ=8.05 (d, J=5.1 Hz, 1H), 7.68 (t, J=5.1 Hz, 4H), 7.49-7.36 (m, 6H), 7.34 (d, J=4.7 Hz, 1H), 5.06 (d, J=3.5 Hz, 1H), 4.74 (d, J=14.1 Hz, 1H), 4.15 (d, J=6.7 Hz, 1H), 3.95-3.87 (m, 2H), 3.81-3.73 (m, 1H), 3.38 (dd, J=4.3, 14.1 Hz, 1H), 3.28 (dd, J=3.3, 11.9 Hz, 1H), 1.50 (s, 9H), 1.05 (s, 9H).

Step 2: (2R,5S)-tert-butyl 2-(1-bromo-8-((2,4-dimethoxybenzyl)amino)imidazo[1,5-a]pyrazin-3-yl)-5-(((tert-butyldiphenylsilyfloxy)methyl)morpholine-4-carboxylate To a solution of (2R,5S)-tert-butyl 2-(1-bromo-8-chloroimidazo[1,5-a]pyrazin-3-yl)-5-(((tert-butyldiphenylsilyl)oxy)methyl)morpholine-4-carboxylate (6.9 g, 10.06 mmol) in DMF (70 mL) was added K$_2$CO$_3$ (3.47 g, 25.1 mmol) and (2,4-dimethoxyphenyl)methanamine (2.186 g, 13.07 mmol) under N$_2$, and the reaction mixture was stirred at 80° C. for 2 hours. LCMS showed the reaction was complete, and then the brown mixture was cooled to 20° C. and poured into an ice-water (300 mL) slowly, and the mixture was filtered, and the filter cake was dissolved with EtOAc (300 mL). The organic layer was washed with H$_2$O (50 mL×5), brine (50 mL), dried over Na$_2$SO$_4$, evaporated to give the crude product, which was then purified by flash chromatography (Pet. ether/EtOAc=70~60%) to afford the title compound.

¹H NMR (400 MHz, CDCl₃) δ=7.68 (t, J=5.5 Hz, 4H), 7.49-7.34 (m, 7H), 7.28 (s, 1H), 7.11 (d, J=5.1 Hz, 1H), 6.75 (br. s., 1H), 6.49 (s, 1H), 6.45 (dd, J=1.8, 8.0 Hz, 1H), 4.96 (d, J=3.1 Hz, 1H), 4.72-4.60 (m, 3H), 4.18-4.11 (m, 1H), 3.93-3.83 (m, 5H), 3.82-3.74 (m, 4H), 3.41-3.28 (m, 2H), 1.49 (s, 9H), 1.04 (s, 9H) ppm.

Step 3: (2R,5R)-tert-butyl 2-(1-bromo-8-((2,4-dimethoxybenzyl)amino)imidazo[1,5-a]pyrazin-3-yl)-5-(hydroxymethyl)morpholine-4-carboxylate To a solution of (2R,5S)-tert-butyl 2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate (6.6 g, 8.08 mmol) in THF (80 mL) was added TBAF (9.70 mL, 9.70 mmol) slowly, and the light brown mixture was stirred at 20° C. for 12 hours. TLC (Pet. ether/THF=1:1) showed the reaction was complete, and then the mixture was quenched with H₂O (50 mL), the mixture was extracted with EtOAc (50 mL×3). The organic layer was washed with brine (50 mL), dried over Na₂SO₄, evaporated to get the crude product, which was then purified by flash chromatography (Pet. ether/THF=50~40%) to afford the title compound.
¹H NMR (400 MHz, CDCl₃) δ=7.40 (d, J=5.1 Hz, 1H), 7.27 (br. s., 1H), 7.11 (d, J=4.7 Hz, 1H), 6.76 (br. s., 1H), 6.49 (s, 1H), 6.44 (dd, J=2.0, 8.2 Hz, 1H), 4.98 (br. s., 1H), 4.67 (d, J=2.7 Hz, 2H), 4.48 (dd, J=2.3, 13.7 Hz, 1H), 3.98-3.85 (m, 6H), 3.80 (s, 3H), 3.77-3.71 (m, 2H), 3.69 (br. s., 1H), 3.47 (dd, J=2.9, 11.9 Hz, 1H), 1.52 (s, 9H) ppm.

Step 4: (2R,5S)-tert-butyl 2-(1-bromo-8-((2,4-dimethoxybenzyl)amino)imidazo[1,5-a]pyrazin-3-yl)-5-formylmorpholine-4-carboxylate To a solution of (2R,5R)-tert-butyl 2-(1-bromo-8-((2,4-dimethoxybenzyl)amino)imidazo[1,5-a]pyrazin-3-yl)-5-(hydroxymethyl)morpholine-4-carboxylate (1.14 g, 1.971 mmol) in DCM (20 mL) was added Dess-Martin Periodinane (1.254 g, 2.96 mmol) in portions at 0° C., and the mixture was stirred for 3 hours. TLC showed most of the starting material was consumed, and the mixture was poured into 80 mL of sat. aq. NaHCO₃ in an ice-bathe, and 1.5 g of Na₂S₂O₃ was added to the mixture, and stirred for 10 min. The mixture was extracted with DCM (30 mL×3), and the organic layer was washed with brine (20 mL), dried over Na₂SO₄, evaporated to get the crude product, which was purified by flash chromatography (Pet. ether/THF=70~60%) to afford the title compound.
¹H NMR (400 MHz, CDCl₃) δ=9.63 (s, 1H), 7.33 (d, J=4.7 Hz, 1H), 7.26 (br. s., 1H), 7.12 (d, J=5.1 Hz, 1H), 6.77 (br. s., 1H), 6.48 (d, J=1.6 Hz, 1H), 6.43 (dd, J=2.0, 8.2 Hz, 1H), 4.92 (br. s., 1H), 4.66 (d, J=3.9 Hz, 2H), 4.37 (dd, J=4.3, 13.7 Hz, 1H), 4.28 (br. s., 1H), 4.03 (d, J=9.4 Hz, 1H), 3.87 (s, 3H), 3.79 (s, 3H), 3.76-3.71 (m, 1H), 3.61 (d, J=8.2 Hz, 1H), 1.52 (br. s., 9H) ppm.

Step 5: (2R,5R)-tert-butyl 2-(1-bromo-8-((2,4-dimethoxybenzyl)amino)imidazo[1,5-a]pyrazin-3-yl)-5-((2-(methoxycarbonyl)pyrrolidin-1-yl)methyl)morpholine-4-carboxylate To a mixture of (2R,5S)-tert-butyl 2-(1-bromo-8-((2,4-dimethoxybenzyl)amino)imidazo[1,5-a]pyrazin-3-yl)-5-formylmorpholine-4-carboxylate (200 mg, 0.347 mmol), methyl pyrrolidine-2-carboxylate (53.8 mg, 0.416 mmol) and sodium cyanoborohydride (65.4 mg, 1.041 mmol) in CH₂Cl₂ (5 mL) was added AcOH (1.986 μl, 0.035 mmol). The mixture was stirred at 20° C. for 12 hours. The mixture was diluted with water (5 mL) and extracted with ethyl acetate (10 mL×4). The combined organic layers were washed with brine (10 mL), dried over sodium sulfate and concentrated to afford the crude product, which was purified on silica gel column chromatograph (DCM/THF=100%~30%) to afford the title compound. MS: 689.2/691.2 (M+1).

Step 6: (3R,6aR,11aR)-3-(1-bromo-8-((2,4-dimethoxybenzyl)amino)imidazo[1,5-a]pyrazin-3-yl)octahydropyrrolo[1',2':4,5]pyrazino[2,1-c][1,4]oxazin-6(1H)-one A mixture of (2R,5R)-tert-butyl 2-(1-bromo-8-((2,4-dimethoxybenzyl)amino)imidazo[1,5-a]pyrazin-3-yl)-5-(((R)-2-(methoxycarbonyl)pyrrolidin-1-yl)methyl)morpholine-4-carboxylate (200 mg, 0.290 mmol) in HCl/Dioxane (4M) (3 mL, 12.00 mmol) was stirred at 20° C. for 2 hours. LCMS showed that the reaction was complete, then the mixture was concentrated, and the residue was dissolved with H₂O (2 mL) and basified with sat. aq. NaHCO₃ to pH=8~9, and the mixture was extracted with DCM (10 mL×4). The organic layer was washed with brine (10 mL), dried over Na₂SO₄, filtered, and evaporated to give the product (R)-methyl 1-(3R,6R)-6-(1-bromo-8-((2,4-dimethoxybenzypamino)imidazo[1,5-a]pyrazin-3-yl)morpholin-3-yl)methyl)pyrrolidine-2-carboxylate (170 mg), which was then dissolved in anhydrous MeOH (4 mL) was stirred at 80° C. for 12 hours. Then the mixture was cooled to room temperature and evaporated to afford the title compound, which was used in the next step directly.
¹H NMR (400 MHz, CDCl₃) δ=7.29 (d, J=5.1 Hz, 1H), 7.24 (s, 1H), 7.12 (d, J=5.1 Hz, 1H), 6.78 (t, J=5.3 Hz, 1H), 6.48 (s, 1H), 6.44 (d, J=8.2 Hz, 1H), 4.89 (dd, J=2.3, 13.7 Hz, 1H), 4.73-4.63 (m, 3H), 3.98 (dd, J=2.7, 11.3 Hz, 1H), 3.87 (s, 3H), 3.79 (s, 3H), 3.49-3.41 (m, 1H), 3.25 (td, J=5.9, 11.7 Hz, 2H), 3.07-2.94 (m, 2H), 2.47-2.34 (m, 2H), 2.24-2.13 (m, 1H), 2.05-1.95 (m, 1H), 1.92-1.76 (m, 3H) ppm.

Step 7: (3R,6aR,11aR)-3-(8-amino-1-bromoimidazo[1,5-a]pyrazin-3-yl)octahydropyrrolo[1',2':4,5]pyrazino[2,1-c][1,4]oxazin-6(1H)-one A mixture of (3R,6aR,11aR)-3-(1-bromo-8-((2,4-dimethoxybenzypamino)imidazo[1,5-a]pyrazin-3-yl)octahydropyrrolo[1',2':4,5]pyrazino[2,1-c][1,4]oxazin-6(1H)-one (80 mg, 0.144 mmol) in TFA (3 mL) was stirred at 80° C. for 2 hours under N₂. Then the mixture was concentrated, the residue was dissolved with sat. aq. NaHCO₃ (20 mL), and the mixture was extracted with DCM (10 mL×3). The organic layer was washed with brine (10 mL), dried over Na₂SO₄, evaporated to afford the title compound, which was used in the next step directly.
¹H NMR (400 MHz, CDCl₃) δ=7.43 (d, J=4.7 Hz, 1H), 7.06 (d, J=5.1 Hz, 1H), 5.74 (br. s., 2H), 4.94 (dd, J=2.2, 13.9 Hz, 1H), 4.75 (dd, J=2.2, 10.8 Hz, 1H), 4.00 (dd, J=2.7, 11.3 Hz, 1H), 3.88 (d, J=7.4 Hz, 1H), 3.50-3.43 (m, 1H), 3.31-3.23 (m, 2H), 3.10-2.95 (m, 2H), 2.49-2.35 (m, 2H), 2.27-2.15 (m, 1H), 2.07-1.95 (m, 1H), 1.92-1.80 (m, 2H) ppm.

Intermediate 22

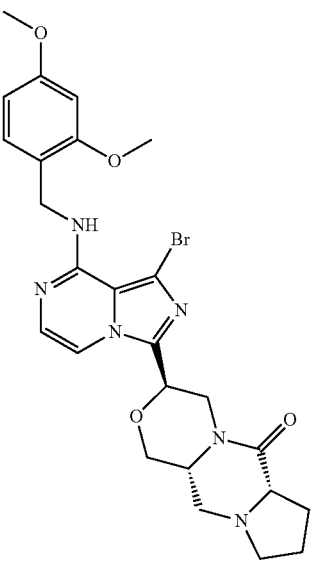 [SMILES: COc1ccc(CNc2nccn3c([C@H]4CN5C(=O)[C@@H]6CCCN6C[C@@H]5CO4)nc(Br)c23)c(OC)c1]

(3R,6aS,11aR)-3-(1-bromo-8-((2,4-dimethoxy benzyl)amino)imidazo[1,5-a]pyrazin-3-yl)octahydropyrrolo[1',2':4,5]pyrazino[2,1-c][1,4]oxazin-6(1H)-one Step 1: (2R,5R)-tert-butyl 2-(1-bromo-8-((2,4-dimethoxybenzyl)amino)imidazo[1,5-a]pyrazin-3-yl)-5-((2-(methoxycarbonyl)pyrrolidin-1-yl)methyl)morpholine-4-carboxylate To a mixture of (2R,5S)-tert-butyl 2-(1-bromo-8-((2,4-dimethoxybenzyl)amino)imidazo[1,5-a]pyrazin-3-yl)-5-formylmorpholine-4-carboxylate (90 mg, 0.156 mmol) methyl pyrrolidine-2-carboxylate (24.20 mg, 0.187 mmol) and $NaCNBH_3$ (29.4 mg, 0.468 mmol) in $CH_2Cl_2$ (2 mL) was added AcOH (0.894 µl, 0.016 mmol). The mixture was stirred at 20° C. for 12 hours. The mixture was diluted with water (5 mL) and extracted with ethyl acetate (10 mL×4). The combined organic layers were washed with brine (10 mL), dried over sodium sulfate and concentrated to afford the crude product, which was purified on silica gel column chromatograph (PE/EA=100%~60%) to afford the title compound. MS: 689.2/691.2 (M+1).

Step 2: (3R,6aS,11aR)-3-(1-bromo-8-((2,4-dimethoxybenzyl)amino)imidazo[1,5-a]pyrazin-3-yl)octahydropyrrolo[1',2':4,5]pyrazino[2,1-c][1,4]oxazin-6(1H)-one A solution of (2R,5R)-tert-butyl 2-(1-bromo-8-((2,4-dimethoxybenzyl)amino)imidazo[1,5-a]pyrazin-3-yl)-5-(((S)-2-(methoxycarbonyl)pyrrolidin-1-yl)methyl)morpholine-4-carboxylate (60 mg, 0.087 mmol) in HCl/Dioxane (2 mL, 7.13 mmol) was stirred at 20° C. for 3 hours. LCMS showed that the reaction was complete, then the mixture was concentrated, and the residue was dissolved with $H_2O$ (5 mL), and basified with sat. aq. $NaHCO_3$ to pH=8~9, and the mixture was extracted with DCM (10 mL×4). The organic layer was washed with brine (10 mL), dried over $Na_2SO_4$, filtered, and evaporated to get the compound (S)-methyl 1-(((3R,6R)-6-(1-bromo-8-((2,4-dimethoxybenzyl)pamino) imidazo[1,5-a]pyrazin-3-yl)morpholin-3-yl)methyl)pyrrolidine-2-carboxylate (50 mg, 88% yield), which was dissolved in anhydrous methanol (3 mL) and was heated at 80° C. for 12 hrs under $N_2$. The mixture was cooled to room temperature, and evaporated to afford the title compound, which was used in the next step directly.

$^1$H NMR (400 MHz, $CDCl_3$) δ=7.28-7.26 (m, 1H), 7.25-7.23 (m, 1H), 7.13 (d, J=5.1 Hz, 1H), 6.79 (br. s., 1H), 6.49 (s, 1H), 6.44 (d, J=8.2 Hz, 1H), 4.94 (d, J=14.1 Hz, 1H), 4.74-4.65 (m, 3H), 3.88 (s, 4H), 3.80 (s, 3H), 3.75 (br. s., 1H), 3.39-3.29 (m, 1H), 3.06 (t, J=8.0 Hz, 1H), 2.92 (br. s., 1H), 2.84-2.71 (m, 2H), 2.42 (br. s., 1H), 2.18 (br. s., 1H), 2.01-1.85 (m, 2H), 1.81 (br. s., 1H), 1.65 (br. s., 1H) ppm.

Intermediate 23, 24

6'-(8-amino-1-bromoimidazo[1,5-a]pyrazin-3-yl)tetrahydro-2'H-spiro[cyclopropane-1,1'-indolizin]-3'(5'H)-one (23), and 6'-(8-amino-1-bromoimidazo[1,5-a]pyrazin-3-yl)tetrahydro-2'H-spiro[cyclopropane-1,1'-indolizin]-3'(5'H)-one (24)

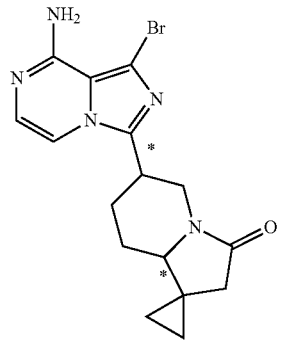

23

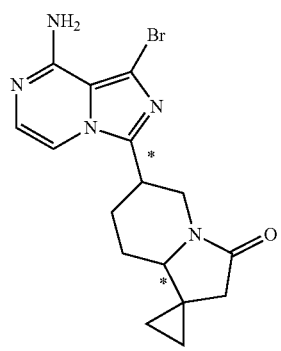

24

Step 1: 1-(5-bromopyridin-2-yl)cyclopropanecarbonitrile

To a stirred solution of cyclopropanecarbonitrile (19.06 g, 284 mmol) and 5-bromo-2-fluoropyridine (50 g, 284 mmol) in toluene (400 mL) was added potassium bis(trimethylsilyl) amide (500 ml, 500 mmol) in THF (1M) dropwise at 0° C., the reaction mixture was stirred at 10° C. for 16 hours. After quenching with a saturated aqueous solution of ammonium chloride (500 mL), the mixture was extracted with EtOAc (200 mL×3). The combined organic layers were washed with brine (500 mL). The extracts were dried over $Na_2SO_4$, filtered and concentrated under reduced pressure. The residue was purified by silica gel column chromatography (Petr. ether/ethyl acetate=100%~80%) to afford 1-(5-bromopyridin-2-yl)cyclopropanecarbonitrile. $^1$H NMR (CDCl$_3$ 400 MHz) δ=8.48 (d, J=1.6 Hz, 1H), 7.79 (dd, J=2.0, 8.2 Hz, 1H), 7.59 (d, J=8.2 Hz, 1H), 1.80-1.75 (m, 2H), 1.74-1.69 (m, 2H) ppm.

Step 2:
1-(5-bromopyridin-2-yl)cyclopropanecarboxylic acid

To a solution of 1-(5-bromopyridin-2-yl)cyclopropanecarbonitrile (58 g, 260 mmol) in ethanol (500 mL) was added a solution of NaOH (31.2 g, 780 mmol) in water (100 mL), then the mixture was heated to 100° C. for 24 hours. After cooling to room temperature, the solution was poured into an ice-cold saturated aqueous Na$_2$HPO$_4$ solution (500 mL) and the resulting mixture was adjusted to pH 4 by the addition of 1 M aqueous hydrochloric acid. The mixture was extracted with EtOAc (300 mL×4). The combined organic layers were washed with brine (500 mL) The extracts were dried over Na$_2$SO$_4$, filtered and concentrated under reduced pressure to give 1-(5-bromopyridin-2-yl)cyclopropanecarboxylic acid. $^1$H NMR (CDCl$_3$ 400 MHz) δ=8.50 (d, J=1.6 Hz, 1H), 7.87 (dd, J=2.0, 8.6 Hz, 1H), 6.80 (d, J=8.6 Hz, 1H), 2.09 (q, J=4.0 Hz, 2H), 1.43-1.34 (m, 2H) ppm.

Step 3: 1-(5-bromopyridin-2-yl)-N-methoxy-N-methylcyclopropanecarboxamide

To a solution of 1-(5-bromopyridin-2-yl)cyclopropanecarboxylic acid (60 g, 248 mmol) in anhydrous DMF (600 mL) was added HATU (113 g, 297 mmol) and the mixture was stirred for 30 mins under nitrogen. Et$_3$N (104 ml, 744 mmol) was added and followed by N,O-dimethylhydroxylamine hydrochloride (26.6 g, 273 mmol). The mixture was stirred for 16 hrs at 10° C. The mixture was diluted with water (1500 mL) and extracted with ethyl acetate (500 mL×5). The combined organic layers were washed with water (200 mL×2), brine (1000 mL), dried over Na$_2$SO$_4$ and evaporated to get the crude product, which was purified on silica gel flash chromatography (Pet. ether/EtOAc=100~50%) to give 1-(5-bromopyridin-2-yl)-N-methoxy-N-methylcyclopropanecarboxamide. $^1$H NMR (CDCl$_3$ 400 MHz) δ=8.49 (d, J=1.6 Hz, 1H), 7.68 (dd, J=2.2, 8.4 Hz, 1H), 7.06 (d, J=8.6 Hz, 1H), 3.43 (br. s., 3H), 3.19 (s, 3H), 1.49-1.38 (m, 4H) ppm.

Step 4:
(1-(5-bromopyridin-2-yl)cyclopropyl)methanol

To a solution of 1-(5-bromopyridin-2-yl)-N-methoxy-N-methylcyclopropanecarboxamide (60 g, 210 mmol) in EtOH (600 ml) was added NaBH$_4$ (23.88 g, 631 mmol) in portions at 0° C. The mixture was stirred at 30° C. for 20 hours, then poured into a saturated aqueous solution of NH$_4$Cl (1000 mL), and extracted with EtOAc (300 mL×4). The combined organic layers were washed with brine (500 mL) The extracts were dried over Na$_2$SO$_4$, filtered and concentrated under reduced pressure. The residue was purified by silica gel column chromatography (Petr. ether/ethyl acetate=100%~50%) to afford (1-(5-bromopyridin-2-yl)cyclopropyl)methanol. $^1$H NMR (CDCl$_3$ 400 MHz) δ=8.51 (d, J=2.3 Hz, 1H), 7.71 (dd, 8.5 Hz, 1H), 6.88 (d, J=8.5 Hz, 1H), 3.82 (s, 2H), 3.75 (br. s., 1H), 1.07 (d, J=3.3 Hz, 4H) ppm.

Step 5:
2-(1-(5-bromopyridin-2-yl)cyclopropyl)acetonitrile

To a solution of (1-(5-bromopyridin-2-yl)cyclopropyl)methanol (20 g, 88 mmol) and Et$_3$N (36.7 ml, 263 mmol) in CH$_2$Cl$_2$(200 mL) was added methanesulfonyl chloride (20.07 ml, 258 mmol) dropwise at 0° C. under nitrogen atmosphere. The mixture was stirred at 0° C. for 4 hours, then washed with saturate aqueous NaHCO$_3$ (50 mL), brine (50 mL), dried over Na$_2$SO$_4$ and concentrated under reduced pressure. The residue was dissolved in DMF (200 mL) and then NaCN (13.21 g, 270 mmol) was added. The mixture was stirred at 70° C. for 18 hours, then diluted with water (600 mL) and extracted with EtOAt (200 mL×4). The combined organic layers were washed with water (100 mL×3), brine (200 mL), dried over Na$_2$SO$_4$, filtered and concentrated under reduced pressure. The residue was purified by silica gel column chromatography (Petr. ether/ethyl acetate=100%~60%) to give 2-(1-(5-bromopyridin-2-yl)cyclopropyl)acetonitrile. $^1$H NMR (CDCl$_3$ 400 MHz) δ=8.56 (d, J=2.0 Hz, 1H), 7.74 (dd, J=2.3, 8.6 Hz, 1H), 6.96 (d, J=8.2 Hz, 1H), 2.92 (s, 2H), 1.30-1.21 (m, 2H), 1.20-1.11 (m, 2H) ppm.

Step 6:
2-(1-(5-bromopyridin-2-yl)cyclopropyl)acetic acid

To a solution of 2-(1-(5-bromopyridin-2-yl)cyclopropyl)acetonitrile (13.5 g, 56.9 mmol) in ethanol (130 mL) was added sodium hydroxide (6.83 g, 171 mmol) in water (30 mL). The mixture was heated to 100° C. for 24 hours. After cooling to room temperature, the solution was poured into ice-cold saturated aqueous Na$_2$HPO$_4$ solution (50 mL) and the resulting mixture was adjusted to pH 4 by the addition of 1 M aqueous hydrochloric acid. The mixture was extracted with EtOAc (200 mL×4). The combined organic layers were washed with brine (200 mL) The extracts were dried over Na$_2$SO$_4$, filtered and concentrated under reduced pressure to give 2-(1-(5-bromopyridin-2-yl)cyclopropyl)acetic acid. $^1$H NMR 0351907-0092-1A (CDCl$_3$ 400 MHz) δ=8.54 (d, J=2.0 Hz, 1H), 7.82 (dd, J=2.3, 8.6 Hz, 1H), 6.92 (d, J=8.6 Hz, 1H), 2.81 (s, 2H), 1.17 (s, 4H) ppm.

Step 7: methyl 2-(1-(5-bromopyridin-2-yl)cyclopropyl)acetate

A solution of 2-(1-(5-bromopyridin-2-yl)cyclopropyl)acetic acid (30 g, 117 mmol) was dissolved in HCl/CH$_3$OH (250 mL)(4M), and the mixture was stirred at 15° C. for 2 hours. The TLC showed completion of the reaction. The mixture was concentrated under reduced pressure. The residue was dissolved in EtOAc (100 mL) and neutralized with sat. NaHCO$_3$(200 mL) (aq.). The aqueous was extracted with EtOAc (100 mL×4). The combined organic layers were washed with brine (200 mL) The extracts were dried over Na$_2$SO$_4$ and concentrated under reduced pressure. The residue was purified by silica gel column chromatography (EtOAc: Pet. ether=0%~30%) to give methyl 2-(1-(5-bromopyridin-2-yl)cyclopropyl)acetate. $^1$H NMR (CDCl$_3$ 400 MHz) δ=8.48 (br. s., 1H), 7.65 (d, J=6.7 Hz, 1H), 6.99 (d, J=8.2 Hz, 1H), 3.75-3.53 (m, 3H), 2.76 (s, 2H), 1.22 (br. s., 1H), 1.01 (br. s., 1H) ppm.

Step 8: methyl 6-(1-(2-methoxy-2-oxoethyl)cyclopropyl)nicotinate

To a solution of methyl 2-(1-(5-bromopyridin-2-yl)cyclopropyl)acetate (10 g, 37.0 mmol) in MeOH (100 mL) and DMF (100 mL) was added Et₃N (15.48 ml, 111 mmol), DPPF (4.10 g, 7.40 mmol) and diacetoxypalladium (0.831 g, 3.70 mmol). The mixture was stirred at 80° C. for 48 hours under CO (50 psi). The reaction mixture was filtered, and the filtrate was concentrated under reduced pressure. Then the residue was diluted with water (300 mL) and extracted with EtOAc (100 mL×4). The combined organic layers were washed with water (50 mL×3), brine (100 mL), dried over Na₂SO₄, and concentrated under reduced pressure. The residue was purified by silica gel column chromatography (EtOAc: Pet. ether=0%~40%) to afford methyl 6-(1-(2-methoxy-2-oxoethyl)cyclopropyl)nicotinate. ¹H NMR (CDCl₃ 400 MHz) δ=9.05 (br. s., 1H), 8.14 (d, J=6.7 Hz, 1H), 7.14 (d, J=8.2 Hz, 1H), 4.00-3.86 (m, 3H), 3.75-3.59 (m, 3H), 2.83 (br. s., 2H), 1.36 (br. s., 2H), 1.10 (br. s., 2H) ppm.

Step 9: methyl 6-(1-(2-methoxy-2-oxoethyl)cyclopropyl)piperidine-3-carboxylate To a solution of methyl 6-(1-(2-methoxy-2-oxoethyl)cyclopropyl)nicotinate (8.5 g, 34.1 mmol) in AcOH (100 ml) was added NaCNBH₄ (6.43 g, 102 mmol) in portions and the mixture was stirred at 40° C. for 24 hours. Then the mixture was concentrated under reduced pressure. The residue was dissolved in water (50 ml) and pH adjusted with a saturated aqueous solution of NaHCO₃(5 mL) to 9, then extracted with EtOAc (50 mL×4). The combined organic layers were washed with brine (100 mL) The extracts were dried over Na₂SO₄, filtered and concentrated under reduced pressure to give crude methyl 6-(1-(2-methoxy-2-oxoethyl)cyclopropyl)piperidine-3-carboxylate. MS: 256.0 (M+1).

Step 10: methyl3'-oxohexahydro-2'H-spiro[cyclopropane-1,1'-indolizine]-6'-Carboxylate A solution of methyl 6-(1-(2-methoxy-2-oxoethyl)cyclopropyl)piperidine-3-carboxylate (10 g, 39.2 mmol) in MeOH (100 ml) was refluxed for 16 hours. Then the reaction mixture was concentrated under reduced pressure. The residue was purified by silica gel column chromatography (Pet. ether/THF=100%~20%) to afford methyl3'-oxohexahydro-2'H-spiro[cyclopropane-1,1'-indolizine]-6'-Carboxylate 1,1'-indolizine]-6'-carboxylate (trans isomer).
¹H NMR (CDCl₃ 400 MHz) δ=4.46 (dd, J=3.3, 13.1 Hz, 1H), 3.74-3.61 (m, 3H), 3.18 (dd, J=2.7, 11.7 Hz, 1H), 2.78 (t, J=12.3 Hz, 1H), 2.50-2.31 (m, 3H), 2.19 (d, J=12.9 Hz, 1H), 1.64-1.51 (m, 2H), 1.28-1.15 (m, 1H), 0.72 (dtd, J=5.5, 9.8, 19.2 Hz, 2H), 0.65-0.56 (m, 1H), 0.56-0.46 (m, 1H) ppm.

Step 11: 3'-oxohexahydro-2'H-spiro[cyclopropane-1,1'-indolizine]-6'-carboxylic acid (trans)

To a solution of methyl3'-oxohexahydro-2'H-spiro[cyclopropane-1,1'-indolizine]-6'-carboxylate (trans isomer) (1.5 g, 6.72 mmol) in THF (10 mL) was added a solution of LiOH (0.483 g, 20.16 mmol) in water (10 mL) and the mixture was stirred at 10° C. for 3 hours. The mixture was adjusted to pH 4 by the addition of aqueous hydrochloric acid (1 M), then extracted with EtOAc (10 mL×4). The combined organic layers were washed with brine (30 mL) The extracts were dried over Na₂SO₄, filtered and concentrated under reduced pressure to give 3'-oxohexahydro-2'H-spiro[cyclopropane-1,1'-indolizine]-6'-carboxylic acid (trans). ¹H NMR (CDCl₃ 400 MHz) δ=4.49 (dd, J=3.3, 13.5 Hz, 1H), 3.22-3.14 (m, 1H), 2.79 (t, J=12.3 Hz, 1H), 2.50-2.35 (m, 3H), 2.23 (d, J=12.1 Hz, 1H), 1.66-1.53 (m, 2H), 1.21 (d, J=3.5 Hz, 1H), 0.72 (ddd, J=4.7, 9.8, 18.0 Hz, 2H), 0.60 (td, J=5.0, 9.9 Hz, 1H), 0.52 (dd, J=4.5, 9.6 Hz, 1H) ppm.

Step12: N-((3-chloropyrazin-2-yl)methyl)-3'-oxohexahydro-2'H-spiro[cyclopropane-1,1'-indolizine]-6'-carboxamide (trans)

To a solution of (6'R,8a'S)-3'-oxohexahydro-2'H-spiro[cyclopropane-1,1'-indolizine]-6'-carboxylic acid (trans) (100 mg, 0.478 mmol) in DMF (2 mL) were added HATU (113 g, 297 mmol), DIEA (0.250 ml, 1.434 mmol) and (3-chloropyrazin-2-yl)methanamine hydrochloride (86 mg, 0.478 mmol) and the mixture was stirred for 16 hrs at 15° C. The mixture was diluted with water (10 mL) and extracted with ethyl acetate (5 mL×4). The combined organic layers were washed with water (5 mL×3), brine (10 mL), dried over Na₂SO₄, evaporated to get the crude product, which was purified on flash chromatography (Pet. ether/EtOAc=100~60%) to give N-((3-chloropyrazin-2-yl)methyl)-3'-oxohexahydro-2'H-spiro[cyclopropane-1,1'-indolizine]-6'-carboxamide (trans). ¹H NMR (400 MHz, CDCl₃) δ=8.44 (d, J=2.0 Hz, 1H), 8.33 (s, 1H), 6.87 (br. s., 1H), 4.76-4.60 (m, 2H), 4.41 (dd, J=3.1, 12.9 Hz, 1H), 3.21 (dd, J=2.9, 11.5 Hz, 1H), 2.91 (t, J=12.3 Hz, 1H), 2.52-2.28 (m, 3H), 2.16-2.01 (m, 1H), 1.86-1.72 (m, 1H), 1.62 (dd, J=3.1, 13.3 Hz, 1H), 1.31-1.19 (m, 1H), 0.79-0.65 (m, 2H), 0.62 (td, J=5.0, 9.9 Hz, 1H), 0.56-0.47 (m, 1H) ppm.

Step13: 6'-(8-chloroimidazo[1,5-a]pyrazin-3-yl)tetrahydro-2'H-spiro[cyclopropane-1,1'-indolizin]-3'(5I-1)-one (trans)

To a stirred solution of N-((3-chloropyrazin-2-yl)methyl)-3'-oxohexahydro-2'H-spiro[cyclopropane-1,1'-indolizine]-6'-carboxamide (1.8 g, 5.38 mmol) in acetonitrile (20 ml) was added PCl₅ (3.36 g, 16.13 mmol), the reaction mixture was stirred at 10° C. for 3 hours. After cooling to 0° C., the mixture was poured into a saturated aqueous solution of NaHCO₃(50 mL) at 0° C. and extracted with EtOAc (30 mL×4). The combined organic layers were washed with brine (50 mL) The extracts were dried over Na₂SO₄, filtered and concentrated under reduced pressure. The residue was purified by silica gel column chromatography (CH₂Cl₂/MeOH=100%~80%) to afford 6'-(8-chloroimidazo[1,5-a]pyrazin-3-yl)tetrahydro-2'H-spiro[cyclopropane-1,1'-indolizin]-3'(5'H)-one (trans isomer). ¹H NMR (CDCl₃ 400 MHz) δ=7.79 (s, 1H), 7.68 (d, J=4.7 Hz, 1H), 7.35 (d, J=4.7 Hz, 1H), 4.51-4.42 (m, 1H), 3.32 (dd, J=3.1, 11.3 Hz, 1H), 3.03 (d, J=9.0 Hz, 2H), 2.58-2.40 (m, 2H), 2.24-2.16 (m, 1H), 2.14-2.02 (m, 1H), 1.76 (dd, J=3.1, 12.9 Hz, 1H), 1.48-1.35 (m, 1H), 0.85-0.63 (m, 3H), 0.62-0.53 (m, 1H) ppm.

Step14: 6'-(1-bromo-8-chloroimidazo[1,5-a]pyrazin-3-yl)tetrahydro-2'H-spiro[cyclopropane-1,1'-indolizin]-3'(5'H)-one (trans)

To a solution of (6'R, 8a'S)-6'-(8-chloroimidazo[1,5-a]pyrazin-3-yl)tetrahydro-2'H-spiro[cyclopropane-1,1'-indolizin]-3'(5'H)-one (trans isomer) (1.3 g, 4.10 mmol) in acetonitrile (20 ml) was added NBS (0.803 g, 4.51 mmol). The resulting mixture was stirred at 10° C. for 1 hour. LCMS showed that the reaction was complete, the mixture was filtered to remove a white solid and the filtrate was poured into a saturated aqueous solution of NaHCO₃ (30 mL) and extracted with EtOAc (40 mL×3). The combined organic layers were washed with brine (50 mL), dried over Na₂SO₄, filtered and concentrated under reduced pressure. The residue was purified by silica gel column chromatography to afford 6'-(1-bromo-8-chloroimidazo[1,5-a]pyrazin-3-yl)tetrahydro-2'H-spiro[cyclopropane-1,1'-indolizin]-3'(5'H)-one (trans). ¹H NMR (CDCl₃ 400 MHz) δ=7.69 (d, J=5.1 Hz, 1H), 7.36 (d, J=5.1 Hz, 1H), 4.45 (d, J=8.6 Hz, 1H), 3.31 (dd, J=2.9, 11.5 Hz, 1H), 3.07-2.95 (m, 2H), 2.61-2.42 (m, 2H), 2.23-2.08 (m, 2H), 1.77 (dd, J=3.1, 13.3 Hz, 1H), 1.47-1.35 (m, 1H), 0.84-0.66 (m, 3H), 0.60 (dd, J=4.5, 9.6 Hz, 1H) ppm.

Step15: 6'-(8-amino-1-bromoimidazo[1,5-a]pyrazin-3-yl)tetrahydro-2'H-spiro[cyclopropane-1,1'-indolizin]-3'(5'H)-one (trans)

To a solution of (6'R,8a'S)-6'-(1-bromo-8-chloroimidazo[1,5-a]pyrazin-3-yl)tetrahydro-2'H-spiro[cyclopropane-1,1'-indolizin]-3'(5'H)-one (trans isomer) (1.5 g, 3.79 mmol) in 2-Propanol (15 ml) was added aq. ammonia (30 ml, 189 mmol). The mixture was stirred at 120° C. for 18 hours in a 100 mL of autoclave. The reaction mixture was concentrated and the residue was purified by silica gel column chromatography (DCM/MeOH=0%~20%) to afford 6'-(8-amino-1-bromoimidazo[1,5-a]pyrazin-3-yl)tetrahydro-2'H-spiro[cyclopropane-1,1'-indolizin]-3'(51-1)-one (trans). ¹H NMR (CDCl₃ 400 MHz) δ=7.25 (d, J=5.1 Hz, 1H), 7.06 (d, J=4.7 Hz, 1H), 5.67 (br. s., 2H), 4.46 (d, J=11.0 Hz, 1H), 3.30 (dd, J=2.9, 11.5 Hz, 1H), 3.06-2.91 (m, 2H), 2.60-2.42 (m, 2H), 2.22-2.13 (m, 1H), 2.11-1.99 (m, 1H), 1.74 (dd, J=2.9, 13.1 Hz, 1H), 1.39 (dq, J=3.1, 12.7 Hz, 1H), 0.85-0.64 (m, 3H), 0.63-0.54 (m, 1H) ppm.

Step16: 6'-(8-amino-1-bromoimidazo[1,5-a]pyrazin-3-yl)tetrahydro-2'H-spiro[cyclopropane-1,1'-indolizin]-3'(5'H)-one (trans isomer1) and 6'-(8-amino-1-bromoimidazo[1,5-a]pyrazin-3-yl)tetrahydro-2'H-spiro[cyclopropane-1,1'-indolizin]-3'(5'H)-one (trans isomer2)

The trans racemic mixture was resolved with chiral SFC (Instrument: Thar 200 Column: OJ 250 mm×50 mm, 10 um Mobile phase: A: Supercritical CO₂, B: EtOH (0.05% NH₃H₂O, A:B=70:30 at 200 ml/min, Column Temp: 38° C., Nozzle Pressure: 100 Bar, Nozzle Temp: 60° C., Evaporator Temp: 20° C., Trimmer Temp: 25° C. Wavelength: 220 nm) to give 6'-(8-amino-1-bromoimidazo[1,5-a]pyrazin-3-yl)tetrahydro-2'H-spiro[cyclopropane-1,1'-indolizin]-3'(5'H)-one (23). Retention time: 1.203 min. ¹H NMR CDCl₃ 400 MHz=7.24 (d, J=5.1 Hz, 1H), 7.06 (d, J=5.1 Hz, 1H), 5.68 (br. s., 2H), 4.45 (d, J=11.0 Hz, 1H), 3.29 (dd, J=2.7, 11.7 Hz, 1H), 2.99 (q, J=12.3 Hz, 2H), 2.58-2.42 (m, 2H), 2.21-2.12 (m, 1H), 2.10-1.98 (m, 1H), 1.78-1.72 (m, 1H), 1.45-1.33 (m, 1H), 0.82-0.64 (m, 3H), 0.58 (dd, J=4.5, 9.6 Hz, 1H) ppm. 6'-(8-amino-1-bromoimidazo[1,5-a]pyrazin-3-yl)tetrahydro-2'H-spiro[cyclopropane-1,1'-indolizin]-3'(5'H)-one (24). Retention time: 1.362 min. ¹H NMR (CDCl₃ 400 MHz)=7.17 (d, J=5.1 Hz, 1H), 6.97 (d, J=5.1 Hz, 1H), 5.85 (br. s., 2H), 4.38 (d, J=11.0 Hz, 1H), 3.23 (dd, J=2.9, 11.5 Hz, 1H), 3.00-2.86 (m, 2H), 2.50-2.36 (m, 2H), 2.16-2.06 (m, 1H), 2.04-1.91 (m, 1H), 1.66 (dd, J=2.9, 13.1 Hz, 1H), 1.38-1.26 (m, 1H), 0.78-0.58 (m, 3H), 0.51 (dd, J=4.9, 9.2 Hz, 1H) ppm.

Intermediate 25, 26, 27, 28

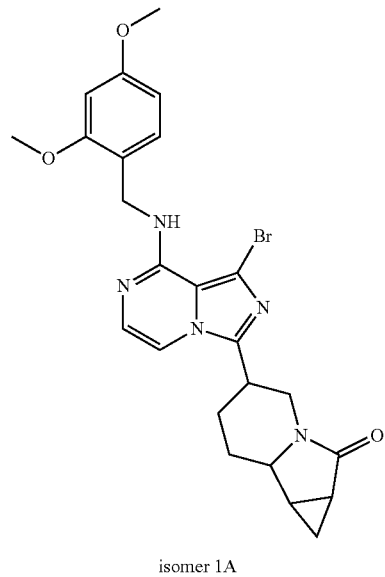

isomer 1A

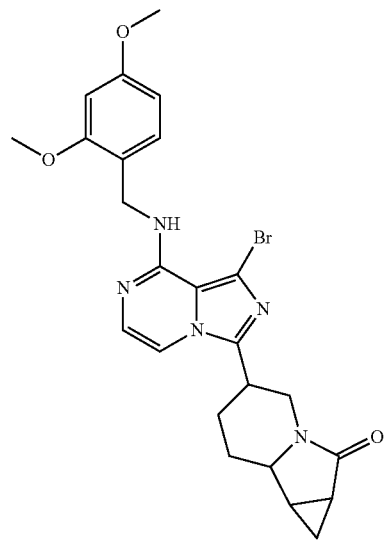

isomer 1B

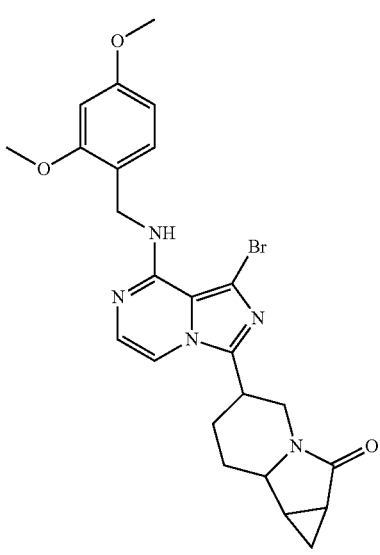

isomer 2A

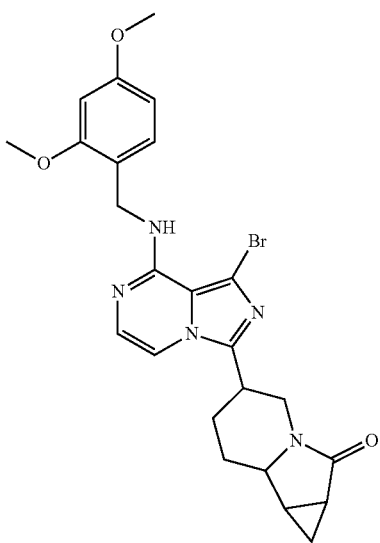

isomer 2B

Trans-4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide (Four isomers)

Step 1: methyl 6-vinylnicotinate

To a solution of methyl 6-bromonicotinate (10 g, 46.3 mmol) in Me$_2$CHOH (200 mL) was added C$_2$H$_3$BF$_4$K+ (14.16 g, 93 mmol), Et$_3$N (19.36 mL, 139 mmol), Pd(dppf)Cl2 (0.2 g). The mixture was stirred at 100° C. for 12 hours under N$_2$ atmosphere. The mixture was concentrated and the residue was purified by column chromatography on silica gel (Pet.ether:EtOAc=15:1) to give methyl 6-vinylnicotinate. MS: 164.2 (M+1). method DM (Rt=0.824 min).

Step 2: methyl 6-(2-(ethoxycarbonyl)cyclopropyl)nicotinate

Ethyl diazoacetate (381 mg, 3.31 mmol) was added to a solution of methyl 6-vinylnicotinate (450 mg, 2.76 mmol) in dimethylbenzene (20 mL). The mixture was heated to 130° C. to reflux for 2 hours, then cooled to 25° C. and stirred for another 12 hours. The reaction solution was concentrated in vacuo and purified with column chromatography on silica gel (CH$_2$Cl$_2$/MeOH=100%~10%) to give methyl 6-(2-(ethoxycarbonyl)cyclopropyl)nicotinate. MS: 250.2 (M+1). method D (Rt=0.995 min). $^1$H NMR (400 MHz, CD$_3$OD): δ=8.94 (s, 1H), 8.23 (d, J=6.0 Hz, 1H), 7.45 (d, J=8.0 Hz, 1H), 4.13 (q, J=6.8 Hz, 2H), 3.90 (s, 3H), 2.68~2.66 (m, 1H), 2.27~2.24 (m, 1H), 1.64~1.59 (m, 2H), 1.23 (t, J=7.2 Hz, 3H) ppm.

Step 3: methyl 6-(2-(ethoxycarbonyl)cyclopropyl)piperidine-3-carboxylate

To a solution of methyl 6-(2-(ethoxycarbonyl)cyclopropyl)nicotinate (250 mg, 1.003 mmol) in acetonitrile (50 mL) was added NaBH$_3$CN (63.0 mg, 1.003 mmol) at 0° C. The mixture was stirred at 15° C. for 12 h. The reaction solution was quenched with water (20 mL) and extracted with EtOAc (20 mL×2). The organic layer was concentrated to give crude product and purified with prep-HPLC (TFA) to give methyl 6-(2-(ethoxycarbonyl)cyclopropyl)piperidine-3-carboxylate. MS: 256.2 (M+1). method D (Rt=0.918 min). $^1$H NMR (400 MHz, CDCl$_3$)=4.21~4.09 (m, 2H), 3.36~3.39 (m, 4H), 2.91 (s, 2H), 2.31~1.55 (m, 6H), 3.90 (s, 3H), 1.28~0.93 (m, 5H) ppm.

Step 4: methyl 2-oxooctahydro-1H-cyclopropa[a]indolizine-5-carboxylate

A solution of methyl 6-(2-(ethoxycarbonyl)cyclopropyl)piperidine-3-carboxylate (200 mg, 0.783 mmol) in toluene (100 mL) was heated to 80° C. and stirred for 12 hours. The reaction solution was concentrated and purified with prep-HPLC (TFA) to give methyl 6-(2-(ethoxycarbonyl)cyclopropyl)piperidine-3-carboxylate. MS: 210.2 (M+1). method D (Rt=0.678 min). $^1$H NMR (400 MHz, CDCl$_3$) δ=4.38 (d, J=6.8 Hz, 1H), 3.67 (s, 3H), 3.60 (s, 1H), 2.77~2.73 (m, 1H), 2.64 (s, 1H), 2.25 (d, J=6.8 Hz, 1H), 1.95~1.92 (m, 2H), 1.84~1.80 (m, 5H), 1.63~1.62 (m, 1H), 1.50~1.47 (m, 1H), 0.96~0.92 (m, 1H), 0.59 (d, J=3.6 Hz, 1H) ppm.

Step 5: 2-oxooctahydro-1H-cyclopropa[a]indolizine-5-carboxylic acid

To a solution of methyl 6-(2-(ethoxycarbonyl)cyclopropyl)piperidine-3-carboxylate (5 g, 23.90 mmol) in THF/H$_2$O (1:1, 80 mL) was added lithium hydroxide (1.431 g, 59.7 mmol). The mixture was stirred at 8° C. for 13 hours. The reaction was acidified to pH=3~5 with 2M aq.HCl and concentrated to give the crude product 2-oxooctahydro-1H-cyclopropa[a]indolizine-5-carboxylic acid. MS: 196.2 (M+1). method D (Rt=0.418 min).

Step 6: N#3-chloropyrazin-2-yl)methyl)-2-oxooctahydro-1H-cyclopropa[a]indolizine-5-carboxamide To the solution of 2-oxooctahydro-1H-cyclopropa[a]indolizine-5-carboxylic acid (3.5 g, 10.76 mmol) in CH$_2$Cl$_2$ (150 mL) and DMF (20 mL) was added EDC (3.09 g, 16.14 mmol) and DMAP (1.971 g, 16.14 mmol) under N$_2$, followed by (3-chloropyrazin-2-yl)methanamine hydrochloride (2.324 g, 12.91 mmol). The resulting mixture was stirred at 15° C. for 3 h. TLC (DCM:MeOH=10:1) and LCMS showed the starting material was consumed completely. The mixture was diluted with H$_2$O (350 mL), extracted with DCM (80 mL×2). The combined organic layers were dried over anhydrous sodium sulfate, filtered and concentrated under vacuum to give crude product which was purified by combi flash (DCM: THF=100-20%) to give N-((3-chloropyrazin-2-yl)methyl)-2-oxooctahydro-1H-cyclopropa[a]indolizine-5-carboxamide. MS (ESI): 321.0 (M+1). method D (Rt=1.078 min). $^1$H NMR (400 MHz, CDCl$_3$)=8.45 (br. s., 1H), 8.37-8.30 (m, 1H), 7.72 (br. s., 1H), 4.75-4.60 (m, 2H), 4.24-4.13 (m, 1H), 3.79-3.64 (m, 1H), 2.89-2.78 (m, 1H), 2.15-2.03 (m, 3H), 1.99-1.87 (m, 1H), 1.85-1.72 (m, 1H), 1.36-1.22 (m, 2H), 1.19-1.01 (m, 1H), 0.79-0.61 (m, 1H) ppm.

Step 7: 5-(8-chloroimidazo[1,5-a]pyrazin-3-yl)hexahydro-1H-cyclopropa[a]indolizin-2(1aH)-one To a solution of N-((3-chloropyrazin-2-yl)methyl)-2-oxooctahydro-1H-cyclopropa[a]indolizine-5-carboxamide (2.0 g, 6.23 mmol) in acetonitrile (80 mL) was added PCl$_5$ (3.90 g, 18.70 mmol) in portions at 0° C. After addition, the mixture was allowed to warm to room temperature (20° C.) and stirred for 12 hrs under N$_2$ atmosphere. Then the mixture was poured into ice aq.NaHCO$_3$ (100 mL) slowly, and stirred for 20 min. The mixture was then extracted with DCM (20 mL×3). The organic layer was washed with brine (20 mL), dried over Na$_2$SO$_4$, and concentrated in vacuo to give the residue, which was then purified with prep HPLC to give 5-(8-chloroimidazo[1,5-a]pyrazin-3-yl)hexahydro-1H-cyclopropa[a]indolizin-2(1aH)-one. MS (ESI):303.0 (M+1). Acq Method 0-60AB_2 min_220&254.1 cm (Rt=1.178 min). $^1$H NMR (400 MHz, CD$_3$OD) δ=8.27-8.22 (m, 1H), 7.96 (s, 1H), 7.47-7.40 (m, 1H), 4.18-4.07 (m, 1H), 3.89-3.79 (m, 1H), 3.25-3.14 (m, 1H), 3.07-2.95 (m, 1H), 2.15 (d, J=9.0 Hz, 2H), 2.04-1.85 (m, 3H), 1.63-1.47 (m, 1H), 1.13-1.05 (m, 1H), 0.82 (d, J=3.5 Hz, 1H).

Step 8: 5-(1-bromo-8-chloroimidazo[1,5-a]pyrazin-3-yl)hexahydro-1H-cyclopropa[a]indolizin-2(1aH)-one NBS was added in one portion to the solution of 5-(8-chloroimidazo[1,5-a]pyrazin-3-yl)hexahydro-1H-cyclopropa[a]indolizin-2(1aH)-one (900 mg, 2.97 mmol) in DMF (12 mL) and the mixture was stirred at room temperature (20° C.) for 2 h. The mixture was then pouted into aq. NaHCO$_3$ (30 mL). The mixture was extracted with EtOAc (35 mL×3), washed with water (10 mL×2) and dried over Na$_2$SO$_4$. The organic layer was concentrated in vacuo, and purified with silica gel (methol/dichloromethane 0%~15%) to give the crude product of 5-(1-bromo-8-chloroimidazo[1,5-a]pyrazin-3-yl)hexahydro-1H-cyclopropa[a]indolizin-2(1aH)-one. $^1$H NMR (400 MHz, CD$_3$OD)=8.20 (dt, J=5.1, 16.3 Hz, 1H), 7.39-7.32 (m, 1H), 4.15-4.06 (m, 2H), 3.88-3.79 (m, 1H), 3.63 (d, J=13.3 Hz, 1H), 3.17-3.08 (m, 1H), 2.19-2.11 (m, 3H), 2.00-1.88 (m, 3H), 1.58-1.47 (m, 1H). MS (ESI): 381/383 (M+1). Acq Method 10-80AB_2 min_220&254.1 cm (Rt=1.014 min).

Step 9: 5-(1-bromo-8-chloroimidazo[1,5-a]pyrazin-3-yl)hexahydro-1H-cyclopropa[a]indolizin-2(1aH)-one To the solution of 5-(1-bromo-8-chloroimidazo[1,5-a]pyrazin-3-yl)hexahydro-1H-cyclopropa[a]indolizin-2(1aH)-one (850 mg, 2.227 mmol)) in DMF (15 mL) was added K$_2$CO$_3$ (923 mg, 6.68 mmol) and (2,4-dimethoxyphenyl)methanamine (447 mg, 2.67 mmol) and the mixture was stirred at 80° C. for 2 hours under N$_2$. The mixture was partitioned between water (50 mL) and ethyl acetate (150 mL), the organic layer was concentrated in vacuo. The residue was purified with preparative HPLC on Gilson 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 19-35% B, 0-13.0 min; 100% B, 13.2-15.2 min; 10% B, 15.4-17 minFlowRate:25 ml/min to give 5-(1-bromo-8-((2,4-dimethoxybenzyl)amino)imidazo[1,5-a]pyrazin-3-yl)hexahydro-1H-cyclopropa[a]indolizin-2(1aH)-one (isomer 1) (the faster eluting) $^1$H NMR (400 MHz, CDCl$_3$) δ=7.11-7.06 (m, 1H), 7.05-7.01 (m, 1H), 6.74 (br. s., 1H), 6.47 (d, J=2.0 Hz, 1H), 6.42 (dd, J=2.2, 8.0 Hz, 1H), 4.65 (d, J=5.5 Hz, 2H), 4.13 (dd, J=3.7, 13.5 Hz, 1H), 3.86 (s, 3H), 3.78 (s, 3H), 3.71-3.64 (m, 1H), 2.87 (t, J=12.3 Hz, 1H), 2.71-2.61 (m, 1H), 2.12-2.02 (m, 2H), 1.97 (d, J=7.8 Hz, 2H), 1.40-1.30 (m, 1H), 1.28-1.20 (m, 1H), 1.04-0.96 (m, 1H), 0.71 (d, J=3.9 Hz, 1H). HPLC METHOD: 0-60AB_1.2 ml.met (Rt=3.11 min). And 5-(1-bromo-8-((2,4-dimethoxybenzyl)amino)imidazol[1,5-a]pyrazin-3-yl)hexahydro-1H-cyclopropa[a]indolizin-2(1aH)-one (isomer 2) (the slower eluting). $^1$H NMR (400 MHz, CDCl$_3$) δ=7.14-7.07 (m, 2H), 6.72 (br. s., 1H), 6.47 (d, J=2.0 Hz, 1H), 6.42 (dd, J=2.3, 8.2 Hz, 1H), 4.65 (d, J=5.5 Hz, 2H), 4.19 (dd, J=3.5, 13.3 Hz, 1H), 3.86 (s, 3H), 3.78 (s, 3H), 3.74-3.67 (m, 1H), 3.46 (d, J=10.6 Hz, 1H), 2.98-2.89 (m, 1H), 2.84-2.75 (m, 1H), 2.10 (d, J=6.3 Hz, 2H), 1.97 (dd, J=3.1, 12.9 Hz, 1H), 1.90 (br. s., 1H), 1.74-1.68 (m, 1H), 1.51-1.40 (m, 1H), 1.12-1.05 (m, 1H). HPLC METHOD: 0-60AB_1.2 ml.met (Rt=3.21 min).

Step 10: 5-(1-bromo-8-chloroimidazo[1,5-a]pyrazin-3-yl)hexahydro-1H-cyclopropa[a]indolizin-2(1aH)-one (isomer 1A), 5-(1-bromo-8-chloroimidazo[1,5-a]pyrazin-3-yl)hexahydro-1H-cyclopropa[a]indolizin-2(1aH)-one (isomer 1B), 5-(1-bromo-8-chloroimidazo[1,5-a]pyrazin-3-yl)hexahydro-1H-cyclopropa[a]indolizin-2(1aH)-one (isomer 2A), and 5-(1-bromo-8-chloroimidazo[1,5-a]pyrazin-3-yl)hexahydro-1H-cyclopropa[a]indolizin-2(1aH)-one (isomer 2B)

5-(1-bromo-8-((2,4-dimethoxybenzyl)amino)imidazo[1,5-a]pyrazin-3-yl)hexahydro-1H-cyclopropa[a]indolizin-2(1aH)-one (isomer 1) (300 mg, 0.585 mmol) was purified with chiral HPLC [SFC condition: Instrument: SFC-80; Column: AS 250×30 mm I.D., 20 um; Mobile phase: A: Supercritical CO$_2$, B: MeOH (0.1% NH$_3$H$_2$O), A:B=60:40 at 70 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.] to get trans-5-(1-bromo-8-((2,4-dimethoxybenzyl)amino)imidazo[1,5-a]pyrazin-3-yl)hexahydro-1H-cyclopropa[a]indolizin-2(1aH)-one (isomer 1A)(faster eluting): $^1$H NMR (400 MHz, CDCl$_3$) δ=7.24 (d, J=8.6 Hz, 1H), 7.10-7.06 (m, 1H), 7.06-7.01 (m, 1H), 6.73 (t, J=5.3 Hz, 1H), 6.47 (s, 1H), 6.42 (dd, J=2.0, 8.2 Hz, 1H), 4.65 (d, J=5.5 Hz, 2H), 4.13 (dd, J=3.3, 13.1 Hz, 1H), 3.86 (s, 3H), 3.78 (s, 3H), 3.67 (d, J=9.4 Hz, 1H), 2.87 (t, J=12.3 Hz, 1H), 2.72-2.62 (m, 1H), 2.12-2.03 (m, 2H), 2.00-1.93 (m, 3H), 1.40-1.27 (m, 1H), 1.03-0.97 (m, 1H), 0.71 (d, J=3.9 Hz, 1H). Acq Method AS-H_S_3_5_40_3ML_8MIN_15CM.M (Rt=4.848 min, 100% Area). 5-(1-bromo-8-((2,4-dimethoxybenzyl)amino)

imidazo[1,5-a]pyrazin-3-yl)hexahydro-1H-cyclopropa[a]indolizin-2(1aH)-one (isomer 1B) (slower eluting). ¹H NMR (400 MHz, CDCl₃) δ=7.25 (d, J=8.2 Hz, 1H), 7.10-7.07 (m, 1H), 7.06-7.02 (m, 1H), 6.74 (t, J=5.3 Hz, 1H), 6.48 (s, 1H), 6.43 (dd, J=1.6, 8.2 Hz, 1H), 4.65 (d, J=5.5 Hz, 2H), 4.14 (dd, J=3.7, 13.1 Hz, 1H), 3.87 (s, 3H), 3.78 (s, 3H), 3.68 (d, J=12.1 Hz, 1H), 2.87 (t, J=12.3 Hz, 1H), 2.71-2.63 (m, 1H), 2.12-2.04 (m, 2H), 2.01-1.92 (m, 3H), 1.39-1.30 (m, 1H), 1.04-0.96 (m, 1H), 0.71 (d, J=3.9 Hz, 1H). Acq Method AS-H_S_3_5_40_3ML_8MIN_15CM.M (Rt=4.977 min, 99.6% Area). 5-(1-bromo-8-((2,4-dimethoxybenzyl)amino) imidazo[1,5-a]pyrazin-3-yl)hexahydro-1H-cyclopropa[a]indolizin-2(1aH)-one (isomer 2) (150 mg, 0.293 mmol) was purified with chiral HPLC [SFC condition: Instrument: SFC-80; Column: AS 250×30 mm I.D.,10 um; Mobile phase: A: Supercritical CO₂, B: MeOH (0.1% NH₃H₂O), A:B=50:50 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.] to get Peak 1 5-(1-bromo-8-((2,4-dimethoxybenzyl)amino)imidazo[1,5-a]pyrazin-3-yl)hexahydro-1H-cyclopropa[a]indolizin-2(1aH)-one (isomer 2A): ¹H NMR (400 MHz, CDCl₃) δ=7.29-7.22 (m, 1H), 7.15-7.06 (m, 2H), 6.73 (t, J=5.1 Hz, 1H), 6.48 (s, 1H), 6.43 (dd, J=2.0, 8.2 Hz, 1H), 4.66 (d, J=5.5 Hz, 2H), 4.19 (dd, J=3.7, 13.1 Hz, 1H), 3.87 (s, 3H), 3.79 (s, 3H), 3.47 (d, J=10.6 Hz, 1H), 3.00-2.89 (m, 1H), 2.84-2.75 (m, 1H), 2.10 (d, J=6.3 Hz, 1H), 1.98 (dd, J=2.7, 12.9 Hz, 1H), 1.91 (br. s., 1H), 1.76-1.67 (m, 1H), 1.51-1.41 (m, 1H), 1.27-1.20 (m, 1H), 1.13-1.06 (m, 1H), 0.72 (d, J=3.5 Hz, 1H). Acq Method AS-H_S_3_5_40_3ML_8MIN_15CM.M (Rt=4.030 min, 90.1% Area). 5-(1-bromo-8-((2,4-dimethoxybenzyl)amino) imidazo[1,5-a]pyrazin-3-yl)hexahydro-1H-cyclopropa[a]indolizin-2(1aH)-one (isomer 2B): ¹H NMR (400 MHz, CDCl₃) δ=7.29-7.22 (m, 1H), 7.16-7.06 (m, 2H), 6.73 (t, J=5.1 Hz, 1H), 6.48 (s, 1H), 6.43 (dd, J=2.0, 8.2 Hz, 1H), 4.66 (d, J=5.5 Hz, 2H), 4.19 (dd, J=3.5, 12.9 Hz, 1H), 3.87 (s, 3H), 3.79 (s, 3H), 3.71 (q, J=6.8 Hz, 1H), 3.47 (d, J=9.4 Hz, 1H), 2.99-2.90 (m, 1H), 2.85-2.76 (m, 1H), 2.10 (d, J=6.3 Hz, 1H), 1.98 (dd, J=2.7, 12.9 Hz, 1H), 1.90 (br. s., 1H), 1.75-1.68 (m, 1H), 1.46 (dq, J=5.3, 12.1 Hz, 1H), 1.26-1.20 (m, 1H), 1.13-1.05 (m, 1H). Acq Method AS-H_S_3_5_40_3ML_8MIN_15CM.M (Rt=4.597 min, 95.97% Area).

Intermediate 29

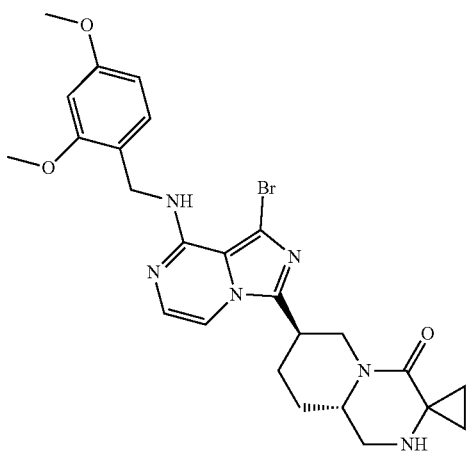 [SMILES: COc1ccc(CNc2nccn3c([C@@H]4CC[C@H]5CNC6(CC6)C(=O)N5C4)nc(Br)c23)c(OC)c1]

(7'R,9a'S)-7'-(1-bromo-8-((2,4-dimethoxybenzyl) amino)imidazo[1,5-a]pyrazin-3-yl)hexahydrospiro [cyclopropane-1,3'-pyrido[1,2-a]pyrazin]-4'(2'H)-one Step 1: (2S,5R)-tert-butyl 5-(1-bromo-8-((2,4-dimethoxybenzyl)amino)imidazo[1,5-a]pyrazin-3-yl)-2-(((1-(methoxycarbonyl)cyclopropyl)amino)methyl) piperidine-1-carboxylate To a solution of (2S,5R)-tert-butyl 5-(1-bromo-8-((2,4-dimethoxybenzyl)amino)imidazo[1,5-a]pyrazin-3-yl)-2-formylpiperidine-1-carboxylate (400 mg, 0.696 mmol) in MeOH (3 mL) was added methyl 1-aminocyclopropanecarboxylate (321 mg, 2.79 mmol), then followed by NaCNBH₃ (131 mg, 2.089 mmol) and acetic Acid (0.1 mL). The mixture was stirred at 18° C. for 2 h. Then to the reaction mixture was added to aq.NaHCO₃ (20 mL), extracted with DCM (25 mL×3). The organic layer was washed with brine, dried over Na₂SO₄, concentrated in vacuo and purified by silica gel chromatography (12 g, DCM:THF=100%~30%) to give (2S,5R)-tert-butyl 5-(1-bromo-8-((2,4-dimethoxybenzypamino)imidazo[1,5-a]pyrazin-3-yl)-2-(((1-(methoxycarbonyl)cyclopropyl)amino)methyl)piperidine-1-carboxylate. MS (ESI) m/z: 673/675 (M+1). Acq Method 0-60AB_2 min_220&254.1 cm (Rt=1.233 min). ¹H NMR (400 MHz, CD₃OD) δ=7.40 (d, J=5.1 Hz, 1H), 7.21 (d, J=8.2 Hz, 1H), 7.02 (d, J=5.1 Hz, 1H), 6.57 (s, 1H), 6.44 (dd, J=2.0, 8.2 Hz, 1H), 4.69-4.61 (m, 1H), 4.59-4.50 (m, 1H), 4.23 (br. s., 1H), 4.10-4.03 (m, 1H), 3.89 (s, 3H), 3.77 (s, 3H), 3.69-3.65 (m, 3H), 3.49-3.40 (m, 1H), 3.34 (br. s., 1H), 3.20-3.10 (m, 1H), 2.75 (dd, J=5.9, 11.7 Hz, 1H), 2.59 (br. s., 1H), 2.17-2.08 (m, 2H), 1.57-1.47 (m, 1H), 1.29-1.14 (m, 4H).

Step 2: (7R,9a'S)-7'-(1-bromo-8-((2,4-dimethoxybenzyl)amino)imidazo[1,5-a]pyrazin-3-yl)hexahydrospiro[cyclopropane-1,3'-pyrido[1,2-a]pyrazin]-4' (2'H)-one A solution of (2S,5R)-tert-butyl 5-(1-bromo-8-((2,4-dimethoxybenzyl)amino)imidazo[1,5-a]pyrazin-3-yl)-2-(((1-(methoxycarbonyl)cyclopropyl)amino)methyl)piperidine-1-carboxylate (350 mg, 0.520 mmol) in 4M HCl/Dioxane (2.60 mL, 10.39 mmol) was stirred at room temperature (15° C.) for 2 h. The mixture was concentrated in vacuo. The residue was dissolved into MeOH (4 mL) and K₂CO₃ (215 mg, 1.55 mmol) added. The mixture was stirred at 90° C. for 2 h, then filtered. The filtrate was concentrated in vacuo, and purified with silica gel column chromatography (THF/dichloromethane 0%~80%) to give the (7'R,9a'S)-7'-(1-bromo-8-((2,4-dimethoxybenzyl)amino)imidazo[1,5-a] pyrazin-3-yl)hexahydrospiro[cyclopropane-1,3'-pyrido[1,2-a]pyrazin]-4'(2'H)-one. MS (ESI) m/z: 541/543 (M+1). Acq Method 0-60AB_2 min_220&254.1 cm (Rt=1.001 min). ¹H NMR (400 MHz, CDCl₃) δ=7.50 (d, J=5.1 Hz, 1H), 7.21 (d, J=8.2 Hz, 1H), 7.04 (d, J=5.1 Hz, 1H), 6.58 (s, 1H), 6.47 (d, J=6.3 Hz, 1H), 4.80 (d, J=13.7 Hz, 1H), 4.60 (s, 2H), 3.90 (s, 3H), 3.78 (s, 3H), 3.65 (d, J=11.3 Hz, 1H), 3.18 (t, J=11.7 Hz, 1H), 2.92-2.76 (m, 2H), 2.14 (d, J=11.3 Hz, 1H), 1.92 (d, J=12.5 Hz, 2H), 1.69-1.57 (m, 1H), 1.41-1.27 (m, 2H), 1.22-1.13 (m, 1H), 0.87 (d, J=2.3 Hz, 2H) ppm.

Intermediate 30

(7'R,9a'S)-7'-(1-bromo-8-((2,4-dimethoxybenzyl)amino)imidazo[1,5-a]pyrazin-3-yl)-2'-methylhexahydrospiro[cyclopropane-1,3'-pyrido[1,2-a]pyrazin]-4'(2'H)-one

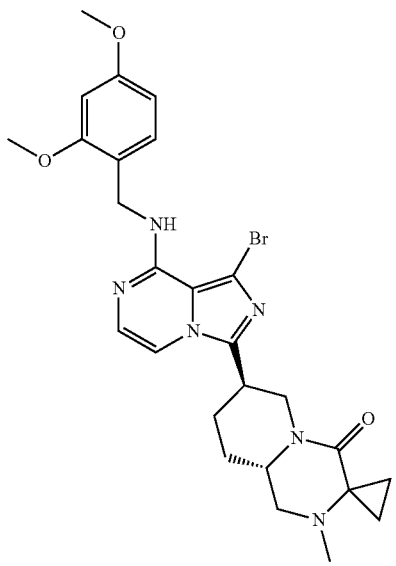 [SMILES: COc1ccc(CNc2nccn3c([C@@H]4CC[C@H]5CN(C)C6(CC6)C(=O)N5C4)nc(Br)c23)c(OC)c1]

To a solution of compound (7'R,9a'S)-7'-(1-bromo-8-((2,4-dimethoxybenzyl)amino)imidazo[1,5-a]pyrazin-3-yl)hexahydrospiro[cyclopropane-1,3'-pyrido[1,2-a]pyrazin]-4'(2'H)-one (120 mg, 0.222 mmol) in MeOH (5 mL) was added formaldehyde (0.165 mL, 2.216 mmol), NaCNBH$_3$ (69.6 mg, 1.108 mmol) and follow by acetic acid (0.2 mL). The mixture was stirred at 25° C. for 2 h, then pH was adjusted to 9 with aq. NaHCO$_3$, extracted with DCM (20 mL×3). The organic layer was washed with brine (20 mL), dried over Na$_2$SO$_4$, concentrated in vacuo to give the residue, which was purified with silica gel column chromatography (THF/dichloromethane 0%~80%) to give (7'R,9a'S)-7'-(1-bromo-8-((2,4-dimethoxybenzyl)amino)imidazo[1,5-a]pyrazin-3-yl)-2'-methylhexahydrospiro[cyclopropane-1,3'-pyrido[1,2-a]pyrazin]-4'(2'H)-one. MS (ESI) m/z: 555/557 (M+1). $^1$H NMR (400 MHz, CDCl$_3$) δ=7.58-7.55 (m, 1H), 7.48-7.43 (m, 1H), 7.39 (d, J=5.0 Hz, 1H), 7.03 (t, J=5.4 Hz, 1H), 6.78 (d, J=2.3 Hz, 1H), 6.73 (dd, J=2.5, 8.3 Hz, 1H), 5.28-5.22 (m, 1H), 4.96 (d, J=5.5 Hz, 2H), 4.17 (s, 3H), 4.14 (dd, J=2.8, 5.5 Hz, 1H), 4.09 (s, 3H), 3.48-3.33 (m, 2H), 3.27 (tt, J=3.9, 11.5 Hz, 1H), 3.00 (dd, J=11.7, 13.2 Hz, 1H), 2.78 (s, 3H), 2.48-2.34 (m, 2H), 2.25-2.12 (m, 2H), 1.89-1.84 (m, 1H), 1.43-1.36 (m, 1H), 1.21-1.16 (m, 2H) ppm.

Intermediate 31

(7'R,9a'S)-7'-(1-bromo-8-((2,4-dimethoxybenzyl)amino)imidazo[1,5-a]pyrazin-3-yl)-2'-ethylhexahydrospiro[cyclopropane-1,3'-pyrido[1,2-a]pyrazin]-4'(2'H)-one

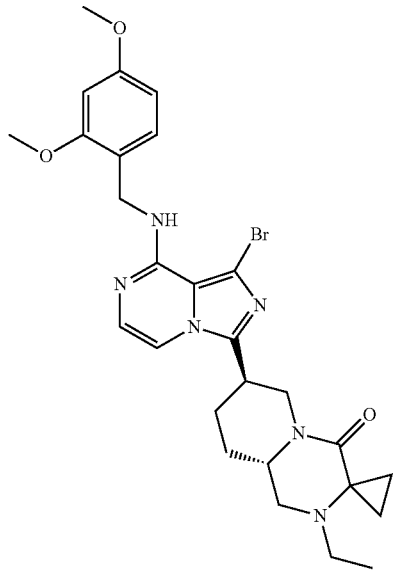 [SMILES: CCN1C[C@@H]2CC[C@@H](c3nc(Br)c4c(NCc5ccc(OC)cc5OC)nccn34)CN2C(=O)C12CC2]

To a solution of (7R,9a'S)-7'-(1-bromo-8-((2,4-dimethoxybenzyl)amino)imidazo[1,5-a]pyrazin-3-yl)hexahydrospiro[cyclopropane-1,3'-pyrido[1,2-a]pyrazin]-4'(2'H)-one (120 mg, 0.213 mmol) in MeOH (5 mL) was added acetaldehyde (94 mg, 2.128 mmol), NaCNBH$_3$ (66.9 mg, 1.064 mmol) and follow by Acetic Acid (0.2 mL). The mixture was stirred at 25° C. for 2 h, then pH was adjusted to 9 with aq. NaHCO$_3$, extracted with DCM (20 mL×3). The organic layer was washed with brine, dried over Na$_2$SO$_4$, concentrated in vacuo to give the residue, which was purified with silica gel column chromatography (THF/dichloromethane 0%~80%) to give (7R,9a'S)-7'-(1-bromo-8-((2,4-dimethoxybenzyl)amino)imidazo[1,5-a]pyrazin-3-yl)-2'-ethylhexahydrospiro[cyclopropane-1,3'-pyrido[1,2-a]pyrazin]-4'(2'H)-one. MS (ESI) m/z: 569/571 (M+1). method D (Rt=1.110 min). $^1$H NMR (400 MHz, CDCl$_3$) δ=7.27 (br. s., 1H), 7.17 (d, J=5.1 Hz, 1H), 7.10 (d, J=4.7 Hz, 1H), 6.75 (t, J=5.3 Hz, 1H), 6.49 (s, 1H), 6.44 (dd, J=2.0, 8.2 Hz, 1H), 5.30 (s, 2H), 4.91 (d, J=13.3 Hz, 1H), 4.66 (d, J=5.5 Hz, 2H), 4.59 (q, J=6.7 Hz, 1H), 3.88 (s, 3H), 3.80 (s, 3H), 3.75 (br. s., 1H), 3.30 (dd, J=5.3, 14.3 Hz, 1H), 3.04-2.93 (m, 2H), 2.75 (d, J=7.4 Hz, 1H), 2.71-2.63 (m, 1H), 2.19-2.06 (m, 2H), 1.91 (d, J=13.3 Hz, 1H), 1.60 (d, J=6.7 Hz, 3H), 1.46-1.38 (m, 1H), 1.29-1.20 (m, 1H), 0.91 (br. s., 1H) ppm.

Intermediate 32

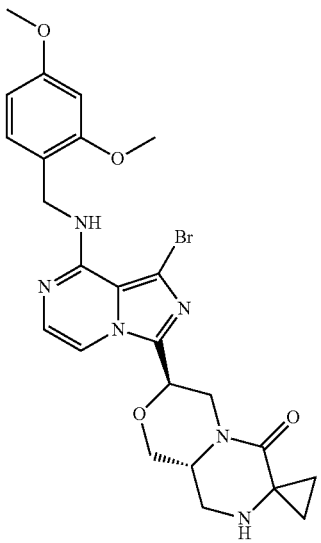 [SMILES: COc1ccc(CNc2nccn3c([C@H]4CN5C(=O)C6(CC6)NC[C@@H]5CO4)nc(Br)c23)c(OC)c1]

4-(8-amino-3-((3'R,9a'R)-6'-oxohexahydro-1'H-spiro [cyclopropane-1,7'-pyrazino[2,1-c][1,4]oxazin]-3'-yl)imidazo[1,5-a]pyrazin-1-yl)-3-ethoxy-N-(4-(trifluoromethyl)pyridin-2-yl)benzamide Step 1: (2R,5R)-tert-butyl 2-(1-bromo-8-((2,4-dimethoxybenzyl)amino)imidazo[1,5-a]pyrazin-3-yl)-5-(((1-(methoxycarbonyl)cyclopropyl)amino)methyl) morpholine-4-carboxylate To a solution of (2R,5S)-tert-butyl 2-(1-bromo-8-((2,4-dimethoxybenzyl)amino)imidazo[1,5-a]pyrazin-3-yl)-5-formylmorpholine-4-carboxylate (200 mg, 0.347 mmol) in MeOH (3 mL) was added methyl 1-aminocyclopropanecarboxylate (160 mg, 1.388 mmol), then followed by NaCNBH$_3$ (65.4 mg, 1.041 mmol) and acetic Acid (0.5 mL). The mixture was stirred at 25° C. for 2 h, then pH was adjusted to 9 with aq. NaHCO$_3$, extracted with DCM (20 mL×3). The organic layer was washed with brine, dried over Na$_2$SO$_4$, concentrated in vacuo and purified by silica gel chromatography (4 g, DCM:THF=100%~30%) to give (2R,5R)-tert-butyl 2-(1-bromo-8-((2,4-dimethoxybenzyl)amino) imidazo[1,5-a]pyrazin-3-yl)-5-(((1-(methoxycarbonyl)cyclopropyl)amino)methyl)morpholine-4-carboxylate. MS (ESI) m/z: 675/677 (M+1). method D (Rt=1.225 min). $^1$H NMR (400 MHz, CDCl$_3$)=7.44 (d, J=4.7 Hz, 1H), 7.09 (d, J=4.7 Hz, 1H), 6.75 (br. s., 1H), 6.49 (s, 1H), 6.44 (d, J=8.2 Hz, 1H), 5.00 (br. s., 1H), 4.67 (d, J=5.1 Hz, 2H), 3.88 (s, 4H), 3.80 (s, 3H), 3.69 (s, 3H), 3.64 (d, J=11.7 Hz, 1H), 3.50 (dd, J=4.1, 13.9 Hz, 1H), 3.26 (d, J=9.0 Hz, 1H), 3.19-3.10 (m, 1H), 3.02-2.92 (m, 1H), 1.57-1.50 (m, 9H), 1.50-1.41 (m, 2H), 1.32-1.22 (m, 2H), 0.98 (d, J=3.5 Hz, 1H).

Step 2: (3'R,9a'R)-3'-(1-bromo-8-((2,4-dimethoxybenzyl)amino)imidazo[1,5-a]pyrazin-3-yl)tetrahydro-1'H-spiro[cyclopropane-1,7'-pyrazino[2,1-c][1,4]oxazin]-6'(8'H)-one A solution of (2R,5R)-tert-butyl 2-(1-bromo-8-((2,4-dimethoxybenzyl)amino)imidazo[1,5-a]pyrazin-3-yl)-5-(((1-(methoxycarbonyl)cyclopropyl)amino)methyl)morpholine-4-carboxylate (80 mg, 0.118 mmol) in 4M HCl/Dioxane (0.030 mL, 0.118 mmol) was stirred at room temperature (15° C.) for 2 h. The mixture was concentrated in vacuo. The residue was dissolved into MeOH (2 mL) and treated with K$_2$CO$_3$ (49.1 mg, 0.355 mmol) at 90° C. for 2 hours. The mixture was filtered and filtrate concentrated in vacuo. The residue was purified with silica gel chromatography (THF/dichloromethane 0%~80%) to give (3'R,9a'R)-3'-(1-bromo-8-((2,4-dimethoxybenzyl)amino)imidazo[1,5-a]pyrazin-3-yl)tetrahydro-1'H-spiro[cyclopropane-1,7'-pyrazino[2,1-c][1,4]oxazin]-6'(8'H)-one. MS (ESI) m/z: 543/545 (M+1). method D (Rt=1.091 min). $^1$H NMR (400 MHz, CDCl$_3$) d=7.29 (br. s., 1H), 7.15 (d, J=4.7 Hz, 1H), 6.80 (br. s., 1H), 6.51 (s, 1H), 6.45 (d, J=8.2 Hz, 1H), 4.97 (dd, J=2.3, 13.7 Hz, 1H), 4.73 (dd, J=2.5, 10.8 Hz, 1H), 4.68 (d, J=5.5 Hz, 2H), 4.01 (dd, J=3.1, 11.3 Hz, 1H), 3.89 (s, 3H), 3.81 (s, 3H), 3.53-3.46 (m, 2H), 3.36-3.30 (m, 1H), 3.25 (dd, J=4.7, 13.3 Hz, 1H), 3.17-3.06 (m, 1H), 2.85 (dd, J=9.6, 13.9 Hz, 1H), 1.24-1.19 (m, 1H), 0.98-0.90 (m, 1H), 0.86 (dd, J=6.5, 10.0 Hz, 1H) ppm.

Intermediate 33, 34

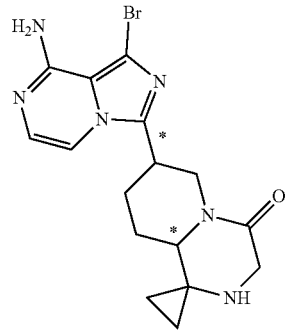

Trans, isomer 1

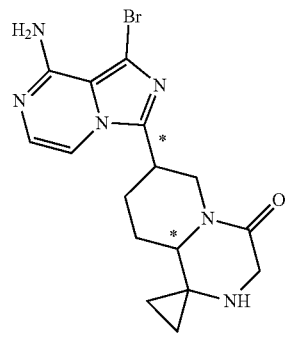

Trans, isomer 2

7'-(8-amino-1-bromoimidazo[1,5-a]pyrazin-3-yl) hexahydrospiro[cyclopropane-1,1'-pyrido[1,2-a] pyrazin]-4'(6'H)-one (trans isomer 1), and 7'-(8-amino-1-bromoimidazo[1,5-a]pyrazin-3-yl) hexahydrospiro[cyclopropane-1,1'-pyrido[1,2-a] pyrazin]-4'(6H)-one (trans isomer 2)

Step 1: benzyl benzyl (1-(5-bromopyridin-2-yl)cyclopropyl)carbamate

To a solution of 1-(5-bromopyridin-2-yl)cyclopropanecarboxylic acid (15 g, 62.0 mmol) in Toluene (150 mL) was added TEA (12.96 mL, 93 mmol) and DPPA (34.1 g, 124 mmol) and stirred at 15° C. for 30 mins, then heated to 90° C. for 2 hours. After cooling to room temperature, then to the reaction mixture was added benzylalcohol (33.5 g, 310 mmol) and mixture stirred at 90° C. for 3 hours. After cooling to room temperature, the reaction mixture washed with a saturated NaHCO₃ aqueous solution (50 mL×4). The organic layer was concentrated under reduced pressure, and the residue was purified by flash chromatography (ethyl acetate/Pet. ether=0%~50%) to give crude product. The residue was suspended in Pet. Ether and filtered to give benzyl benzyl (1-(5-bromopyridin-2-yl)cyclopropyl)carbamate. $^1$H NMR (400 MHz, CDCl₃) δ=8.47 (br. s., 1H), 7.71-7.56 (m, 1H), 7.37 (br. s., 4H), 7.24-7.02 (m, 2H), 5.50 (br. s., 1H), 5.12 (s, 2H), 1.61 (br. s., 2H), 1.35-1.21 (m, 2H) ppm.

Step 2: methyl 6-(1-(((benzyloxy)carbonyl)amino) cyclopropyl)nicotinate

To a solution of benzyl (1-(5-bromopyridin-2-yl)cyclopropyl)carbamate (6.0 g, 17.28 mmol) in MeOH (100 mL) and DMF (100 mL) was added TEA (7.23 mL, 51.8 mmol), DPPF (3.83 g, 6.91 mmol) and Pd(OAc)₂ (0.776 g, 3.46 mmol). The mixture was stirred at 80° C. for 48 hours under CO (50 psi), then filtered, and the filtrate was concentrated in vacuo. The residue was partitioned between water (100 mL) and EA (300 mL). The organic layer was washed with water (50 mL×3), brine (100 mL), dried over Na₂SO₄, and concentrated in vacuo. The residue was purified by silica gel column chromatography (EtOAc: Pet. Ether=0%~40%) to afford methyl 6-(1-(((benzyloxy)carbonyl)amino)cyclopropyl)nicotinate. $^1$H NMR (400 MHz, CDCl₃) δ=9.05 (d, J=1.5 Hz, 1H), 8.18 (d, J=7.5 Hz, 1H), 7.48-7.30 (m, 5H), 7.26-7.14 (m, 1H), 5.56 (br. s., 1H), 5.19-5.13 (m, 2H), 3.94 (s, 3H), 1.81-1.72 (m, 2H), 1.39 (br. s., 2H) ppm.

Step 3: methyl 6-(1-(((benzyloxy)carbonyl)amino) cyclopropyl)piperidine-3-carboxylate To a solution of methyl 6-(1-(((benzyloxy)carbonyl)amino)cyclopropyl)nicotinate (700 mg, 2.145 mmol) in AcOH (10 mL) was added sodium cyanoborohydride (472 mg, 7.51 mmol) in portions. The mixture was stirred at 30° C. for 24 hours, then poured into a saturated aqueous NaHCO₃(50 mL). The mixture was a extracted with EtOAc (30 mL×4). The combined organic layers were washed with brine (50 mL) The extracts were dried over Na₂SO₄, filtered and concentrated under reduced pressure to give crude methyl 6-(1-(((benzyloxy)carbonyl)amino)cyclopropyl)piperidine-3-carboxylate. MS: 333.3 (M+1).

Step 4: methyl 6-(1-(((benzyloxy)carbonyl)amino) cyclopropyl)-1-(2-chloroacetyl) piperidine-3-carboxylate To a solution of methyl 6-(1-(((benzyloxy)carbonyl)amino)cyclopropyl)piperidine-3-carboxylate (600 mg, 1.805 mmol) in THF (6 mL) was added TEA (0.277 mL, 1.986 mmol) and 2-chloroacetyl chloride (224 mg, 1.986 mmol). The mixture was stirred at 0° C. for 3 h. Then the reaction mixture was diluted with EtOAc (10 mL) and washed with water (5 mL×3), brine (10 mL), dried over Na₂SO₄, and concentrated in vacuo. The residue was purified by silica gel column chromatography (12 g, THF: Pet. ether=0%~40%) to afford methyl 6-(1-(((benzyloxy)carbonyl)amino)cyclopropyl)-1-(2-chloroacetyl)piperidine-3-carboxylate. $^1$H NMR (400 MHz, CDCl₃) δ=7.34 (br. s., 5H), 5.29-5.14 (m, 1H), 5.03 (br. s., 2H), 4.41 (d, J=12.9 Hz, 1H), 4.19 (br. s., 1H), 4.04-3.90 (m, 1H), 3.72-3.65 (m, 3H), 3.61 (d, J=11.7 Hz, 1H), 2.72-2.50 (m, 1H), 1.98 (br. s., 1H), 1.84-1.62 (m, 3H), 1.14-0.69 (m, 5H) ppm.

Step 5: 2'-benzyl 7'-methyl 4'-oxohexahydrospiro [cyclopropane-1,1'-pyrido[1,2-a]pyrazine]-2',7'(6'H)-dicarboxylate (trans)

To a solution of methyl 6-(1-(((benzyloxy)carbonyl)amino)cyclopropyl)-1-(2-chloroacetyl)piperidine-3-carboxylate (100 mg, 0.245 mmol) in DMF (2 mL) was added Cs₂CO₃ (239 mg, 0.734 mmol). The mixture was stirred at 70° C. for 2 hours, then poured into water (10 mL) and extracted with EtOAc (10 mL×4). The combined organic layers were washed with water (5 mL×3), brine (10 mL), dried over Na₂SO₄, and concentrated under reduced pressure. The residue was purified by silica gel column chromatography (4 g, EtOAc: Pet. ether=0%~80%) to afford trans-2'-benzyl 7'-methyl 4'-oxohexahydrospiro[cyclopropane-1,1'-pyrido[1,2-a]pyrazine]-2',7'(6'H)-dicarboxylate. $^1$H NMR (400 MHz, CD₃OD) δ=7.36 (br. s., 5H), 5.12 (br. s., 2H), 4.78 (dd, J=2.0, 12.9 Hz, 1H), 4.51 (d, J=17.2 Hz, 1H), 3.86 (d, J=8.6 Hz, 1H), 3.67 (s, 3H), 2.76 (br. s., 1H), 2.62 (t, J=12.5 Hz, 1H), 2.38 (ddd, J=4.1, 8.2, 11.9 Hz, 1H), 2.10 (d, J=11.0 Hz, 1H), 1.82 (br. s., 1H), 1.68-1.54 (m, 1H), 1.53-1.32 (m, 2H), 1.18-1.05 (m, 1H), 0.94-0.77 (m, 2H) ppm.

Step 6: 2'-((benzyloxy)carbonyl)-4'-oxooctahydrospiro[cyclopropane-1,1'-pyrido[1,2-a]pyrazine]-7'-carboxylic acid (trans)

To a solution of 2'-benzyl 7'-methyl 4'-oxohexahydrospiro[cyclopropane-1,1'-pyrido[1,2-a]pyrazine]-2',7'(6'H)-dicarboxylate (120 mg, 0.322 mmol) in THF (3 mL) was added lithium hydroxide in H₂O (0.483 mL, 0.483 mmol). The mixture was stirred at 15° C. for 1.5 h. The reaction mixture was diluted with water (10 mL). The pH of the reaction mixture was adjusted to 3 with aq. HCl (1M). The mixture was extracted with EtOAc (10 mL×4). Then the organic layer was washed with brine (30 mL), dried over Na₂SO₄, and concentrated under reduced pressure to afford 2'-((benzyloxy)carbonyl)-4'-oxooctahydrospiro[cyclopropane-1,1'-pyrido[1,2-a]pyrazine]-7'-carboxylic acid. $^1$H NMR (400 MHz, CDCl₃) δ=7.35 (br. s., 5H), 5.12 (br. s., 2H), 4.95 (d, J=12.5 Hz, 1H), 4.74-4.48 (m, 1H), 3.85 (br. s., 1H), 2.58 (t, J=12.5 Hz, 2H), 2.52-2.40 (m, 1H), 2.28-2.13 (m, 1H), 1.87 (br. s., 1H), 1.70-1.44 (m, 3H), 1.04 (br. s., 1H), 0.96-0.72 (m, 2H) ppm.

Step 7: benzyl 7'-(((3-chloropyrazin-2-yl)methyl) carbamoyl)-4'-oxohexahydrospiro[cyclopropane-1, 1'-pyrido[1,2-a]pyrazine]-2'(6'H)-carboxylate (trans)

To a solution of 2'-((benzyloxy)carbonyl)-4'-oxooctahydrospiro[cyclopropane-1,1'-pyrido[1,2-a]pyrazine]-7'-carboxylic acid (100 mg, 0.279 mmol) in DMF (3 mL) was added HATU (117 mg, 0.307 mmol), DIEA (0.146 mL, 0.837 mmol) and (3-chloropyrazin-2-yl)methanamine hydrochloride (55.3 mg, 0.307 mmol) and the mixture was stirred for 16 hrs at 15° C. The mixture was diluted with water (15 mL) and extracted with ethyl acetate (10 mL×4). The combined organic layers were washed with water (5 mL×3), brine (10 mL), dried over Na₂SO₄, and evaporated to give the crude product which was purified on flash chromatography (Pet. ether/EtOAc=100%~60%) to give benzyl 7'-(((3-chloropyrazin-2-yl)methyl)carbamoyl)-4'-oxohexahydrospiro[cyclopropane-1,1'-pyrido[1,2-a]pyrazine]-2'(6'H)-carboxylate. $^1$H NMR (400 MHz, CDCl$_3$) δ=8.45 (d, J=2.0 Hz, 1H), 8.34 (s, 1H), 7.35 (s, 5H), 6.92 (br. s., 1H), 5.13 (br. s., 2H), 4.90-4.80 (m, 1H), 4.73-4.53 (m, 3H), 3.84 (br. s., 1H), 3.22-2.98 (m, 1H), 2.75-2.51 (m, 2H), 2.39 (t, J=11.5 Hz, 1H), 2.04 (s, 1H), 1.92-1.86 (m, 1H), 1.57-1.44 (m, 2H), 1.06 (br. s., 1H), 0.91-0.75 (m, 2H) ppm.

Step 8: benzyl 7'-(8-chloroimidazo[1,5-a]pyrazin-3-yl)-4'-oxohexahydrospiro[cyclopropane-1,1'-pyrido[1,2-a]pyrazine]-2'(6'H)-carboxylate (trans)

To a stirred solution of benzyl 7'-(((3-chloropyrazin-2-yl)methyl)carbamoyl)-4'-oxohexahydrospiro[cyclopropane-1,1'-pyrido[1,2-a]pyrazine]-2'(6'H)-carboxylate (1.8 g, 3.72 mmol) in Acetonitrile (18 mL) was added PCl$_5$ (0.775 g, 3.72 mmol), and the reaction mixture was stirred at 15° C. for 3 hours. The reaction mixture was poured slowly to a saturated aq. NaHCO$_3$ (100 mL) at 0° C. The mixture was extracted with ethyl acetate (50 mL×4). The combined organic layers were washed with brine (10 mL), dried over Na$_2$SO$_4$, evaporated to give a product which was purified on flash chromatography (20 g Pet. ether/EtOAc=100%~20%) to give benzyl 7'-(8-chloroimidazo[1,5-a]pyrazin-3-yl)-4'-oxohexahydrospiro[cyclopropane-1,1'-pyrido[1,2-a]pyrazine]-2'(6'H)-carboxylate. $^1$H NMR (400 MHz, CD$_3$OD) δ=8.18 (d, J=4.7 Hz, 1H), 7.86 (s, 1H), 7.46-7.27 (m, 6H), 5.16 (br. s., 2H), 4.80 (d, J=11.3 Hz, 1H), 4.60 (d, J=15.7 Hz, 1H), 3.94 (br. s., 1H), 2.96 (d, J=12.5 Hz, 1H), 2.81 (s, 2H), 2.16 (br. s., 1H), 1.98 (d, J=11.0 Hz, 2H), 1.56 (br. s., 2H), 1.20 (d, J=8.2 Hz, 1H), 0.98-0.87 (m, 2H) ppm.

Step 9: benzyl 7'-(1-bromo-8-chloroimidazo[1,5-a]pyrazin-3-yl)-4'-oxohexahydrospiro[cyclopropane-1,1'-pyrido[1,2-a]pyrazine]-2'(6'H)-carboxylate (trans)

To a solution of benzyl 7'-(8-chloroimidazo[1,5-a]pyrazin-3-yl)-4'-oxohexahydrospiro[cyclopropane-1,1'-pyrido[1,2-a]pyrazine]-2'(6'H)-carboxylate (1.4 g, 3.00 mmol) in acetonitrile (14 mL) was added NBS (0.588 g, 3.31 mmol). The resulting mixture was stirred at 15° C. for 1 hour, then poured into a saturated aqueous NaHCO$_3$ (10 mL) and extracted with EtOAc (10 mL×3). The combined organic layers were washed with brine (10 mL), dried over Na$_2$SO$_4$, filtered and concentrated in vacuo. The residue was purified by silica gel column chromatography (4 g Pet. ether/EtOAc=100%~0%) to afford benzyl 7'-(1-bromo-8-chloroimidazo[1,5-a]pyrazin-3-yl)-4'-oxohexahydrospiro[cyclopropane-1,1'-pyrido[1,2-a]pyrazine]-2'(6'H)-carboxylate. $^1$H NMR (400 MHz, CD$_3$OD) δ=8.15 (d, J=4.7 Hz, 1H), 7.50-7.22 (m, 6H), 5.15 (br. s., 2H), 4.76 (d, J=12.9 Hz, 1H), 4.58 (d, J=17.6 Hz, 1H), 3.93 (br. s., 1H), 2.96-2.89 (m, 1H), 2.84 (s, 2H), 2.15 (br. s., 1H), 1.95 (d, J=11.0 Hz, 2H), 1.73-1.50 (m, 2H), 1.25-1.14 (m, 1H), 0.92 (dd, J=3.3, 6.1 Hz, 2H) ppm.

Step 10: benzyl 7'-(1-bromo-8-((2,4-dimethoxybenzyl)amino)imidazo[1,5-a]pyrazin-3-yl)-4'-oxohexahydrospiro[cyclopropane-1,1'-pyrido[1,2-a]pyrazine]-2'(6'H)-carboxylate (trans isomer 1) and benzyl 7'-(1-bromo-8-((2,4-dimethoxybenzyl)amino)imidazo[1,5-a]pyrazin-3-yl)-4'-oxohexahydrospiro[cyclopropane-1,1'-pyrido[1,2-a]pyrazine]-2'(6'H)-carboxylate (trans isomer 2)

To a solution of benzyl 7'-(1-bromo-8-chloroimidazo[1,5-a]pyrazin-3-yl)-4'-oxohexahydrospiro[cyclopropane-1,1'-pyrido[1,2-a]pyrazine]-2'(6'H)-carboxylate (900 mg, 1.652 mmol) in DMF (9 mL) was added K$_2$CO$_3$ (685 mg, 4.96 mmol) and (2,4-dimethoxyphenyl)methanamine (414 mg, 2.478 mmol). The mixture was stirred at 90° C. for 2 hours. The reaction mixture was diluted with EtOAc (100 mL) then washed with water (10 mL×4) and brine (40 mL), dried over Na$_2$SO$_4$, filtered and concentrated under reduced pressure. The residue was purified by silica gel column chromatography (4 g Pet. ether/THF=100%~30%) and SFC (Instrument: Thar SFC 200; Column: AS 300 mm×50 mm, 10 um; Mobile phase: A: Supercritical CO$_2$, B: MeOH (0.1% NH$_3$H$_2$O), A:B=55:45 at 200 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give two trans isomers. Benzyl 7'-(1-bromo-8-((2,4-dimethoxybenzyl)amino)imidazo[1,5-a]pyrazin-3-yl)-4'-oxohexahydrospiro[cyclopropane-1,1'-pyrido[1,2-a]pyrazine]-2'(6'H)-carboxylate(trans enantiomer 1): Rt=4.820 min. $^1$H NMR (400 MHz, CD$_3$OD) δ=7.44 (d, J=5.1 Hz, 1H), 7.41-7.26 (m, 5H), 7.19 (d, J=8.2 Hz, 1H), 7.02 (d, J=5.1 Hz, 1H), 6.56 (d, J=2.0 Hz, 1H), 6.45 (dd, J=2.3, 8.2 Hz, 1H), 5.12 (br. s., 2H), 4.71 (d, J=13.3 Hz, 1H), 4.57 (s, 3H), 3.87 (s, 3H), 3.76 (s, 3H), 3.19-3.11 (m, 1H), 2.93-2.77 (m, 2H), 2.07 (br. s., 1H), 1.88 (d, J=11.0 Hz, 2H), 1.54 (d, J=10.2 Hz, 3H), 1.17-1.13 (m, 1H), 0.89 (d, J=7.4 Hz, 2H) ppm. MS: 677.2 (M+1). Benzyl 7'-(1-bromo-8-((2,4-dimethoxybenzyl)amino)imidazo[1,5-a]pyrazin-3-yl)-4'-oxohexahydrospiro[cyclopropane-1,1'-pyrido[1,2-a]pyrazine]-2'(6'H)-carboxylate (trans enantiomer 2). Rt=5.643 min. $^1$H NMR (400 MHz, CD$_3$OD) δ=7.50-7.27 (m, 6H), 7.21 (d, J=8.2 Hz, 1H), 7.03 (d, J=5.1 Hz, 1H), 6.57 (d, J=2.0 Hz, 1H), 6.46 (dd, J=2.3, 8.2 Hz, 1H), 5.14 (br. s., 2H), 4.73 (d, J=11.3 Hz, 1H), 4.59 (s, 3H), 3.89 (s, 3H), 3.78 (s, 3H), 3.20-3.12 (m, 1H), 2.95-2.79 (m, 2H), 2.09 (br. s., 1H), 1.96-1.83 (m, 2H), 1.72-1.42 (m, 3H), 1.17 (d, J=7.0 Hz, 1H), 0.90 (d, J=7.4 Hz, 2H) ppm. MS: 677.2 (M+1).

Step 11: benzyl7'-(8-amino-1-bromoimidazo[1,5-a]pyrazin-3-yl)-4'-oxohexahydrospiro[cyclopropane-1,1'-pyrido[1,2-a]pyrazine]-2'(6'H)-carboxylate (trans isomer 1) and benzyl7'-(8-amino-1-bromoimidazo[1,5-a]pyrazin-3-yl)-4'-oxohexahydrospiro[cyclopropane-1,1'-pyrido[1,2-a]pyrazine]-2'(6'H)-carboxylate (trans isomer 2)

A solution of benzyl 7'-(1-bromo-8-((2,4-dimethoxybenzyl)amino)imidazo[1,5-a]pyrazin-3-yl)-4'-oxohexahydrospiro[cyclopropane-1,1'-pyrido[1,2-a]pyrazine]-2'(6'H)-carboxylate (trans isomer 1) (100 mg, 0.148 mmol) in TFA (3 mL) was stirred at 90° C. for 2 hours under N$_2$ atmosphere. The mixture was concentrated in vacuo to give 7'-(8-amino-1-bromoimidazo[1,5-a]pyrazin-3-yl)hexahydrospiro[cyclopropane-1,1'-pyrido[1,2-a]pyrazin]-4'(6'H)-one as TFA salt. MS: 391.3/393.3 (M+1).

Starting from benzyl 7'-(1-bromo-8-((2,4-dimethoxybenzyl)amino)imidazo[1,5-a]pyrazin-3-yl)-4'-oxohexahydrospiro[cyclopropane-1,1'-pyrido[1,2-a]pyrazine]-2'(6'H)-carboxylate (trans isomer 2), benzyl7'-(8-amino-1-bromoimidazo[1,5-a]pyrazin-3-yl)-4'-oxohexahydrospiro[cyclopropane-1,1'-pyrido[1,2-a]pyrazine]-2'(6'H)-carboxylate (trans isomer 2) was obtained using the same procedure. MS: 391.3/393.3 (M+1).

Intermediate 35

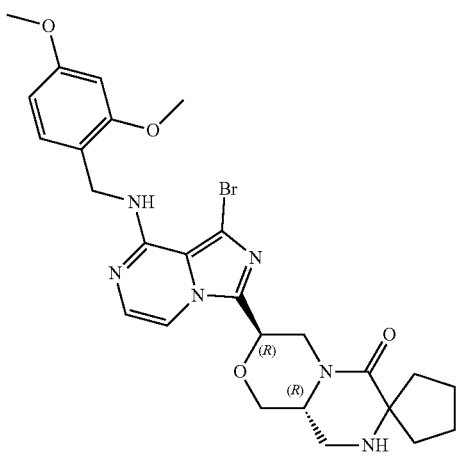

(3'R,9a'R)-3'-(1-bromo-8-((2,4-dimethoxybenzyl)amino)imidazo[1,5-a]pyrazin-3-yl)tetrahydro-1'H-spiro[cyclopentane-1,7'-pyrazino[2,1-c][1,4]oxazin]-6'(8'H)-one Step 1:(2R,5R)-tert-butyl 2-(1-bromo-8-((2,4-dimethoxybenzyl)amino)imidazo[1,5-a]pyrazin-3-yl)-5-(((1-(methoxycarbonyl)cyclopentyl)amino)methyl)morpholine-4-carboxylate To a solution of (2R,5S)-tert-butyl 2-(1-bromo-8-((2,4-dimethoxybenzyl)amino)imidazo[1,5-a]pyrazin-3-yl)-5-formylmorpholine-4-carboxylate (120 mg, 0.208 mmol), methyl 1-aminocyclopentanecarboxylate (44.7 mg, 0.312 mmol), and sodium cyanoborohydride (39.2 mg, 0.625 mmol) in DCM (3 mL) was added acetic acid (0.1 mL). The mixture was stirred at 20° C. for 12 hrs under $N_2$, then poured into 20 mL of sat. aq. NaHCO$_3$, and extracted with DCM (10 mL×3). The organic layer was washed with brine (10 mL), dried over Na$_2$SO$_4$, evaporated to get the crude product, which was purified by flash chromatography (Pet. ether/THF=65~50%) to afford the title compound. $^1$H NMR (400 MHz, CDCl$_3$) δ=7.42 (d, J=5.1 Hz, 1H), 7.26-7.23 (m, 1H), 7.07 (d, J=5.1 Hz, 1H), 6.73 (t, J=5.3 Hz, 1H), 6.47 (s, 1H), 6.42 (dd, J=2.0, 8.2 Hz, 1H), 4.98 (d, J=3.5 Hz, 1H), 4.71-4.61 (m, 3H), 3.85 (s, 4H), 3.80-3.75 (m, 3H), 3.70 (s, 3H), 3.67 (br. s., 1H), 3.44 (dd, J=4.5, 13.9 Hz, 1H), 3.25 (dd, J=2.9, 11.5 Hz, 1H), 2.76 (dd, J=3.1, 7.0 Hz, 2H), 2.11-2.02 (m, 2H), 1.84-1.81 (m, 2H), 1.77-1.71 (m, 2H), 1.67 (br. s., 9H), 1.60-1.55 (m, 2H) ppm.

Step 2: (3'R,9a'R)-3'-(1-bromo-8-((2,4-dimethoxybenzyl)amino)imidazo[1,5-a]pyrazin-3-yl)tetrahydro-1'H-spiro[cyclopentane-1,7'-pyrazino[2,1-c][1,4]oxazin]-6'(8'H)-one A mixture of (2R,5R)-tert-butyl 2-(1-bromo-8-((2,4-dimethoxybenzyl)amino)imidazo[1,5-a]pyrazin-3-yl)-5-(((1-(methoxycarbonyl)cyclopentyl)amino)methyl)morpholine-4-carboxylate (50 mg, 0.047 mmol) in 4M HCl/Dioxane (2 mL, 8.00 mmol) was stirred at 20° C. for 2 hours. After removal of all solvent, the residue was dissolved with sat. aq. NaHCO$_3$ (10 mL) and extracted with DCM/i-PrOH (10 mL×3). The organic layer was washed with brine (10 mL), dried over Na$_2$SO$_4$, evaporated. The residue was dissolved in MeOH (3 mL) and heated at 80° C. for 12 hours under $N_2$. The mixture was concentrated to afford the title compound, which was used in the next step directly. $^1$H NMR (400 MHz, CDCl$_3$) δ=7.22 (br. s., 1H), 7.18-7.16 (m, 1H), 7.06 (d, J=5.1 Hz, 1H), 6.72 (br. s., 1H), 6.43 (br. s., 1H), 6.38 (d, J=8.2 Hz, 1H), 4.86 (d, J=16.0 Hz, 1H), 4.67-4.58 (m, 3H), 3.92-3.87 (m, 1H), 3.81 (s, 3H), 3.74 (s, 3H), 3.69-3.61 (m, 2H), 3.38 (t, J=11.0 Hz, 1H), 3.18 (dd, J=11.0, 13.7 Hz, 1H), 3.08 (dd, J=4.9, 13.5 Hz, 1H), 2.71 (dd, J=9.0, 13.3 Hz, 1H), 2.31 (d, J=5.9 Hz, 1H), 1.98 (br. s., 2H), 1.74 (d, J=12.1 Hz, 2H), 1.69 (d, J=7.4 Hz, 2H). ppm Example 1

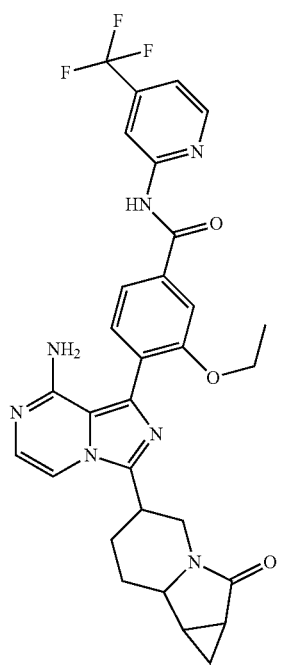

4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide (1)

Step 1: 4-(8-((2,4-dimethoxybenzyl)amino)-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide (isomer 1A)

To a solution of 5-(1-bromo-8-((2,4-dimethoxybenzyl)amino)imidazo[1,5-a]pyrazin-3-yl)hexahydro-1H-cyclopropa[a]indolizin-2(1aH)-one (isomer 1A) (30 mg, 0.059 mmol) in 2.5 mL of DMF/dioxane/H$_2$O (2:2:1) was added 3-ethoxy-4-(4,4,5,5-tetramethyl-1,3,2-dioxaborolan-2-yl)-N-(5-(trifluoromethyl)pyridin-2-yl)benzamide (30.6 mg, 0.070 mmol), K$_2$CO$_3$ (24.28 mg, 0.176 mmol) and PdCl$_2$(dppf) (4.28 mg, 5.85 μmol) under nitrogen protection. Then the mixture was heated to 80° C. for 4 hour, then poured into H$_2$O (10 mL), extracted with DCM (15 mL×3). The organic layer was washed with brine, dried over Na$_2$SO$_4$, concentrated in vacuo to give the crude product 4-(8-((2,4-dimethoxybenzyl)amino)-3-(2-oxooctahydro-1H-cyclopropa[a]

indolizin-5-yl)imidazo[1,5-a]pyrazin-1-yl)-3-ethoxy-N-(5-(trifluoromethyl)pyridin-2-yl)benzamide used to the next step without further purification. MS (ESI): 742.2 (M+1). method D (Rt=1.310 min).

Step 2: 4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide (isomer 1A)

A solution of 4-(8-((2,4-dimethoxybenzy)amino)-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide (55 mg, 0.052 mmol) in TFA (3 mL) was stirred at 90° C. for 2 h. TLC showed the starting materials was consumed and concentrated in vacuo. The residue was purified with preparative HPLC with Waters XSELECT C18 1509×30 mm×5 um. Gradient: 22-52% 15 min; FlowRate: 25 ml/min to get the product 4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide (isomer 1A). $^1$H NMR (400 MHz, CD$_3$OD) δ=8.67-8.63 (m, 2H), 7.86 (d, J=6.0 Hz, 1H), 7.81-7.77 (m, 2H), 7.73-7.69 (m, 1H), 7.49-7.46 (m, 1H), 7.01 (d, J=6.0 Hz, 1H), 4.28 (q, J=6.9 Hz, 2H), 4.16 (d, J=10.3 Hz, 1H), 3.91-3.83 (m, 1H), 3.20-3.08 (m, 2H), 2.23-2.13 (m, 3H), 2.04-1.94 (m, 2H), 1.62-1.51 (m, 1H), 1.36 (t, J=6.9 Hz, 3H), 1.12 (dt, J=4.8, 8.0 Hz, 1H), 0.87-0.81 (m, 1H) ppm. MS (ESI): 592.1 (M+1). method C (Rt=2.567 min). Chiral SFC: Acq Method OD-H_3_5_40_2,35ML.M (Rt=9.417 min, 99.65% Area).

Example 2

4-(8-amino-3-((6'S,8a'R)-1',1'-difluoro-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide (2) and 4-(8-amino-3-((6'R,8a'S)-1',1'-difluoro-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide (3)

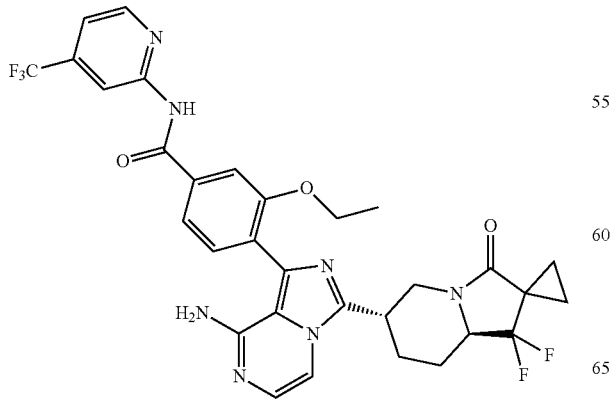

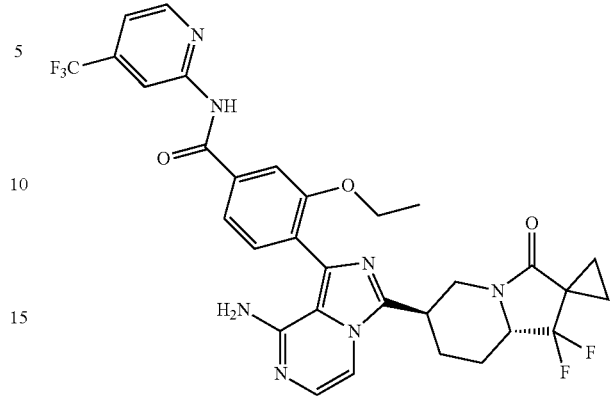

To a 40 mL vial was added (6'R,8a'S)-6'-(8-amino-1-bromoimidazo[1,5-a]pyrazin-3-yl)-1',1'-difluorotetrahydro-1H-spiro[cyclopropane-1,2'-indolizin]-3'(5'H)-one (50 mg, 0.121 mmol), 3-ethoxy-4-(4,4,5,5-tetramethyl-1,3,2-dioxaborolan-2-yl)-N-(4-(trifluoromethyl)pyridin-2-yl)benzamide (79 mg, 0.182 mmol), and PdCl$_2$(dppf)-CH$_2$Cl$_2$ Adduct (9.91 mg, 0.012 mmol). The flask was degassed by vacuum and re-filled with N$_2$. Then K$_2$CO$_3$ (2M, 243 µl, 0.485 mmol) and Dioxane (2426 µl) were added. The reaction was stirred at 80° C. for 2 hours. After cooling down to room temperature, the solution was diluted with EtOAc and dried over anhydrous Na$_2$SO$_4$, filtered, and concentrated. The product was purified by SiO$_2$ chromatography (12 g, EtOAc in Hexane 0% to 100%) to give a mixture of the title compounds. The two isomers were separated by chiral SFC separation to give the two title compounds. SFC conditions: Column: AS-H (2×25 cm); Mobile pahse: 30% methanol (0.1% DEA)/CO$_2$, 100 bar, 60 mL/min, 220 nm; inj vol.: 0.75 mL, 7 mg/mL methanol.

Example 3

4-(8-amino-3-((6'R,8a'S)-3'-oxohexahydro-1'H-spiro[cyclopropane-1,2'-indolizin]-6'-yl)imidazo[1,5-a]pyrazin-1-yl)-3-ethoxy-5-fluoro-N-(4-(trifluoromethyl)pyridin-2-yl)benzamide (4)

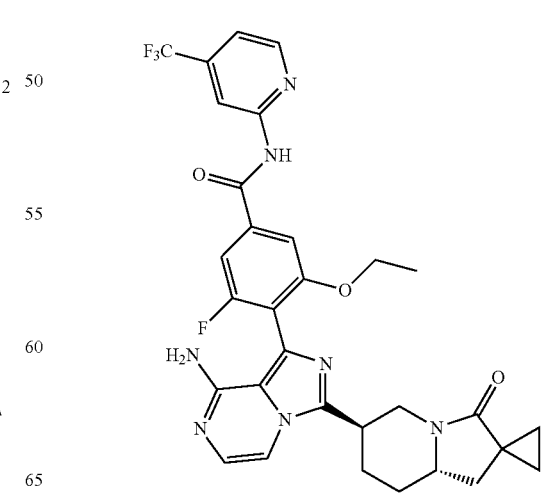

To a 8 mL vial was added 3-ethoxy-5-fluoro-4-(4,4,5,5-tetramethyl-1,3,2-dioxaborolan-2-yl)-N-(4-(trifluoromethyl)pyridin-2-yl)benzamide (24.14 mg, 0.053 mmol), (6'R,8a'S)-6'-(8-amino-1-bromoimidazo[1,5-a]pyrazin-3-yl)tetrahydro-1'H-spiro[cyclopropane-1,2'-indolizin]-3'(5'H)-one (10 mg, 0.027 mmol), and PALLADIUM(II) ACETATE/1,1'-BIS(DI-T-BUTYLPHOSPHINO)FERROCENE/POTASSIUM PHOSPHATE ADMIXTURE (4.84 mg, 5.32 μmol). The flask was degassed by vacuum and re-filled with $N_2$. Then $K_2CO_3$ (2M, 39.9 μl, 0.080 mmol) and Dioxane (532 μl) were added. The reaction was stirred at 90° C. for 16 hours. The solvent was removed by blowing $N_2$ for 30 min. The residue was dissolved in 2 mL DMF and purified by C18 column (Gilson, $CH_3CN$ in water with 0.1% TFA: 0% to 90%) to the title compound.

The following compounds were prepared based on the same procedures as described in examples 1, 2, and 3 using different bromide and boronic ester intermediates for the Suzuki coupling step.

TABLE 1

| Comp # | Structure | IUPAC Name | Exact Mass [M + H]+ |
|---|---|---|---|
| 5 | 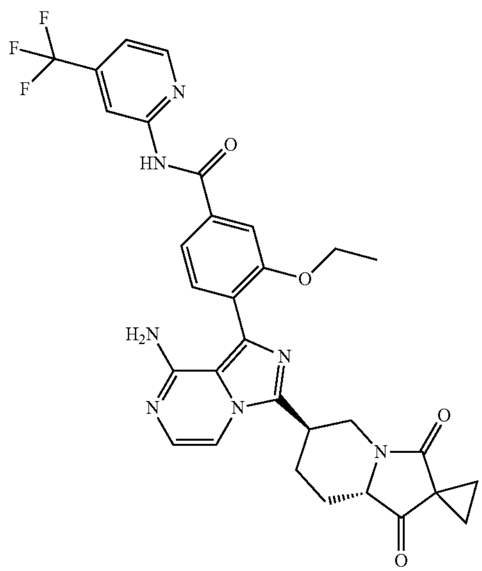 [SMILES: CCOc1cc(C(=O)Nc2cc(C(F)(F)F)ccn2)ccc1-c1nc([C@@H]2CC[C@H]3C(=O)C4(CC4)C(=O)N3C2)n2ccnc(N)c12] | 4-{8-amino-3-[(6'R,8a'S)-1',3'-dioxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide | Calc'd 620.0, found 620.29 |
| 6 | 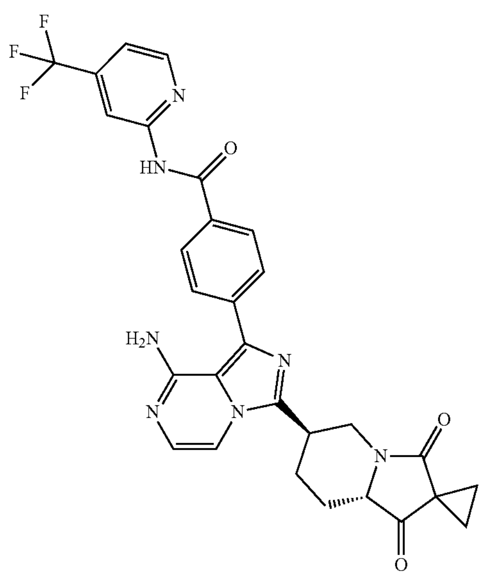 [SMILES: Nc1nccn2c([C@@H]3CC[C@H]4C(=O)C5(CC5)C(=O)N4C3)nc(-c3ccc(C(=O)Nc4cc(C(F)(F)F)ccn4)cc3)c12] | 4-{8-amino-3-[(6'R,8a'S)-1',3'-dioxohexahydrospiro[cyclopropane-1,2'-indolizin]-6'-yl]imidazo[1,5-a]pyrazin-1-yl}-N-[4-(trifluoromethyl)pyridin-2-yl]benzamide | Calc'd 576.0, found 576.28 |

TABLE 1-continued

| Comp # | Structure | IUPAC Name | Exact Mass [M + H]+ |
|---|---|---|---|
| 7 | 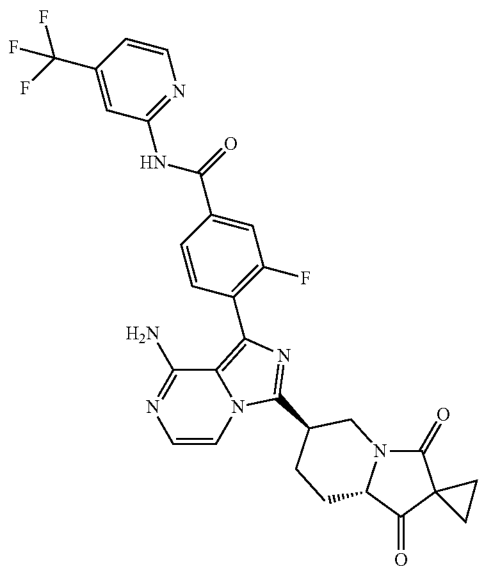 [SMILES: Nc1nccn2c([C@@H]3CC[C@H]4C(=O)C5(CC5)C(=O)N4C3)nc(-c3ccc(C(=O)Nc4cc(C(F)(F)F)ccn4)cc3F)c12] | 4-{8-amino-3-[(6'R,8a'S)-1',3'-dioxohexahydrospiro[cyclopropane-1,2'-indolizin]-6'-yl]imidazo[1,5-a]pyrazin-1-yl}-3-fluoro-N-[4-(trifluoromethyl)pyridin-2-yl]benzamide | Calc'd 594.0, found 594.28 |
| 8 | 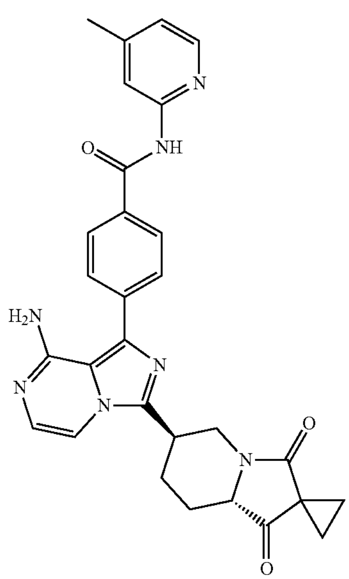 [SMILES: Cc1ccnc(NC(=O)c2ccc(-c3nc([C@@H]4CC[C@H]5C(=O)C6(CC6)C(=O)N5C4)n4ccnc(N)c34)cc2)c1] | 4-{8-amino-3-[(6'R,8a'S)-1',3'-dioxohexahydrospiro[cyclopropane-1,2'-indolizin]-6'-yl]imidazo[1,5-a]pyrazin-1-yl}-N-(4-methylpyridin-2-yl)benzamide | Calc'd 522.0, found 522.28 |

TABLE 1-continued

| Comp # | Structure | IUPAC Name | Exact Mass [M + H]+ |
|---|---|---|---|
| 9 | 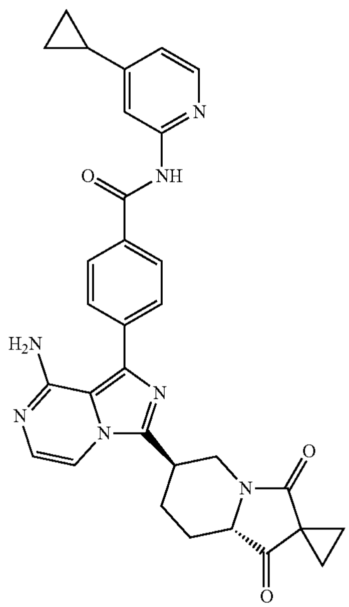 [SMILES: Nc1nccn2c([C@@H]3CC[C@H]4C(=O)C5(CC5)C(=O)N4C3)nc(-c3ccc(C(=O)Nc4cc(C5CC5)ccn4)cc3)c12] | 4-{8-amino-3-[(6'R,8a'S)-1',3'-dioxohexahydrospiro[cyclopropane-1,2'-indolizin]-6'-yl]imidazo[1,5-a]pyrazin-1-yl}-N-(4-cyclopropylpyridin-2-yl)benzamide | Calc'd 548.0, found 548.35 |
| 10 | 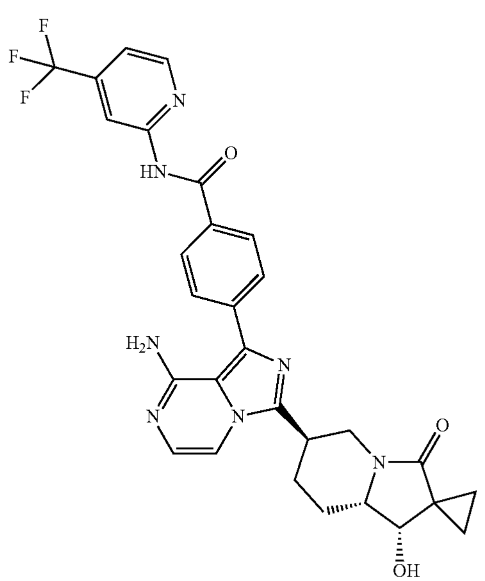 [SMILES: Nc1nccn2c([C@@H]3CC[C@H]4[C@@H](O)C5(CC5)C(=O)N4C3)nc(-c3ccc(C(=O)Nc4cc(C(F)(F)F)ccn4)cc3)c12] | 4-{8-amino-3-[(1'S,6'R,8a'S)-1'-hydroxy-3'-oxohexahydrospiro[cyclopropane-1,2'-indolizin]-6'-yl]imidazo[1,5-a]pyrazin-1-yl}-N-[4-(trifluoromethyl)pyridin-2-yl]benzamide | Calc'd 578.0, found 578.16 |

TABLE 1-continued

| Comp # | Structure | IUPAC Name | Exact Mass [M + H]+ |
|---|---|---|---|
| 11 | 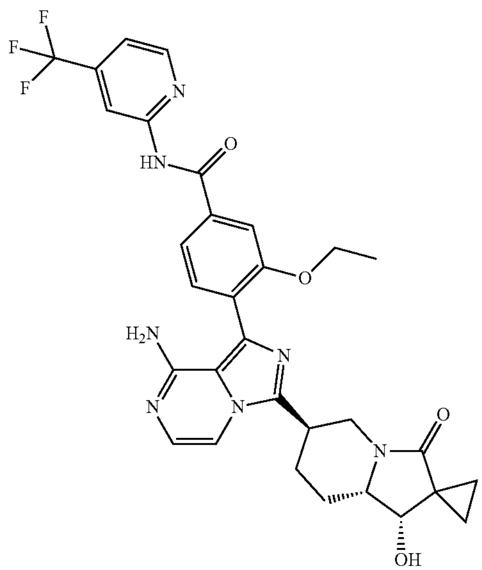 [SMILES: CCOc1cc(C(=O)Nc2cc(C(F)(F)F)ccn2)ccc1-c1nc([C@@H]2CC[C@H]3[C@@H](O)C4(CC4)C(=O)N3C2)n2ccnc(N)c12] | 4-{8-amino-3-[(1'S,6'R,8a'S)-1'-hydroxy-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide | Calc'd 622.0, found 622.18 |
| 12 | 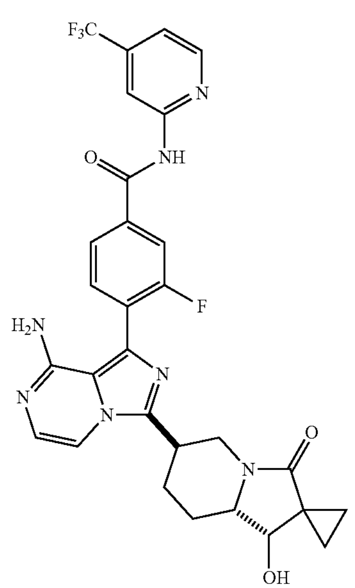 | 4-(8-amino-3-((1'S,6'R,8a'S)-1'-hydroxy-3'-oxohexahydro-1'H-spiro[cyclopropane-1,2'-indolizin]-6'-yl)imidazo[1,5-a]pyrazin-1-yl)-3-fluoro-N-(4-(trifluoromethyl)pyridin-2-yl)benzamide | 596.15 |

TABLE 1-continued

| Comp # | Structure | IUPAC Name | Exact Mass [M + H]+ |
|---|---|---|---|
| 13 | 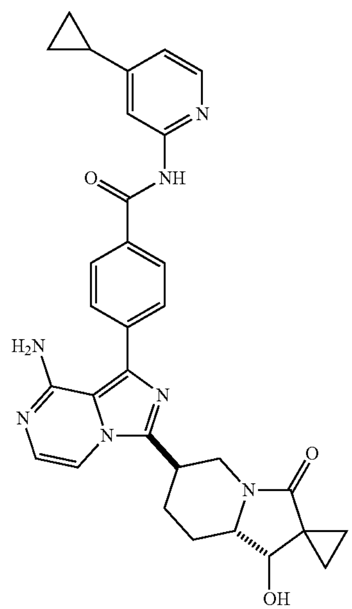 | 4-(8-amino-3-((1'S,6'R,8a'S)-1'-hydroxy-3'-oxohexahydro-1'H-spiro[cyclopropane-1,2'-indolizin]-6'-yl)imidazo[1,5-a]pyrazin-1-yl)-N-(4-cyclopropanepyridin-2-yl)benzamide | 550.18 |
| 14 | 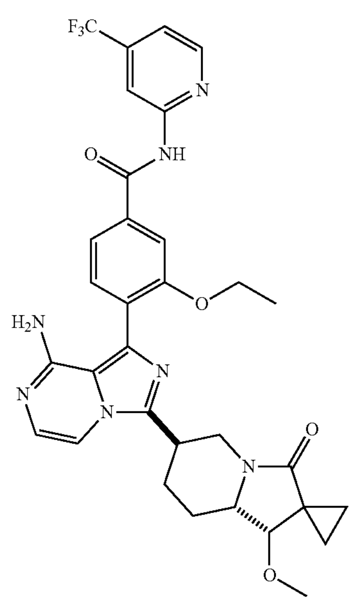 | 4-(8-amino-3-((1'S,6'R,8a'S)-1'-methoxy-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide | 636.20 |

TABLE 1-continued

| Comp # | Structure | IUPAC Name | Exact Mass [M + H]+ |
|---|---|---|---|
| 15 | 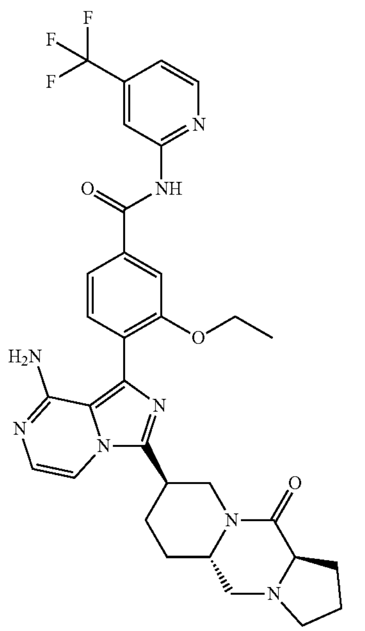 [SMILES: CCOc1cc(C(=O)Nc2cc(C(F)(F)F)ccn2)ccc1-c1nc([C@@H]2CC[C@H]3CN4CCC[C@@H]4C(=O)N3C2)n2ccnc(N)c12] | 4-{8-amino-3-[(5aS,8R,11aR)-11-oxodecahydro-1H-pyrido[1,2-a]pyrrolo[1,2-d]pyrazin-8-yl]imidazo[1,5-a]pyrazin-1-yl}-3-ethoxy-N-[4-(trifluoromethyl)pyridin-2-yl]benzamide | Calc'd 635.0, found 635.3 |
| 16 | 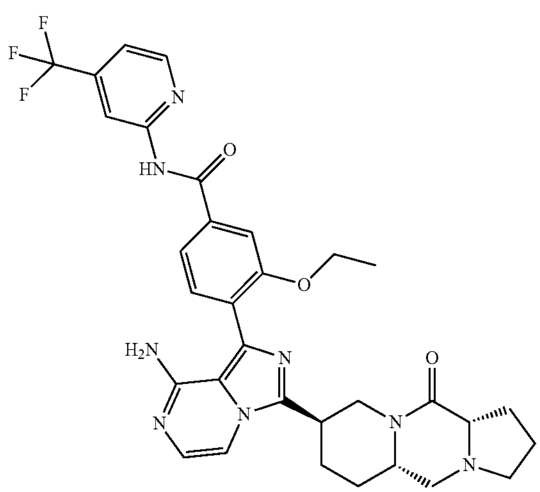 [SMILES: CCOc1cc(C(=O)Nc2cc(C(F)(F)F)ccn2)ccc1-c1nc([C@@H]2CC[C@H]3CN4CCC[C@H]4C(=O)N3C2)n2ccnc(N)c12] | 4-{8-amino-3-[(5aS,8R,11aS)-11-oxodecahydro-1H-pyrido[1,2-a]pyrrolo[1,2-d]pyrazin-8-yl]imidazo[1,5-a]pyrazin-1-yl}-3-ethoxy-N-[4-(trifluoromethyl)pyridin-2-yl]benzamide | Calc'd 635.0, found 635.1 |

TABLE 1-continued

| Comp # | Structure | IUPAC Name | Exact Mass [M + H]+ |
|---|---|---|---|
| 17 | 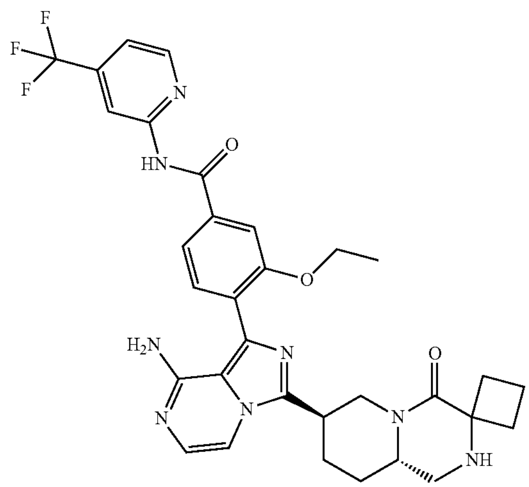 [SMILES: CCOc1cc(C(=O)Nc2cc(C(F)(F)F)ccn2)ccc1-c1nc([C@@H]2CC[C@H]3CNC4(CCC4)C(=O)N3C2)n2ccnc(N)c12] | 4-{8-amino-3-[(7'R,9a'S)-4'-oxohexahydro-2'H-spiro[cyclobutane-1,3'-pyrido[1,2-a]pyrazin]-7'-yl]imidazo[1,5-a]pyrazin-1-yl}-3-ethoxy-N-[4-(trifluoromethyl)pyridin-2-yl]benzamide | Calc'd 635.0, found 635.4 |
| 18 | 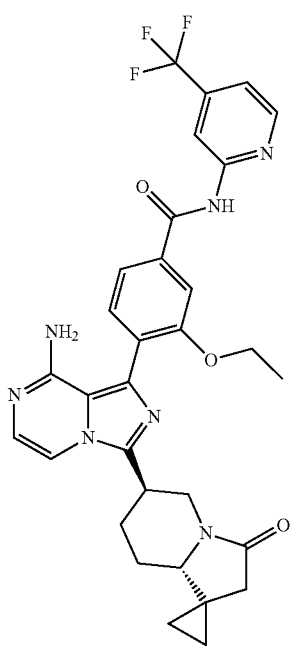 [SMILES: CCOc1cc(C(=O)Nc2cc(C(F)(F)F)ccn2)ccc1-c1nc([C@@H]2CC[C@@H]3N(C2)C(=O)CC32CC2)n2ccnc(N)c12] | 4-{8-amino-3-[(6'R,8a'S)-3'-oxohexahydro-5'H-spiro[cyclopropane-1,1'-indolizin]-6'-yl]imidazo[1,5-a]pyrazin-1-yl}-3-ethoxy-N-[4-(trifluoromethyl)pyridin-2-yl]benzamide | Calc'd 606.0, found 606.2 |

TABLE 1-continued

| Comp # | Structure | IUPAC Name | Exact Mass [M + H]+ |
|---|---|---|---|
| 19 | 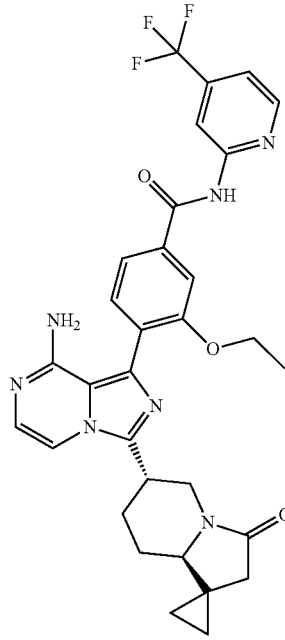 | 4-{8-amino-3-[(6'S,8a'R)-3'-oxohexahydro-5'H-spiro[cyclopropane-1,1'-indolizin]-6'-yl]imidazo[1,5-a]pyrazin-1-yl}-3-ethoxy-N-[4-(trifluoromethyl)pyridin-2-yl]benzamide | Calc'd 606.0, found 606.2 |
| 20 | 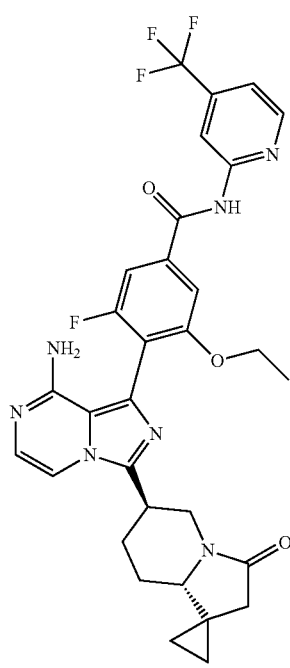 [SMILES: CCOc1cc(C(=O)Nc2cc(C(F)(F)F)ccn2)cc(F)c1-c1nc([C@@H]2CC[C@@H]3N(C2)C(=O)CC32CC2)n2ccnc(N)c12] | 4-{8-amino-3-[(6'R,8a'S)-3'-oxohexahydro-5'H-spiro[cyclopropane-1,1'-indolizin]-6'-yl]imidazo[1,5-a]pyrazin-1-yl}-3-ethoxy-5-fluoro-N-[4-(trifluoromethyl)pyridin-2-yl]benzamide | Calc'd 624.0, found 624.2 |

TABLE 1-continued

| Comp # | Structure | IUPAC Name | Exact Mass [M + H]+ |
|---|---|---|---|
| 21 | 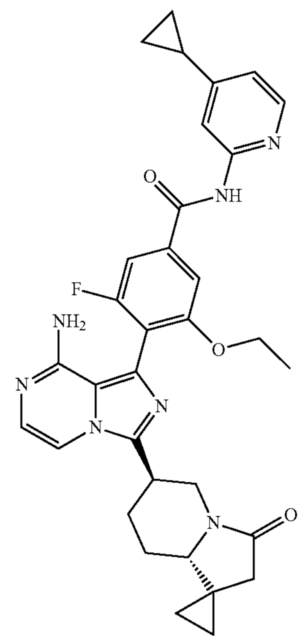 [SMILES: CCOc1cc(C(=O)Nc2cc(C3CC3)ccn2)cc(F)c1-c1nc([C@@H]2CC[C@@H]3N(C2)C(=O)CC32CC2)n2ccnc(N)c12] | 4-{8-amino-3-[(6'R,8a'S)-3'-oxohexahydro-5'H-spiro[cyclopropane-1,1'-indolizin]-6'-yl]imidazo[1,5-a]pyrazin-1-yl}-N-(4-cyclopropylpyridin-2-yl)-3-ethoxy-5-fluorobenzamide | Calc'd 596.0, found 596.2 |
| 22 | 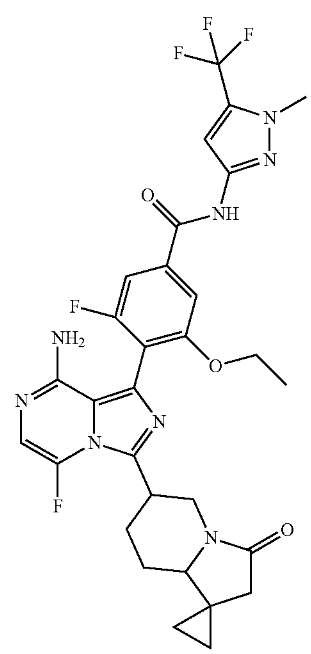 [SMILES: CCOc1cc(C(=O)Nc2cc(C(F)(F)F)n(C)n2)cc(F)c1-c1nc(C2CCC3N(C2)C(=O)CC32CC2)n2c(F)cnc(N)c12] | 4-[8-amino-5-fluoro-3-(3'-oxohexahydro-5'H-spiro[cyclopropane-1,1'-indolizin]-6'-yl)imidazo[1,5-a]pyrazin-1-yl]-3-ethoxy-5-fluoro-N-[1-methyl-5-(trifluoromethyl)-1H-pyrazol-3-yl]benzamide | Calc'd 645.0, found 645.1 |

TABLE 1-continued

| Comp # | Structure | IUPAC Name | Exact Mass [M + H]+ |
|---|---|---|---|
| 23 | 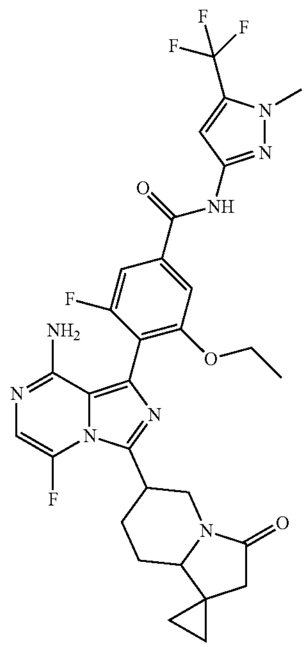 [SMILES: CCOc1cc(C(=O)Nc2cc(C(F)(F)F)n(C)n2)cc(F)c1-c1nc(C2CCC3N(C2)C(=O)CC32CC2)n2c(F)cnc(N)c12] | 4-[8-amino-5-fluoro-3-(3'-oxohexahydro-5'H-spiro[cyclopropane-1,1'-indolizin]-6'-yl)imidazo[1,5-a]pyrazin-1-yl]-3-ethoxy-5-fluoro-N-[1-methyl-5-(trifluoromethyl)-1H-pyrazol-3-yl]benzamide | Calc'd 645.0, found 645.2 |
| 24 | 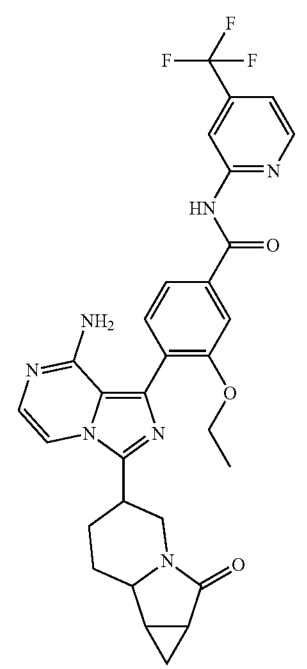 [SMILES: CCOc1cc(C(=O)Nc2cc(C(F)(F)F)ccn2)ccc1-c1nc(C2CCC3C4CC4C(=O)N3C2)n2ccnc(N)c12] | 4-[8-amino-3-(2-oxooctahydro-1H-cyclopropa[a]indolizin-5-yl)imidazo[1,5-a]pyrazin-1-yl]-3-ethoxy-N-[4-(trifluoromethyl)pyridin-2-yl]benzamide | Calc'd 592.0, found 592.1 |

TABLE 1-continued

| Comp # | Structure | IUPAC Name | Exact Mass [M + H]+ |
|---|---|---|---|
| 25 | 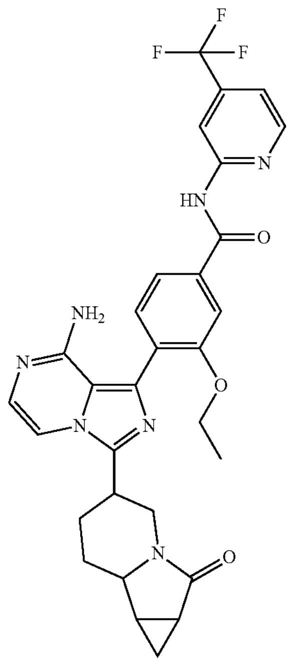 [SMILES: CCOc1cc(C(=O)Nc2cc(C(F)(F)F)ccn2)ccc1-c1nc(C2CCC3C4CC4C(=O)N3C2)n2ccnc(N)c12] | 4-[8-amino-3-(2-oxooctahydro-1H-cyclopropa[a]indolizin-5-yl)imidazo[1,5-a]pyrazin-1-yl]-3-ethoxy-N-[4-(trifluoromethyl)pyridin-2-yl]benzamide | Calc'd 592.0, found 592.2 |
| 26 | 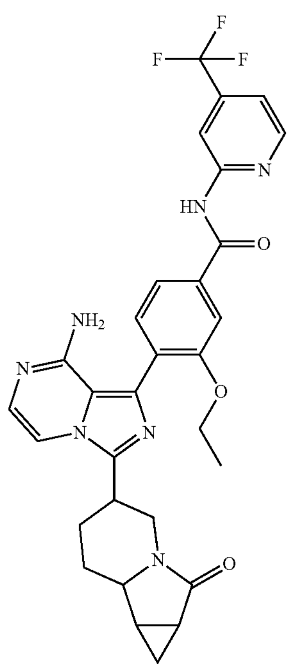 [SMILES: CCOc1cc(C(=O)Nc2cc(C(F)(F)F)ccn2)ccc1-c1nc(C2CCC3C4CC4C(=O)N3C2)n2ccnc(N)c12] | 4-[8-amino-3-(2-oxooctahydro-1H-cyclopropa[a]indolizin-5-yl)imidazo[1,5-a]pyrazin-1-yl]-3-ethoxy-N-[4-(trifluoromethyl)pyridin-2-yl]benzamide | Calc'd 592.0, found 592.1 |

TABLE 1-continued

| Comp # | Structure | IUPAC Name | Exact Mass [M + H]+ |
|---|---|---|---|
| 27 | 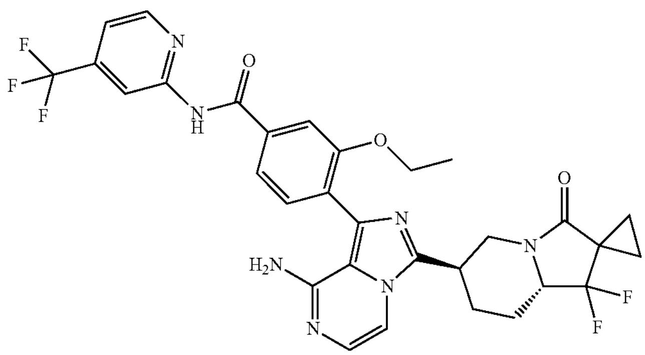 [SMILES: CCOc1cc(C(=O)Nc2cc(C(F)(F)F)ccn2)ccc1-c1nc([C@@H]2CC[C@@H]3N(C2)C(=O)C2(CC2)C3(F)F)n2ccnc(N)c12] | 4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide | Calc'd 642.0, found 642.28 |
| 28 | 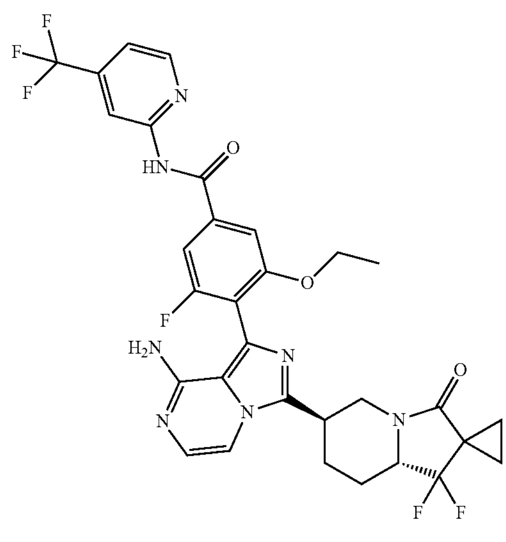 [SMILES: CCOc1cc(C(=O)Nc2cc(C(F)(F)F)ccn2)cc(F)c1-c1nc([C@@H]2CC[C@@H]3N(C2)C(=O)C2(CC2)C3(F)F)n2ccnc(N)c12] | 4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-ethoxy-5-fluoro-N-[4-(trifluoromethyl)pyridin-2-yl]benzamide | Calc'd 660.0, found 660.23 |
| 29 | 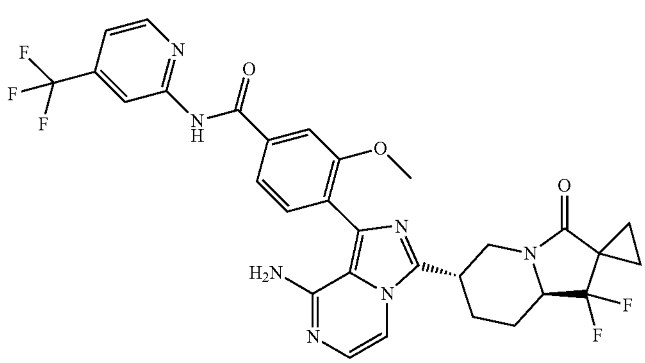 [SMILES: COc1cc(C(=O)Nc2cc(C(F)(F)F)ccn2)ccc1-c1nc([C@H]2CC[C@H]3N(C2)C(=O)C2(CC2)C3(F)F)n2ccnc(N)c12] | 4-{8-amino-3-[(6'S,8a'R)-1',1'-difluoro-3'-oxohexahydrospiro[cyclopropane-1,2'-indolizin]-6'-yl]imidazo[1,5-a]pyrazin-1-yl}-3-methoxy-N-[4-(trifluoromethyl)pyridin-2-yl]benzamide | Calc'd 628.0, found 628.13 |

TABLE 1-continued

| Comp # | Structure | IUPAC Name | Exact Mass [M + H]+ |
|---|---|---|---|
| 30 | 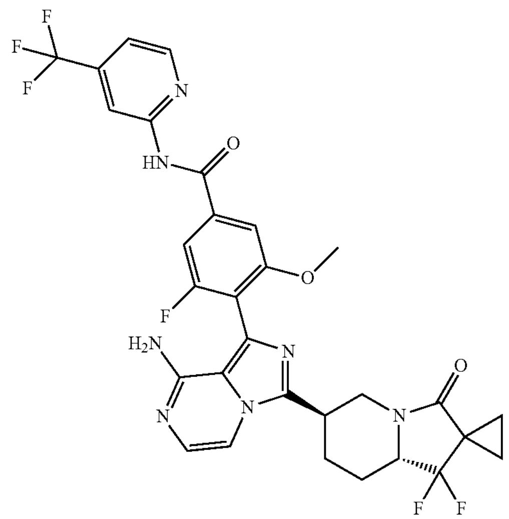 [SMILES: COc1cc(C(=O)Nc2cc(C(F)(F)F)ccn2)cc(F)c1-c1nc([C@@H]2CC[C@@H]3N(C2)C(=O)C2(CC2)C3(F)F)n2ccnc(N)c12] | 4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-fluoro-5-methoxy-N-[4-(trifluoromethyl)pyridin-2-yl]benzamide | Calc'd 646.0, found 646.27 |
| 31 | 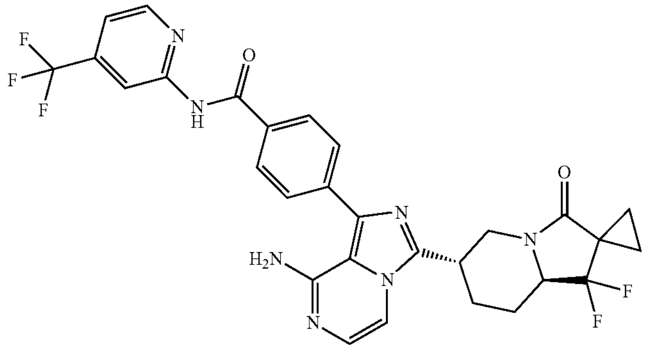 [SMILES: Nc1nccn2c([C@H]3CC[C@H]4N(C3)C(=O)C3(CC3)C4(F)F)nc(-c3ccc(C(=O)Nc4cc(C(F)(F)F)ccn4)cc3)c12] | 4-{8-amino-3-[(6'S,8a'R)-1',1'-difluoro-3'-oxohexahydrospiro[cyclopropane-1,2'-indolizin]-6'-yl]imidazo[1,5-a]pyrazin-1-yl}-N-[4-(trifluoromethyl)pyridin-2-yl]benzamide | Calc'd 598.0, found 598.21 |
| 32 | 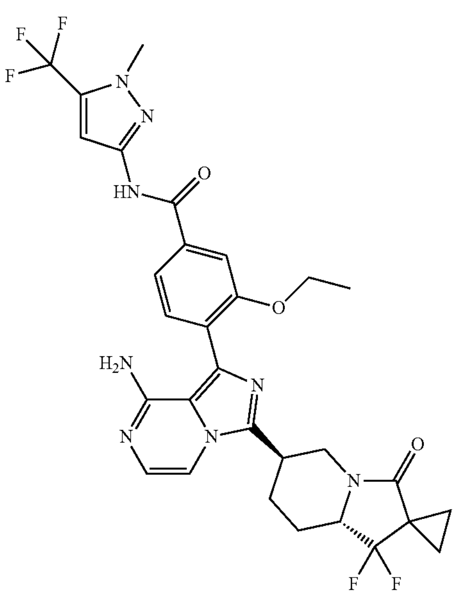 [SMILES: CCOc1cc(C(=O)Nc2cc(C(F)(F)F)n(C)n2)ccc1-c1nc([C@@H]2CC[C@@H]3N(C2)C(=O)C2(CC2)C3(F)F)n2ccnc(N)c12] | 4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-ethoxy-N-[1-methyl-5-(trifluoromethyl)-1H-pyrazol-3-yl]benzamide | Calc'd 645.0, found 645.30 |

TABLE 1-continued

| Comp # | Structure | IUPAC Name | Exact Mass [M + H]+ |
|---|---|---|---|
| 33 | 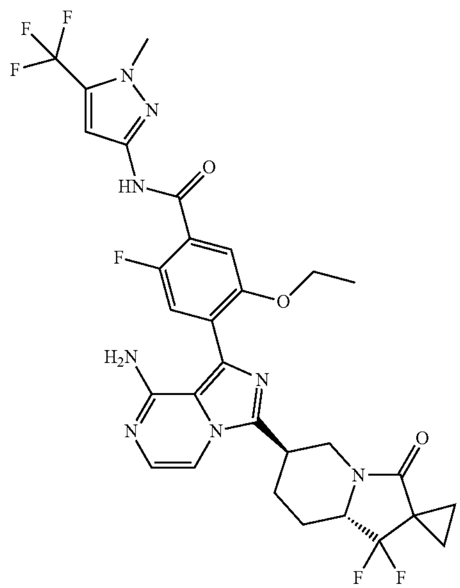 [SMILES: CCOc1cc(C(=O)Nc2cc(C(F)(F)F)n(C)n2)c(F)cc1-c1nc([C@@H]2CC[C@@H]3N(C2)C(=O)C2(CC2)C3(F)F)n2ccnc(N)c12] | 4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-5-ethoxy-2-fluoro-N-[1-methyl-5-(trifluoromethyl)-1H-pyrazol-3-yl]benzamide | Calc'd 663.0, found 663.34 |
| 34 | 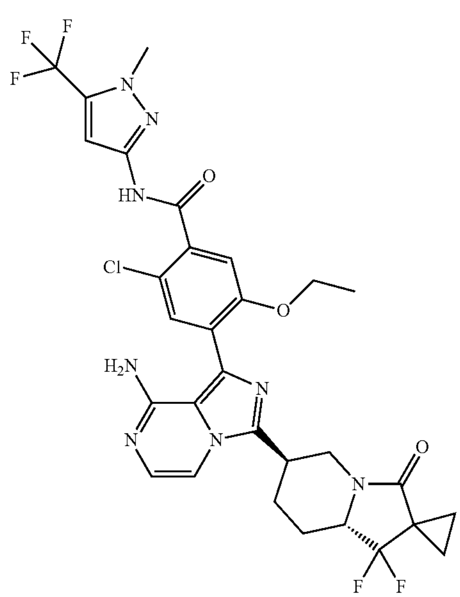 [SMILES: CCOc1cc(C(=O)Nc2cc(C(F)(F)F)n(C)n2)c(Cl)cc1-c1nc([C@@H]2CC[C@@H]3N(C2)C(=O)C2(CC2)C3(F)F)n2ccnc(N)c12] | 4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-2-chloro-5-ethoxy-N-[1-methyl-5-(trifluoromethyl)-1H-pyrazol-3-yl]benzamide | Calc'd 679.0, found 679.20 |

| Comp # | Structure | IUPAC Name | Exact Mass [M + H]+ |
|---|---|---|---|
| 35 | 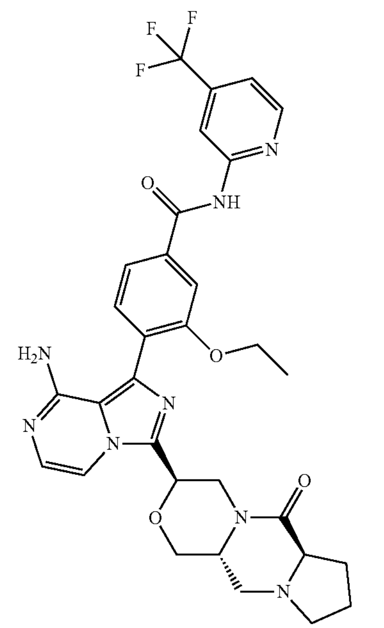 [SMILES: CCOc1cc(C(=O)Nc2cc(C(F)(F)F)ccn2)ccc1-c1nc([C@H]2CN3C(=O)[C@H]4CCCN4C[C@@H]3CO2)n2ccnc(N)c12] | 4-{8-amino-3-[(3R,6aR,11aR)-6-oxooctahydro-1H,6H-pyrrolo[1',2':4,5]pyrazino[2,1-c][1,4]oxazin-3-yl]imidazo[1,5-a]pyrazin-1-yl}-3-ethoxy-N-[4-(trifluoromethyl)pyridin-2-yl]benzamide | Calc'd 637.2, found 637.2 |
| 36 | 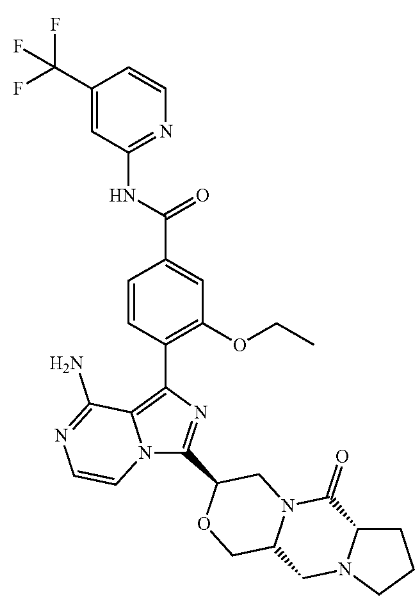 | 4-{8-amino-3-[(3R,6aS,11aR)-6-oxooctahydro-1H,6H-pyrrolo[1',2':4,5]pyrazino[2,1-c][1,4]oxazin-3-yl]imidazo[1,5-a]pyrazin-1-yl}-3-ethoxy-N-[4-(trifluoromethyl)pyridin-2-yl]benzamide | Calc'd 637.2, found 637.2 |

TABLE 1-continued
| Comp # | Structure | IUPAC Name | Exact Mass [M + H]+ |
|---|---|---|---|
| 37 | 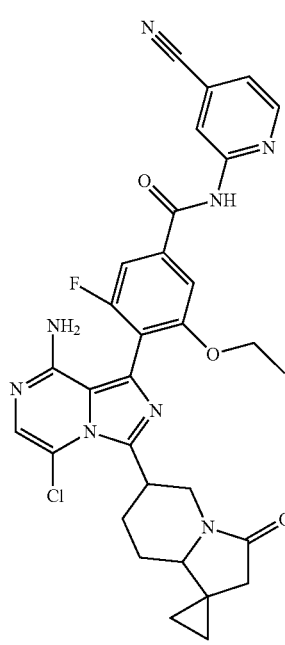 | 4-[8-amino-5-chloro-3-(3'-oxohexahydro-5'H-spiro[cyclopropane-1,1'-indolizin]-6'-yl)imidazo[1,5-a]pyrazin-1-yl]-N-(4-cyanopyridin-2-yl)-3-ethoxy-5-fluorobenzamide | Calc'd 615.2, found 615.1 |
| 38 | 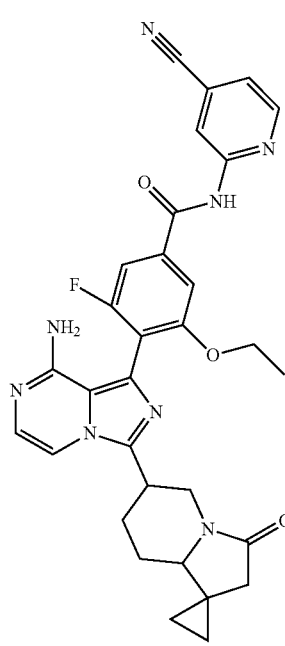 | 4-[8-amino-3-(3'-oxohexahydro-5'H-spiro[cyclopropane-1,1'-indolizin]-6'-yl)imidazo[1,5-a]pyrazin-1-yl]-N-(4-cyanopyridin-2-yl)-3-ethoxy-5-fluorobenzamide | Calc'd 581.2, found 581.2 |

TABLE 1-continued

| Comp # | Structure | IUPAC Name | Exact Mass [M + H]+ |
|---|---|---|---|
| 39 | 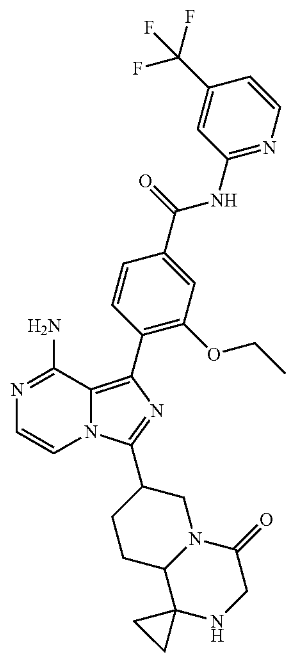 [SMILES: CCOc1cc(C(=O)Nc2cc(C(F)(F)F)ccn2)ccc1-c1nc(C2CCC3N(C2)C(=O)CNC32CC2)n2ccnc(N)c12] | 4-[8-amino-3-(4'-oxohexahydro-2'H,6'H-spiro[cyclopropane-1,1'-pyrido[1,2-a]pyrazin]-7'-yl)imidazol[1,5-a]pyrazin-1-yl]-3-ethoxy-N-[4-(trifluoromethyl)pyridin-2-yl]benzamide | Calc'd 621.3, found 621.2 |
| 40 | 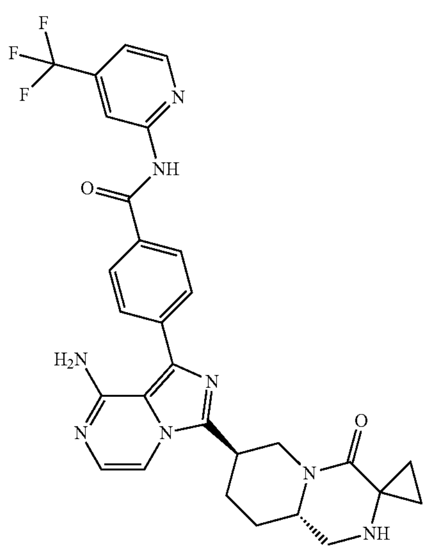 [SMILES: Nc1nccn2c([C@@H]3CC[C@H]4CNC5(CC5)C(=O)N4C3)nc(-c3ccc(C(=O)Nc4cc(C(F)(F)F)ccn4)cc3)c12] | 4-{8-amino-3-[(7'R,9a'S)-4'-oxohexahydro-2'H-spiro[cyclopropane-1,3'-pyrido[1,2-a]pyrazin]-7'-yl]imidazo[1,5-a]pyrazin-1-yl}-N-[4-(trifluoromethyl)pyridin-2-yl]benzamide | Calc'd 577.0, found 577.1 |

| Comp # | Structure | IUPAC Name | Exact Mass [M + H]+ |
|---|---|---|---|
| 41 | 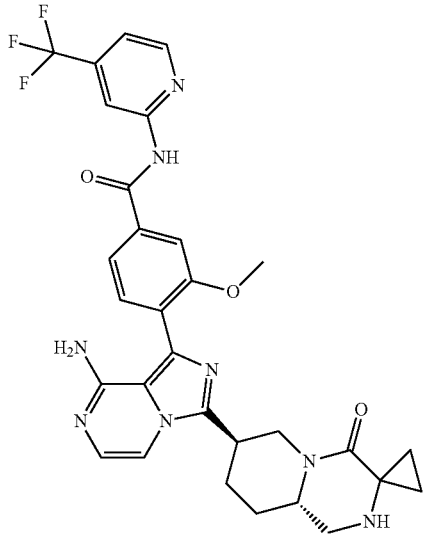 [SMILES: COc1cc(C(=O)Nc2cc(C(F)(F)F)ccn2)ccc1-c1nc([C@@H]2CC[C@H]3CNC4(CC4)C(=O)N3C2)n2ccnc(N)c12] | 4-{8-amino-3-[(7'R,9a'S)-4'-oxohexahydro-2'H-spiro[cyclopropane-1,3'-pyrido[1,2-a]pyrazin]-7'-yl]imidazo[1,5-a]pyrazin-1-yl}-3-methoxy-N-[4-(trifluoromethyl)pyridin-2-yl]benzamide | Calc'd 607.0, found 607.2 |
| 42 | 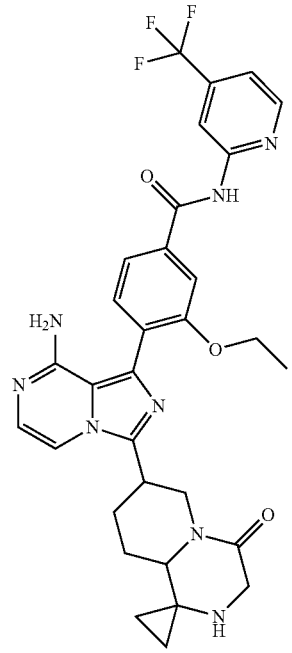 [SMILES: CCOc1cc(C(=O)Nc2cc(C(F)(F)F)ccn2)ccc1-c1nc(C2CCC3N(C2)C(=O)CNC32CC2)n2ccnc(N)c12] | 4-[8-amino-3-(4'-oxohexahydro-2'H,6'H-spiro[cyclopropane-1,1'-pyrido[1,2-a]pyrazin]-7'-yl)imidazo[1,5-a]pyrazin-1-yl]-3-ethoxy-N-[4-(trifluoromethyl)pyridin-2-yl]benzamide | Calc'd 621.0, found 621.2 |

TABLE 1-continued

| Comp # | Structure | IUPAC Name | Exact Mass [M + H]+ |
|---|---|---|---|
| 43 | 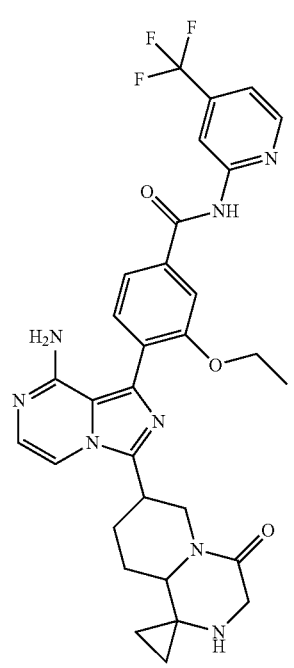 [SMILES: CCOc1cc(C(=O)Nc2cc(C(F)(F)F)ccn2)ccc1-c1nc(C2CCC3N(C2)C(=O)CNC32CC2)n2ccnc(N)c12] | 4-[8-amino-3-(4'-oxohexahydro-2'H,6'H-spiro[cyclopropane-1,1'-pyrido[1,2-a]pyrazin]-7'-yl)imidazo[1,5-a]pyrazin-1-yl]-3-ethoxy-N-[4-(trifluoromethyl)pyridin-2-yl]benzamide | Calc'd 621.0, found 621.3 |
| 44 | 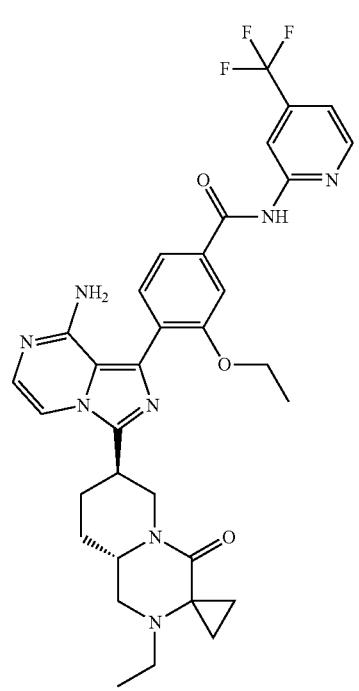 [SMILES: CCOc1cc(C(=O)Nc2cc(C(F)(F)F)ccn2)ccc1-c1nc([C@@H]2CC[C@H]3CN(CC)C4(CC4)C(=O)N3C2)n2ccnc(N)c12] | 4-{8-amino-3-[(7'R,9a'S)-2'-ethyl-4'-oxohexahydro-2'H-spiro[cyclopropane-1,3'-pyrido[1,2-a]pyrazin]-7'-yl]imidazo[1,5-a]pyrazin-1-yl}-3-ethoxy-N-[4-(trifluoromethyl)pyridin-2-yl]benzamide | Calc'd 649.0, found 649.2 |

TABLE 1-continued

| Comp # | Structure | IUPAC Name | Exact Mass [M + H]+ |
|---|---|---|---|
| 45 | 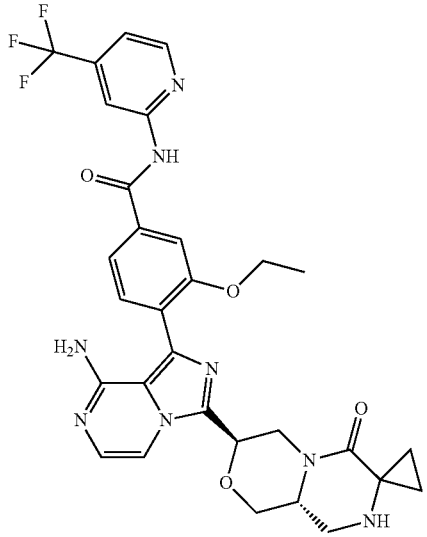 [SMILES: CCOc1cc(C(=O)Nc2cc(C(F)(F)F)ccn2)ccc1-c1nc([C@H]2CN3C(=O)C4(CC4)NC[C@@H]3CO2)n2ccnc(N)c12] | 4-{8-amino-3-[(3'R,9a'R)-6'-oxohexahydrospiro[cyclopropane-1,7'-pyrazino[2,1-c][1,4]oxazin]-3'-yl]imidazo[1,5-a]pyrazin-1-yl}-3-ethoxy-N-[4-(trifluoromethyl)pyridin-2-yl]benzamide | Calc'd 623.0, found 623.2 |
| 46 | 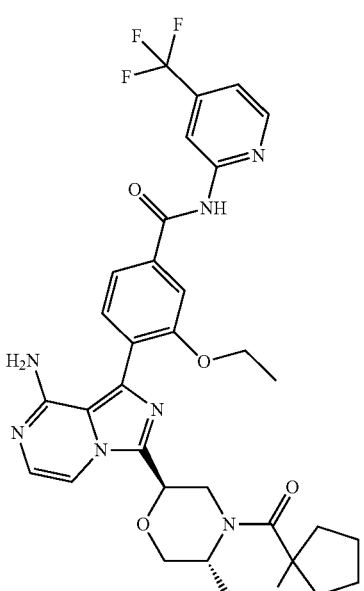 | 4-{8-amino-3-[(3'R,9a'R)-6'-oxohexahydrospiro[cyclopentane-1,7'-pyrazino[2,1-c][1,4]oxazin]-3'-yl]imidazo[1,5-a]pyrazin-1-yl}-3-ethoxy-N-[4-(trifluoromethyl)pyridin-2-yl]benzamide | Calc'd 651.0, found 651.2 |

TABLE 1-continued

| Comp # | Structure | IUPAC Name | Exact Mass [M + H]+ |
|---|---|---|---|
| 47 | 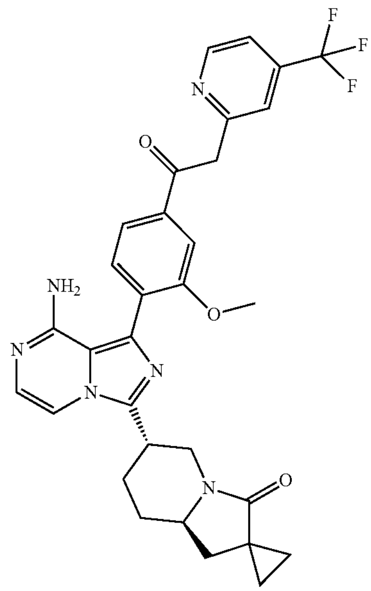 [SMILES: COc1cc(C(=O)Cc2cc(C(F)(F)F)ccn2)ccc1-c1nc([C@H]2CC[C@@H]3CC4(CC4)C(=O)N3C2)n2ccnc(N)c12] | 4-{8-amino-3-[(6'S,8a'R)-3'-oxohexahydrospiro[cyclopropane-1,2'-indolizin]-6'-yl]imidazo[1,5-a]pyrazin-1-yl}-3-methoxy-N-[4-(trifluoromethyl)pyridin-2-yl]benzamide | Calc'd 592.0, found 592.30 |
| 48 | 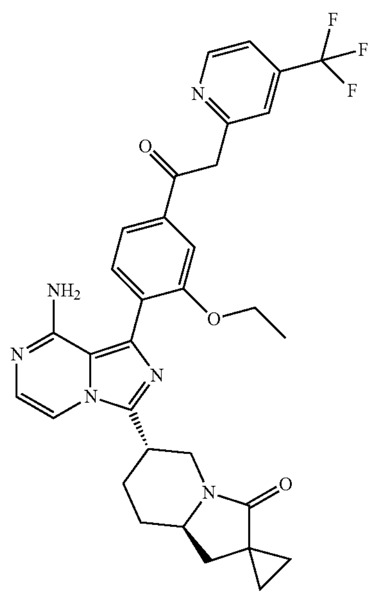 [SMILES: CCOc1cc(C(=O)Cc2cc(C(F)(F)F)ccn2)ccc1-c1nc([C@H]2CC[C@@H]3CC4(CC4)C(=O)N3C2)n2ccnc(N)c12] | 4-{8-amino-3-[(6'S,8a'R)-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide | Calc'd 606.0, found 606.30 |

Biological Activity

The Btk inhibitor compounds of the invention having Formula I inhibit the Btk kinase activity. All compounds of the invention have an IC50 of 10 µM or lower. In another aspect the invention relates to compounds of Formula I which have an IC50 of less than 100 nM. In yet another aspect the invention relates to compounds of Formula I which have an IC50 of less than 10 nM.

The term IC50 means the concentration of the test compound that is required for 50% inhibition of its maximum effect in vitro.

Btk Enzyme Activity Assay Methods

BTK enzymatic activity was determined with the LANCE (Lanthanide Chelate Excite) TR-FRET (Time-resolved fluorescence resonance energy transfer) assay. In this assay, the potency ($IC_{50}$) of each compound was determined from an eleven point (1:3 serial dilution; final compound concentration range in assay from 1 µM to 0.017 nM) titration curve using the following outlined procedure. To each well of a black non-binding surface Corning 384-well microplate (Corning Catalog #3820), 5 nL of compound (2000 fold dilution in final assay volume of 10 µL) was dispensed, followed by the addition of 7.5 µL of 1× kinase buffer (50 mM Hepes 7.5, 10 mM $MgCl_2$, 0.01% Brij-35, 1 mM EGTA, 0.05% BSA & 1 mM DTT) containing 5.09 pg/µL (66.67 pM) of BTK enzyme (recombinant protein from baculovirus-transfected Sf9 cells: full-length BTK, 6HIS-tag cleaved). Following a 60 minute compound and enzyme incubation, each reaction was initiated by the addition of 2.5 μL 1× kinase buffer containing 8 μM biotinylated "A5" peptide (Biotin-EQEDEPEGDYFEWLE-NH2) (SEQ-.ID.NO.: 1), and 100 μM ATP. The final reaction in each well of 10 μL consists of 50 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate: anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The following Table 2 provides specific IC50 values for all the examples. The IC50 values set forth below were determined according to Assay method described above.

TABLE 2

| BTK binding potency | |
| --- | --- |
| Compound number | BTK binding IC50 (nM) |
| 1 | 0.1722 |
| 2 | 11.78 |
| 3 | 1.001 |
| 4 | |
| 5 | 1.472 |
| 6 | 0.8569 |
| 7 | 0.4252 |
| 8 | 2.066 |
| 9 | 1.621 |
| 10 | 0.9515 |
| 11 | 0.7013 |
| 12 | 0.3845 |
| 13 | 1.223 |
| 14 | 1.281 |
| 15 | 0.4622 |
| 16 | 0.489 |
| 17 | 0.5006 |
| 18 | 0.1271 |
| 19 | 3.809 |
| 20 | 0.1708 |
| 21 | 0.1603 |
| 22 | 0.2687 |
| 23 | 5.903 |
| 24 | 11.05 |
| 25 | 17.86 |
| 26 | 0.2016 |
| 27 | 1.598 |
| 28 | 1.539 |
| 29 | 1.512 |
| 30 | 1.611 |
| 31 | 0.4102 |
| 32 | 6.225 |
| 33 | 9.041 |
| 34 | 6.952 |
| 35 | 1.255 |

TABLE 2-continued

| BTK binding potency | |
| --- | --- |
| Compound number | BTK binding IC50 (nM) |
| 36 | 1.004 |
| 37 | 0.1856 |
| 38 | 0.2221 |
| 39 | 0.3217 |
| 40 | 0.1728 |
| 41 | 0.2519 |
| 42 | 0.2311 |
| 43 | 5.609 |
| 44 | 0.2494 |
| 45 | 0.2408 |
| 46 | |
| 47 | 0.5283 |
| 48 | 1.188 |

Compounds were also screened in an adenosine uptake functional cellular assay using the protocol described below.

[$^3$H]Adenosine Uptake Assay Methods

Adenosine uptake activity was determined by monitoring the accumulation of tritiated adenosine into HeLa cells (ATCC catalog # CCL-2) using a PMT-based radiometric detection instrument. In this assay, the potency ($IC_{50}$) of each compound was determined from a ten point (1:3 serial dilution; final compound concentration range in assay from 10 μM to 0.032 nM) titration curve using the following outlined procedure. To each well of a 96-well CytoStar-T scintillating microplate (Perkin Elmer Catalog # RPNQ0163), 25 000 HeLa cells in 100 μL of growth medium comprising: Minimum Essential Media (Life Technologies Catalog # 11095-080)+10% (v/v) foetal bovine serum (FBS; Sigma Aldrich Catalog # F2442) was added. These cells were incubated overnight at 37° C. in a humidified atmosphere with 5% (v/v) $CO_2$. After this time the growth medium was removed and replaced with 40 μL assay medium comprising: Hanks balanced salts solution (HBSS; Thermo Fisher Catalog # SH30268.01)+5% (v/v) FBS. Compound stock solutions in DMSO were diluted in assay medium to 2.5× final compound concentration maintaining a constant DMSO concentration of 0.25% (v/v). 40 μL of compound in assay medium was dispensed into individual wells of the Cytostar-T plates and the plates were incubated for 30 minutes under ambient laboratory conditions. Following this incubation, 20 μL of 500 nM [$^3$H]adenosine (American Radiolabeled Chemicals Inc. Catalog # ART0287) in assay medium was added and incubated for a further 60 minutes under ambient laboratory conditions. The amount of radiolabel accumulation was then determined using a Perkin Elmer Topcount NXT microplate reader. In brief, HeLa cells adhere to the bottom of the Cytostar-T plate, uptake of [$^3$H]adenosine into these cells brings the radiolabel into sufficient proximity to excite the scintillant in the base of the plates. These events are captured by single PMT, time-resolved coincidence counting. IC$_{50}$ values were determined by 4 parameter robust fit of counts per second values vs. (Log$_{10}$) compound concentrations.

TABLE 3

Adenosine uptake inhibition potency

| Compound Number | ADU inhibition IC50 (nM) |
|---|---|
| 1 | 1055 |
| 2 | 895.2 |
| 3 | 1327 |
| 4 | |
| 5 | 912 |
| 6 | 152.1 |
| 7 | 172.7 |
| 8 | 50.89 |
| 9 | 182.7 |
| 10 | 860.6 |
| 11 | 1993 |
| 12 | 963.2 |
| 13 | 610.2 |
| 14 | 827.7 |
| 15 | 1113 |
| 16 | 1667 |
| 17 | 1700 |
| 18 | 1109 |
| 19 | 613.3 |
| 20 | 871.4 |
| 21 | 1063 |
| 22 | 1434 |
| 23 | 2094 |
| 24 | 840.2 |
| 25 | 431.2 |
| 26 | 1047 |
| 27 | 1136 |
| 28 | 1953 |
| 29 | 672.1 |
| 30 | 1071 |
| 31 | 143.8 |
| 32 | 2947 |
| 33 | 1439 |
| 34 | 1582 |
| 35 | 1335 |
| 36 | 1249 |
| 37 | 375.3 |
| 38 | 764.6 |
| 39 | 1351 |
| 40 | 167.9 |
| 41 | 1343 |
| 42 | 2220 |
| 43 | 1191 |
| 44 | 784.8 |
| 45 | 1582 |
| 46 | |
| 47 | 524.5 |
| 48 | 998.4 |

What is claimed is:

1. A compound according to Formula I or a pharmaceutically acceptable salt thereof

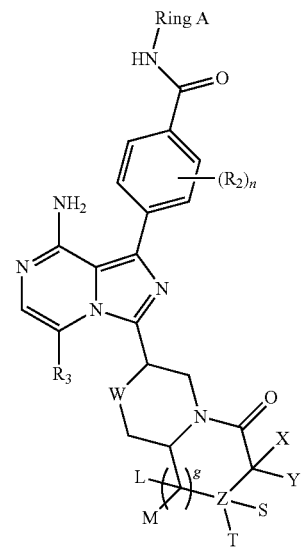

Formula I wherein:
Ring A is selected from the group consisting of

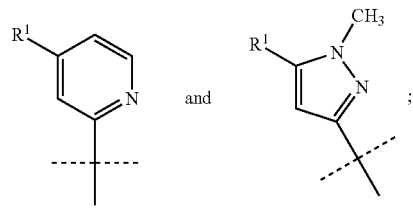

n is 0, 1 or 2; g is 0 or 1;
W is CH$_2$ or O;
Z is C or N;
X and Y are independently H or X and Y can come together to form cyclopropyl, cyclobutyl or cyclopentyl,
S and T are independently H, F, OH, OCH$_3$, methyl, ethyl or S and T can come together to form cyclopropyl, provided that when Z is C then S and T can come together to form =O,

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
1               5                   10                  15

M and L are independently H or M and L can come together to form cyclopropyl,

X and T can come together to form a one to three carbon bridge, wherein one of X and Y, S and T, M and L, and X and T must be a cyclic moiety;

$R^1$ is selected from the group consisting of hydrogen, triflouromethyl, cyclopropyl, methyl, and cyano;

$R_2$ is independently selected from the group consisting of methoxy, ethoxy and halogen; and $R_3$ is hydrogen, halogen, methyl, ethyl, propyl or isopropyl.

2. The compound according to claim 1 of Formula Ia or a pharmaceutically acceptable salt thereof

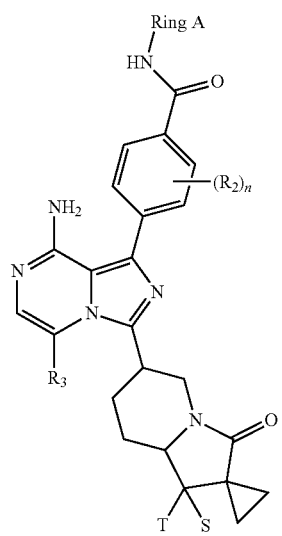

Formula Ia wherein:

Ring A is selected from the group consisting of

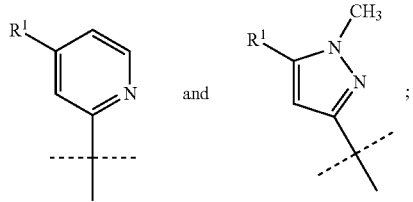

n is 0, 1 or 2;

S and T are independently H, F, OH, OCH$_3$, methyl, ethyl or S and T can come together to form =O;

$R^1$ selected from the group consisting of hydrogen, triflouromethyl, cyclopropyl, methyl, and cyano;

$R_2$ is independently selected from the group consisting of methoxy, ethoxy and halogen; and $R_3$ is hydrogen, halogen, methyl, ethyl, propyl or isopropyl.

3. The compound according to claim 1 of Formula Ib or a pharmaceutically acceptable salt thereof

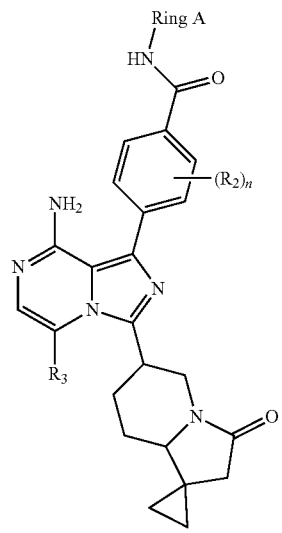

Formula Ib wherein:

Ring A is selected from the group consisting of

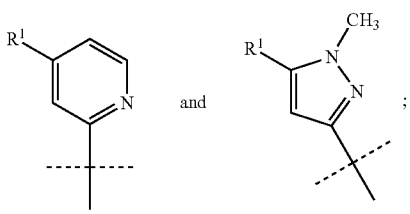

n is 0, 1 or 2;

$R^1$ is selected from the group consisting of hydrogen, triflouromethyl, cyclopropyl, methyl, and cyano;

$R_2$ is independently selected from the group consisting of methoxy, ethoxy and halogen; and $R_3$ is hydrogen, halogen, methyl, ethyl, propyl or isopropyl.

4. The compound of claim 1 selected from the group consisting of:

4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide;

4-(8-amino-3-((6'S,8a'R)-1',1'-difluoro-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide;

4-(8-amino-3-((6'R,8a'S)-1',1'-difluoro-3'-oxohexahydro-1'H-spiro[cyclopropane-1,2'-indolizin]-6'-yl)imidazo[1,5-a]pyrazin-1-yl)-3-ethoxy-N-(4-(trifluoromethyl)pyridin-2-yl)benzamide;

4-(8-amino-3-((6'R,8a'S)-3'-oxohexahydro-1'H-spiro[cyclopropane-1,2'-indolizin]-6'-yl)imidazo[1,5-a]pyrazin-1-yl)-3-ethoxy-5-fluoro-N-(4-(trifluoromethyl)pyridin-2-yl)benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-N-[4-(trifluoromethyl)pyridin-2-yl]benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-3-fluoro-N-[4-(trifluoromethyl)pyridin-2-yl]benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-N-(4-methylpyridin-2-yl)benzamide;

4-{8-amino-3-[(6'R,8a'S)-1',3'-dioxohexahydrospiro[cyclopropane-1,2'-indolizin]-6'-yl]imidazo[1,5-a]pyrazin-1-yl}-N-(4-cyclopropylpyridin-2-yl)benzamide;

4-{8-amino-3-[(1'S,6'R,8a'S)-1'-hydroxy-3'-oxohexahydrospiro[cyclopropane-1,2'-indolizin]-6'-yl]imidazo[1,5-a]pyrazin-1-yl}-N-[4-(trifluoromethyl)pyridin-2-yl]benzamide;

4-{8-amino-3-[(1'S,6'R,8a'S)-1'-hydroxy-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;

4-(8-amino-3-((1'S,6'R,8a'S)-1'-hydroxy-3'-oxohexahydro-1'H-spiro[cyclopropane-1,2'-5-a]pyrazin-1-yl)-3-fluoro-N-(4-(trifluoromethyl)pyridin-2-yl)benzamide;

4-(8-amino-3-((1'S,6'R,8a'S)-1'-hydroxy-3'-oxohexahydro-1'H-spiro[cyclopropane-1,2'-indolizin]-6'-yl)imidazo[1,5-a]pyrazin-1-yl)-N-(4-cyclopropylpyridin-2-yl)benzamide;

4-(8-amino-3-((1'S,6'R,8a'S)-1'-methoxy-3'-oxohexahydro-1'H-spiro[cyclopropane-1,2'-5-a]pyrazin-1-yl)-3-ethoxy-N-(4-(trifluoromethyl)pyridin-2-yl)benzamide;

4-{8-amino-3-[(5aS,8R,11aR)-11-oxodecahydro-1H-pyrido[1,2-a]pyrrolo[1,2-d]pyrazin-8-yl]imidazo[1,5-a]pyrazin-1-yl}-3-ethoxy-N-[4-(trifluoromethyl)pyridin-2-yl]benzamide;

4-{8-amino-3-[(5aS,8R,11aS)-11-oxodecahydro-1H-pyrido[1,2-a]pyrrolo[1,2-d]pyrazin-8-yl]imidazo[1,5-a]pyrazin-1-yl}-3-ethoxy-N-[4-(trifluoromethyl)pyridin-2-yl]benzamide;

4-{8-amino-3-[(7'R,9a'S)-4'-oxohexahydro-2'H-spiro[cyclobutane-1,3'-pyrido[1,2-a]pyrazin]-7'-yl]imidazo[1,5-a]pyrazin-1-yl}-3-ethoxy-N-[4-(trifluoromethyl)pyridin-2-yl]benzamide;

4-{8-amino-3-[(6'R,8a'S)-3'-oxohexahydro-5'H-spiro[cyclopropane-1,1'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'S, 8a'R)-3'-oxohexahydro-5'H-spiro[cyclopropane-1,1'-indolizin]-6'-yl]imidazo[1,5-a]pyrazin-1-yl}-3-ethoxy-N-[4-(trifluoromethyl)pyridin-2-yl]benzamide;

4-{8-amino-3-[(6'R,8a'S)-3'-oxohexahydro-5'H-spiro[cyclopropane-1,1'-indolizin]-6'-yl]imidazo[1,5-a]pyrazin-1-yl}-3-ethoxy-5-fluoro-N-[4-(trifluoromethyl)pyridin-2-yl]benzamide;

4-{8-amino-3-[(6'R,8a'S)-3'-oxohexahydro-5'H-spiro[cyclopropane-1,1'-indolizin]-6'-yl]imidazo[1,5-a]pyrazin-1-yl}-N-(4-cyclopropylpyridin-2-yl)-3-ethoxy-5-fluorobenzamide;

4-[8-amino-5-fluoro-3-(3'-oxohexahydro-5'H-spiro[cyclopropane-1,1'-indolizin]-6'-yl)imidazo[1,5-a]pyrazin-1-yl]-3-ethoxy-5-fluoro-N-[1-methyl-5-(trifluoromethyl)-1H-pyrazol-3-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-ethoxy-5-fluoro-N-[4-(trifluoromethyl)pyridin-2-yl]benzamide;

4-{8-amino-3-[(6'S, 8a'R)-1',1'-difluoro-3'-oxohexahydrospiro[cyclopropane-1,2'-indolizin]-6'-yl]imidazo[1,5-a]pyrazin-1-yl}-3-methoxy-N-[4-(trifluoromethyl)pyridin-2-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-fluoro-5-methoxy-N-[4-(trifluoromethyl)pyridin-2-yl]benzamide;

4-{8-amino-3-[(6'S,8a'R)-1',1'-difluoro-3'-oxohexahydrospiro[cyclopropane-1,2'-indolizin]-6'-yl]imidazo[1,5-a]pyrazin-1-yl}-N-[4-(trifluoromethyl)pyridin-2-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-3-ethoxy-N-[1-methyl-5-(trifluoromethyl)-1H-pyrazol-3-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-5-ethoxy-2-fluoro-N-[1-methyl-5-(trifluoromethyl)-1H-pyrazol-3-yl]benzamide;

4-{8-amino-3-[(6'R,8a'S)-1',1'-difluoro-3'-oxohexahydrospiro[cyclopropane-1,2'-indolizin]-6'-yl]imidazo[1,5-a]pyrazin-1-yl}-2-chloro-5-ethoxy-N-[1-methyl-5-(trifluoromethyl)-1H-pyrazol-3-yl]benzamide;

4-{8-amino-3-[(3R,6aR,11aR)-6-oxooctahydro-1H,6H-pyrrolo[1',2':4,5]pyrazino[2,1-c] [1,4]oxazin-3-yl]imidazo[1,5-a]pyrazin-1-yl}-3-ethoxy-N-[4-(trifluoromethyl)pyridin-2-yl]benzamide;

4-{8-amino-3-[(3R,6aS,11aR)-6-oxooctahydro-1H,6H-pyrrolo[1',2':4,5]pyrazino[2,1-c][1,4]oxazin-3-yl]imidazo[1,5-a]pyrazin-1-yl}-3-ethoxy-N-[4-(trifluoromethyl)pyridin-2-yl]benzamide;

4-[8-amino-5-chloro-3-(3'-oxohexahydro-5'H-spiro[cyclopropane-1,1'-indolizin]-6'-yl)imidazo[1,5-a]pyrazin-1-yl]-N-(4-cyanopyridin-2-yl)-3-ethoxy-5-fluorobenzamide;

4-[8-amino-3-(3'-oxohexahydro-5'H-spiro[cyclopropane-1,1'-indolizin]-6'-yl)imidazo[1,5-a]pyrazin-1-yl]-N-(4-cyanopyridin-2-yl)-3-ethoxy-5-fluorobenzamide;

4-[8-amino-3-(4'-oxohexahydro-2'H,6'H-spiro[cyclopropane-1,1'-pyrido[1,2-a]pyrazin]-7'-yl)imidazo[1,5-a]pyrazin-1-yl]-3-ethoxy-N-[4-(trifluoromethyl)pyridin-2-yl]benzamide;

4-{8-amino-3-[(7'R,9a'S)-4'-oxohexahydro-2'H-spiro[cyclopropane-1,3'-pyrido[1,2-a]pyrazin]-7'-yl]imidazo[1,5-a]pyrazin-1-yl}-N-[4-(trifluoromethyl)pyridin-2-yl]benzamide;

4-{8-amino-3-[(7'R,9a'S)-4'-oxohexahydro-2'H-spiro[cyclopropane-1,3'-pyrido[1,2-a]pyrazin]-7'-yl]imidazo[1,5-a]pyrazin-1-yl}-3-methoxy-N-[4-(trifluoromethyl)pyridin-2-yl]benzamide;

4-{8-amino-3-[(7'R,9a'S)-2'-ethyl-4'-oxohexahydro-2'H-spiro[cyclopropane-1,3'-pyrido[1,2-a]pyrazin]-7'-yl]imidazo[1,5-a]pyrazin-1-yl}-3-ethoxy-N-[4-(trifluoromethyl)pyridin-2-yl]benzamide;

4-{8-amino-3-[(3'R,9a'R)-6'-oxohexahydrospiro[cyclopropane-1,7'-pyrazino[2,1-c][1,4]oxazin]-3'-yl]imidazo[1,5-a]pyrazin-1-yl}-3-ethoxy-N-[4-(trifluoromethyl)pyridin-2-yl]benzamide;

4-{8-amino-3-[(3'R,9a'R)-6'-oxohexahydrospiro[cyclopentane-1,7'-pyrazino[2,1-c][ 1,4]oxazin]-3'-yl]imidazo[1,5-a]pyrazin-1-yl}-3-ethoxy-N-[4-(trifluoromethyl)pyridin-2-yl]benzamide;

4-{8-amino-3-[(6'S, 8a'R)-3'-oxohexahydrospiro[cyclopropane-1,2'-indolizin]-6'-yl]imidazo[1,5-a]pyrazin-1-yl}-3-methoxy-N-[4-(trifluoromethyl)pyridin-2-yl]benzamide; and 4-{8-amino-3-[(6'S, 8a'R)-3'-oxohexahydrospiro[cyclopropane-1,2'-indolizin]-6'-yl]imidazo[1,5-a]pyrazin-1-yl}-3-ethoxy-N-[4-(trifluoromethyl)pyridin-2-yl]benzamide;
or a pharmaceutically acceptable salt thereof.

5. A pharmaceutical composition which comprises the compound of claim 1 or a pharmaceutically acceptable salt thereof and one or more pharmaceutically acceptable carriers.

* * * * *